(12) United States Patent
Juravic et al.

(10) Patent No.: US 11,806,047 B2
(45) Date of Patent: *Nov. 7, 2023

(54) METHODS AND APPARATUS FOR PREVENTING VAGINAL LACERATIONS DURING CHILDBIRTH

(71) Applicant: Materna Medical, Inc., Mountain View, CA (US)

(72) Inventors: Mark Juravic, Encinitas, CA (US); Michael Stewart, San Jose, CA (US)

(73) Assignee: MATERNA MEDICAL, INC

( * ) Notice: Subject to any disclaimer, the term of this patent is extended or adjusted under 35 U.S.C. 154(b) by 0 days.

This patent is subject to a terminal disclaimer.

(21) Appl. No.: 17/713,933

(22) Filed: Apr. 5, 2022

(65) Prior Publication Data

US 2022/0226021 A1 Jul. 21, 2022

Related U.S. Application Data

(63) Continuation of application No. 15/050,287, filed on Feb. 22, 2016, now abandoned, which is a
(Continued)

(51) Int. Cl.
*A61B 17/42* (2006.01)
*A61B 1/303* (2006.01)
(Continued)

(52) U.S. Cl.
CPC ............... *A61B 17/42* (2013.01); *A61B 1/303* (2013.01); *A61B 1/31* (2013.01); *A61B 5/22* (2013.01);
(Continued)

(58) Field of Classification Search
None
See application file for complete search history.

(56) References Cited

U.S. PATENT DOCUMENTS 237,032 A 1/1881 Mayer
242,443 A 6/1881 Foote
(Continued)

FOREIGN PATENT DOCUMENTS

CN 2262410 Y 9/1997
CN 2555047 Y 6/2003
(Continued)

OTHER PUBLICATIONS

Hofmeyr et al.; An inflatable birth canal dilator; SAMJ; vol. 80; pp. 198-199; Aug. 17, 1991.
(Continued)

*Primary Examiner* — Matthew Kremer
(74) *Attorney, Agent, or Firm* — Boston & Galway, LLC

(57) ABSTRACT

A vaginal dilation device is provided that may include any of a number of features. One feature of the vaginal dilation device is that it is configured to dilate vaginal tissue during labor to prevent tissue damage. Another feature of the vaginal dilation device is that it can be manually controlled to dilate vaginal tissue, or can be automatically controlled to dilate vaginal tissue. In some embodiments, the vaginal dilation device is configured to measure a force applied by the device to tissue. In other embodiments, the vaginal dilation device is configured to apply a constant force to tissue. In other embodiments, the vaginal dilation device is configured to expand at a constant rate. Methods associated with use of the vaginal dilation device are also provided.

14 Claims, 46 Drawing Sheets

Related U.S. Application Data continuation of application No. 13/876,920, filed as application No. PCT/US2011/032324 on Apr. 13, 2011, now abandoned, which is a continuation-in-part of application No. PCT/US2010/052528, filed on Oct. 13, 2010.

(51) Int. Cl.

| | | |
|---|---|---|
| *A61B 1/31* | (2006.01) | |
| *A61B 17/34* | (2006.01) | |
| *A61M 29/02* | (2006.01) | |
| *A61B 5/00* | (2006.01) | |
| *A61B 5/22* | (2006.01) | |
| *A61B 17/02* | (2006.01) | |
| *A61B 90/00* | (2016.01) | |
| *A61B 17/00* | (2006.01) | |

(52) U.S. Cl.
CPC .............. *A61B 5/227* (2013.01); *A61B 5/435* (2013.01); *A61B 5/4343* (2013.01); *A61B 5/4836* (2013.01); *A61B 17/0206* (2013.01); *A61B 17/3423* (2013.01); *A61B 90/03* (2016.02); *A61B 90/06* (2016.02); *A61M 29/02* (2013.01); *A61B 17/02* (2013.01); *A61B 17/3439* (2013.01); *A61B 2017/00119* (2013.01); *A61B 2017/00199* (2013.01); *A61B 2017/345* (2013.01); *A61B 2090/036* (2016.02); *A61B 2090/065* (2016.02)

(56) References Cited

U.S. PATENT DOCUMENTS

| | | | |
|---|---|---|---|
| 275,405 A | 4/1883 | Parker | |
| 292,381 A | 1/1884 | Stiles | |
| 316,611 A | 4/1885 | Farr | |
| 318,535 A | 5/1885 | Bihler | |
| 365,969 A | 7/1887 | Collins | |
| 376,727 A | 1/1888 | Beall | |
| 458,022 A | 8/1891 | JeanJaquet | |
| 458,457 A | 8/1891 | Hendrickson | |
| 468,620 A | 2/1892 | Hitt | |
| 540,835 A | 6/1895 | Gunning | |
| 577,775 A | 2/1897 | Mussey | |
| 705,371 A | 7/1902 | Anderson et al. | |
| 837,085 A | 11/1906 | Loar | |
| 899,477 A | 9/1908 | Williams | |
| 923,303 A | 6/1909 | Shults | |
| 972,983 A | 12/1909 | Arthur | |
| 1,034,818 A | 8/1912 | Mulgrew | |
| 1,076,221 A | 12/1912 | Miner | |
| 1,244,751 A | 10/1917 | McCleary | |
| 1,271,456 A | 7/1918 | Flack | |
| 1,382,982 A | 6/1921 | Jeanjaquet | |
| 1,413,789 A | 4/1922 | Van Schaff | |
| 1,428,653 A | 9/1922 | Nick | |
| 1,448,158 A | 3/1923 | Sims | |
| 1,528,858 A | 3/1925 | Sims | |
| 1,582,690 A | 4/1926 | Reggio | |
| 1,737,488 A | 11/1929 | Zohlen | |
| 1,764,838 A | 6/1930 | Horne | |
| 1,827,497 A | 10/1931 | Thomas | |
| 2,026,747 A | 1/1936 | Nemzek | |
| 2,083,573 A | 6/1937 | Morgan | |
| 2,137,121 A | 11/1938 | Fannie | |
| 2,507,858 A | 5/1950 | Kegel | |
| 2,541,520 A | 2/1951 | Kegel | |
| 2,610,626 A | 9/1952 | Edwards | |
| 2,849,001 A | 8/1958 | Oddo | |
| 2,849,002 A | 8/1958 | Oddo | |
| 3,039,462 A | 6/1962 | Walden et al. | |
| 3,045,677 A | 7/1962 | Wallace | |
| 3,192,928 A | 7/1965 | Horton | |
| 3,480,017 A | 11/1969 | Shute | |
| 3,502,328 A | 3/1970 | Hamilton | |
| 3,517,128 A | 6/1970 | Hines | |
| 3,532,088 A | 10/1970 | Fiore | |
| 3,565,061 A | 2/1971 | Reynolds | |
| 3,626,949 A | 12/1971 | Shute | |
| 3,769,968 A | 11/1973 | Blount et al. | |
| 3,799,170 A | 3/1974 | Walsh et al. | |
| 3,841,318 A | 10/1974 | Olson | |
| 3,916,906 A | 11/1975 | Gerry | |
| 3,968,800 A | 7/1976 | Villasi | |
| 4,018,231 A | 4/1977 | Wallace | |
| 4,050,449 A | 9/1977 | Castellana et al. | |
| 4,130,113 A | 12/1978 | Graham | |
| 4,167,938 A | 9/1979 | Remih | |
| 4,198,981 A | 4/1980 | Sinnreich | |
| 4,241,912 A | 12/1980 | Mercer et al. | |
| 4,306,459 A | 12/1981 | Johnson et al. | |
| 4,396,019 A | 8/1983 | Perry | |
| 4,476,880 A | 10/1984 | Giem et al. | |
| 4,515,167 A | 5/1985 | Hochman | |
| 4,566,465 A | 1/1986 | Arhan et al. | |
| 4,653,514 A | 3/1987 | Shapiro | |
| 4,664,114 A | 5/1987 | Ghodsian | |
| 4,677,967 A | 7/1987 | Zartman | |
| 4,749,186 A | 6/1988 | Randle | |
| 4,753,238 A | 6/1988 | Gaiser | |
| 4,768,522 A | 9/1988 | Shapiro | |
| 4,785,828 A | 11/1988 | Maurer | |
| 4,832,691 A | 5/1989 | Witzel | |
| 4,875,482 A | 10/1989 | Hariri et al. | |
| 4,884,559 A | 12/1989 | Collins | |
| 4,971,036 A | 11/1990 | Collins | |
| 5,072,720 A | 12/1991 | Francis et al. | |
| 5,081,983 A | 1/1992 | Villalta et al. | |
| 5,147,377 A | 9/1992 | Sahota | |
| 5,179,937 A | 1/1993 | Lee | |
| 5,209,754 A | 5/1993 | Ahluwalia | |
| 5,231,973 A | 8/1993 | Dickie | |
| 5,275,610 A | 1/1994 | Eberbach | |
| 5,338,297 A | 8/1994 | Kocur et al. | |
| 5,354,250 A | 10/1994 | Christensen | |
| 5,377,667 A | 1/1995 | Patton et al. | |
| 5,465,709 A | 11/1995 | Dickie et al. | |
| 5,483,832 A | 1/1996 | Pauser et al. | |
| 5,509,893 A | 4/1996 | Pracas | |
| 5,674,238 A | 10/1997 | Sample et al. | |
| 5,681,340 A | 10/1997 | Veronikis | |
| 5,733,230 A | 3/1998 | Sawchuck et al. | |
| 5,743,852 A | 4/1998 | Johnson | |
| 5,746,750 A | 5/1998 | Prestel et al. | |
| 5,762,589 A | 6/1998 | Parker, Jr. | |
| 5,795,289 A | 8/1998 | Wyttenbach | |
| 5,865,715 A | 2/1999 | Wallick | |
| 5,876,357 A * | 3/1999 | Tomer .................. | A61B 5/1076 |
| | | | 600/587 |
| 5,916,151 A | 6/1999 | Charters | |
| 5,947,991 A | 9/1999 | Cowan | |
| 6,024,696 A | 2/2000 | Hoftman et al. | |
| 6,024,697 A | 2/2000 | Pisarik | |
| 6,027,519 A | 2/2000 | Stanford | |
| 6,048,308 A | 4/2000 | Strong | |
| 6,059,740 A | 5/2000 | Leivseth et al. | |
| 6,063,045 A | 5/2000 | Wax et al. | |
| 6,068,581 A | 5/2000 | Anderson | |
| D428,631 S | 7/2000 | Stein | |
| 6,086,549 A | 7/2000 | Neese et al. | |
| 6,096,046 A | 8/2000 | Weiss | |
| 6,159,170 A | 12/2000 | Borodulin et al. | |
| 6,224,525 B1 | 5/2001 | Stein | |
| 6,224,580 B1 | 5/2001 | Christensen | |
| 6,258,015 B1 | 7/2001 | Blackford et al. | |
| D446,856 S | 8/2001 | Stein | |
| D446,857 S | 8/2001 | Stein | |
| D447,234 S | 8/2001 | Stein | |
| D447,235 S | 8/2001 | Stein | |
| D447,236 S | 8/2001 | Stein | |
| 6,280,379 B1 | 8/2001 | Resnick | |
| D447,562 S | 9/2001 | Stein | |

(56) References Cited

U.S. PATENT DOCUMENTS

| | | |
|---|---|---|
| D447,563 S | 9/2001 | Stein |
| D447,800 S | 9/2001 | Stein |
| D448,080 S | 9/2001 | Moscarelli et al. |
| 6,302,842 B1 | 10/2001 | Auerbach et al. |
| 6,342,036 B1 | 1/2002 | Cooper et al. |
| 6,354,995 B1 | 3/2002 | Hoftman et al. |
| 6,402,683 B1 | 6/2002 | Marty |
| 6,468,232 B1 | 10/2002 | Miller et al. |
| 6,540,667 B2 | 4/2003 | Hickman |
| 6,672,996 B2 | 1/2004 | Ross et al. |
| 6,688,310 B1 | 2/2004 | Toliver |
| 6,749,563 B2 | 6/2004 | Stihl |
| 6,752,749 B2 | 6/2004 | Stein |
| 6,758,796 B2 | 7/2004 | Stein |
| 6,773,380 B2 | 8/2004 | Stein |
| 6,843,251 B1 | 1/2005 | Huerland et al. |
| 6,869,398 B2 | 3/2005 | Obenchain et al. |
| 6,905,471 B2 | 6/2005 | Leivseth et al. |
| 6,932,764 B2 | 8/2005 | Kashyap |
| 7,001,317 B2 | 2/2006 | Marcotte |
| 7,014,603 B2 | 3/2006 | Stein |
| 7,060,029 B1 | 6/2006 | Hajianpour |
| 7,141,015 B2 | 11/2006 | Ruane |
| 7,182,730 B2 | 2/2007 | Fehling |
| 7,322,935 B2 | 1/2008 | Palmer et al. |
| 7,481,766 B2 | 1/2009 | Lee et al. |
| 7,497,816 B2 | 3/2009 | Li |
| 7,577,476 B2 | 8/2009 | Hochman et al. |
| 7,628,744 B2 | 12/2009 | Hoffman et al. |
| 7,645,220 B2 | 1/2010 | Hoffman et al. |
| 7,648,470 B2 * | 1/2010 | Omata .................... A61B 5/202 600/587 |
| 7,713,216 B2 | 5/2010 | Dubey et al. |
| 7,771,344 B2 | 8/2010 | Ziv |
| 8,097,014 B2 | 1/2012 | Borkon |
| 8,118,726 B1 | 2/2012 | Blackford |
| 8,187,208 B2 | 5/2012 | Egorov et al. |
| 8,876,711 B2 | 11/2014 | Lin et al. |
| 9,492,197 B2 * | 11/2016 | Juravic .................... A61B 1/31 |
| 10,828,476 B2 | 11/2020 | Juravic |
| 2001/0041874 A1 | 11/2001 | Reydel |
| 2002/0010441 A1 | 1/2002 | Horkel |
| 2002/0016528 A1 | 2/2002 | Tan |
| 2002/0068900 A1 | 6/2002 | Barnes et al. |
| 2002/0095160 A1 | 7/2002 | Bonutti |
| 2003/0036464 A1 | 2/2003 | Zavilevich |
| 2003/0069476 A1 | 4/2003 | Deslauriers et al. |
| 2003/0078526 A1 | 4/2003 | Farley |
| 2003/0087734 A1 | 5/2003 | Kring et al. |
| 2003/0105387 A1 | 6/2003 | Frumovitz et al. |
| 2004/0038783 A1 | 2/2004 | Hunter |
| 2004/0153116 A1 | 8/2004 | Nobles et al. |
| 2004/0225235 A1 | 11/2004 | Ben-Cnaan et al. |
| 2005/0049509 A1 | 3/2005 | Mansour et al. |
| 2005/0148447 A1 | 7/2005 | Nady |
| 2005/0154263 A1 | 7/2005 | Nady |
| 2005/0250993 A1 | 11/2005 | Jaeger |
| 2006/0058831 A1 | 3/2006 | Atad |
| 2006/0122463 A1 * | 6/2006 | Klaassen .................... A61B 1/32 600/221 |
| 2006/0200187 A1 | 9/2006 | Gude |
| 2007/0043264 A1 | 2/2007 | Gillis et al. |
| 2007/0043388 A1 | 2/2007 | Greenwood |
| 2007/0156068 A1 * | 7/2007 | Dubey .................... A61B 5/6885 600/588 |
| 2008/0039865 A1 | 2/2008 | Shaher et al. |
| 2008/0058604 A1 | 3/2008 | Sorensen |
| 2008/0139876 A1 | 6/2008 | Kim |
| 2008/0234719 A1 | 9/2008 | Adams |
| 2008/0249534 A1 | 10/2008 | Gruber et al. |
| 2009/0012556 A1 | 1/2009 | Boudreaux et al. |
| 2009/0099422 A1 | 4/2009 | George |
| 2010/0048977 A1 | 2/2010 | Sing et al. |
| 2010/0048978 A1 | 2/2010 | Sing et al. |
| 2010/0113939 A1 | 5/2010 | Mashimo et al. |
| 2010/0160947 A1 | 6/2010 | Akyuz et al. |
| 2010/0174148 A1 | 7/2010 | Miles et al. |
| 2010/0185123 A1 | 7/2010 | Zanetti et al. |
| 2010/0217088 A1 | 8/2010 | Heiges et al. |
| 2010/0217090 A1 | 8/2010 | Heiges et al. |
| 2010/0274159 A1 * | 10/2010 | Perle .................... A61F 6/08 600/591 |
| 2010/0305406 A1 | 12/2010 | Braun et al. |
| 2011/0034776 A1 | 2/2011 | Dixon et al. |
| 2013/0144388 A1 | 6/2013 | Emery et al. |
| 2013/0253376 A1 | 9/2013 | Juravic et al. |
| 2014/0179990 A1 | 6/2014 | Davila et al. |
| 2016/0166282 A1 | 6/2016 | Juravic et al. |
| 2017/0056069 A1 | 3/2017 | Juravic et al. |
| 2021/0052867 A1 | 2/2021 | Juravic |

FOREIGN PATENT DOCUMENTS

| | | | |
|---|---|---|---|
| CN | 203424920 U | 2/2014 | |
| CN | 204364536 U | 6/2015 | |
| DE | 3803727 C1 | 4/1989 | |
| DE | 3800744 C1 | 5/1989 | |
| EP | 663197 B1 | 7/1995 | |
| EP | 0574966 B1 | 3/1996 | |
| EP | 1600103 A1 | 11/2005 | |
| EP | 2229884 A1 | 9/2010 | |
| FR | 592104 | 7/1925 | |
| FR | 2071338 | 9/1971 | |
| GB | 15314 A | 8/1903 | |
| GB | 2297036 A | 7/1996 | |
| GB | 2444034 A * | 5/2008 | ............. A61H 19/34 |
| JP | H10-305042 A | 11/1998 | |
| JP | 2005287989 A | 10/2005 | |
| KR | 1992-0021172 | 12/1992 | |
| KR | 2000-0011380 | 7/2000 | |
| RU | 2071285 C1 | 1/1997 | |
| WO | WO98/09565 A1 | 3/1998 | |
| WO | WO98/42400 A1 | 10/1998 | |
| WO | WO00/12832 A2 | 3/2000 | |
| WO | WO01/10493 A1 | 2/2001 | |
| WO | WO01/41627 A2 | 6/2001 | |
| WO | WO01/68181 A1 | 9/2001 | |
| WO | WO2004/062489 A1 | 7/2004 | |
| WO | WO2005/037361 A2 | 4/2005 | |
| WO | WO2009/000056 A2 | 12/2008 | |
| WO | WO2009/110863 A1 | 9/2009 | |
| WO | WO2009/158435 A1 | 12/2009 | |
| WO | WO2010/076555 A1 | 7/2010 | |
| WO | WO2010/080497 A2 | 7/2010 | |
| WO | WO2011/064774 A1 | 6/2011 | |
| WO | WO2014/062809 A1 | 4/2014 | |

OTHER PUBLICATIONS

Lee et al.; Cervetics (Business Proposal) Dila-Pro: A smart cervical dilation device; pp. 1-10; Dec. 14, 2009.

Lee et al.; Cervetics (Design Summary) Dila-Pro: A smart cervical dilation device; pp. 1-48; Dec. 14, 2009.

* cited by examiner

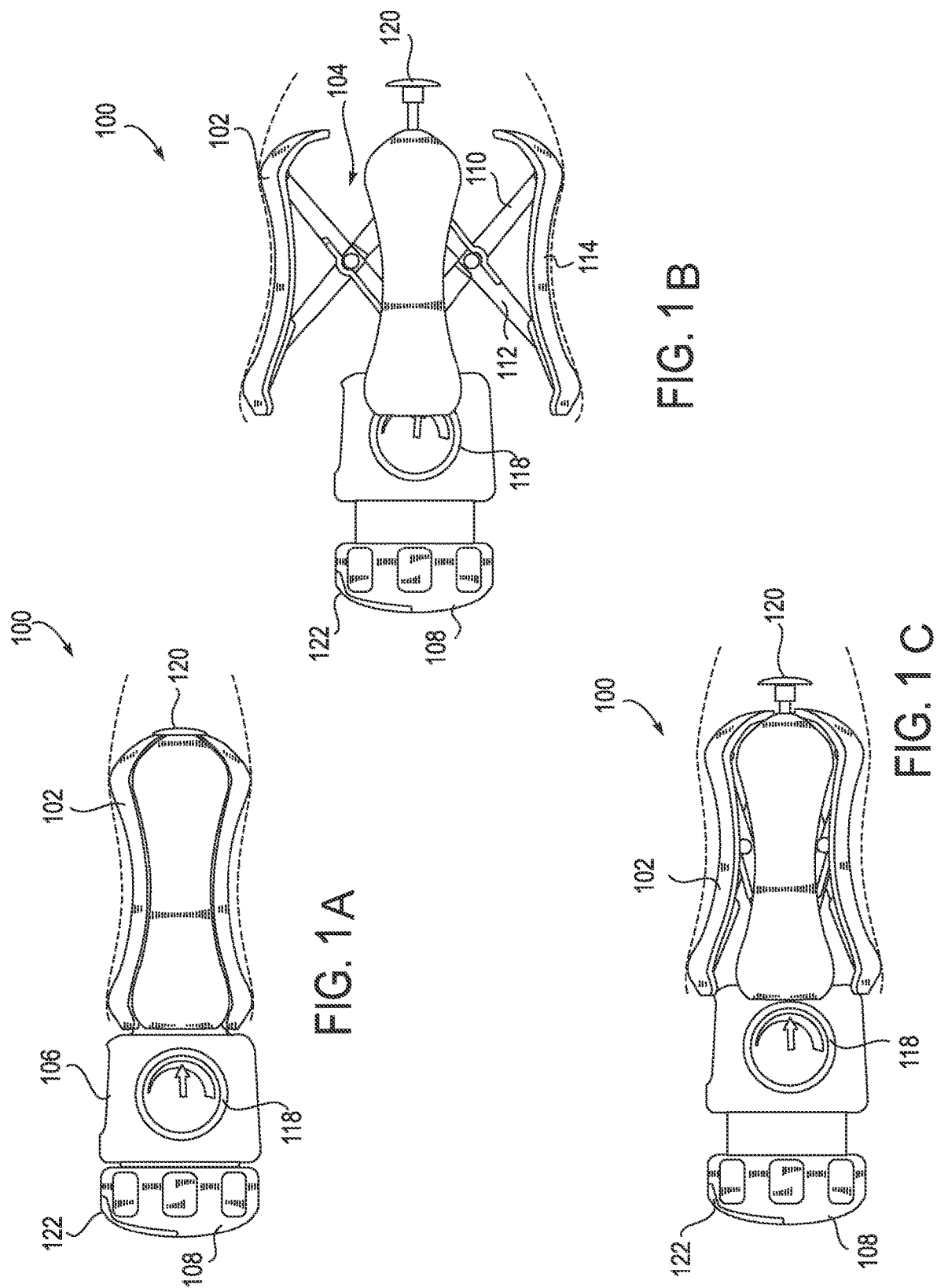

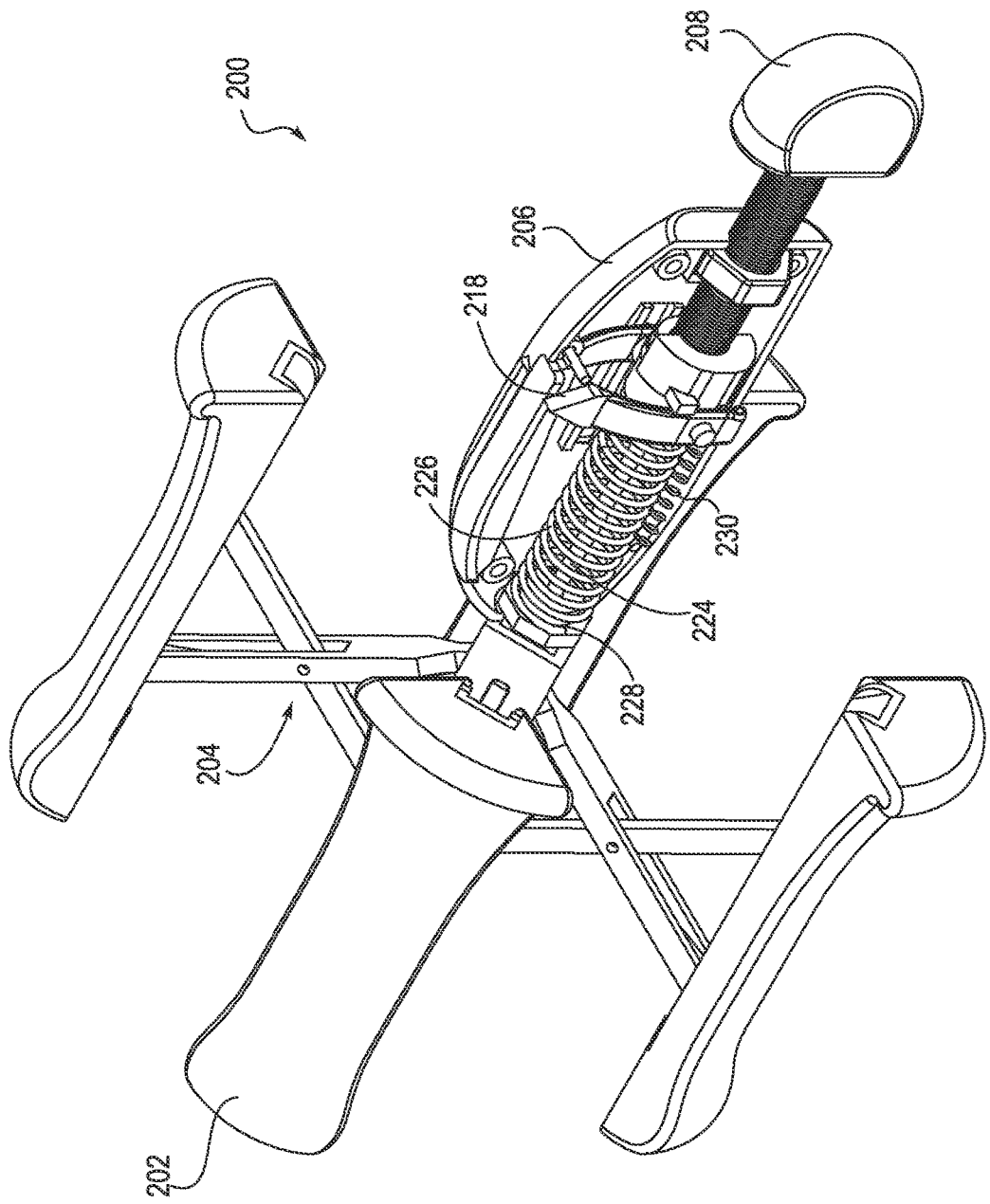

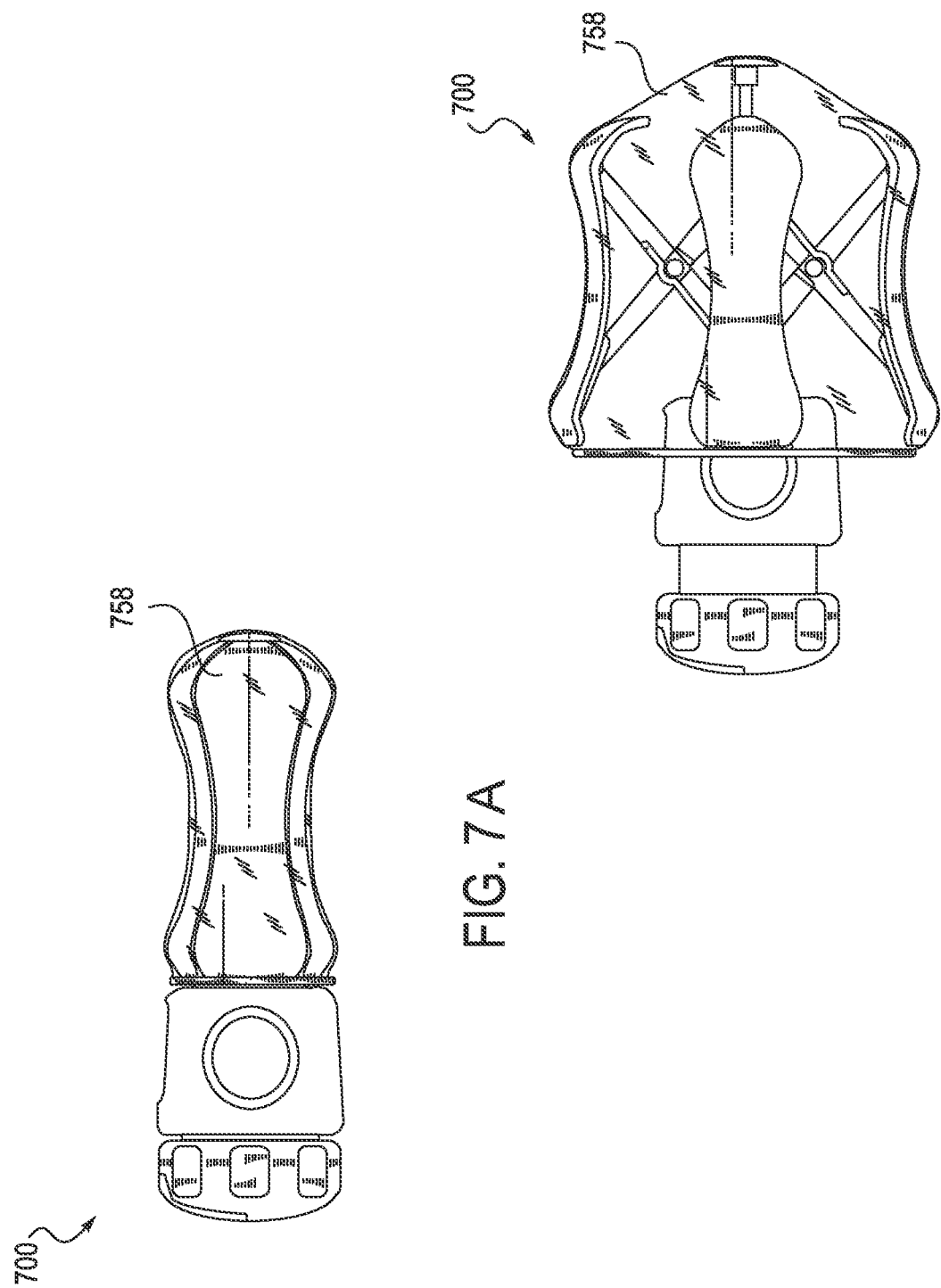

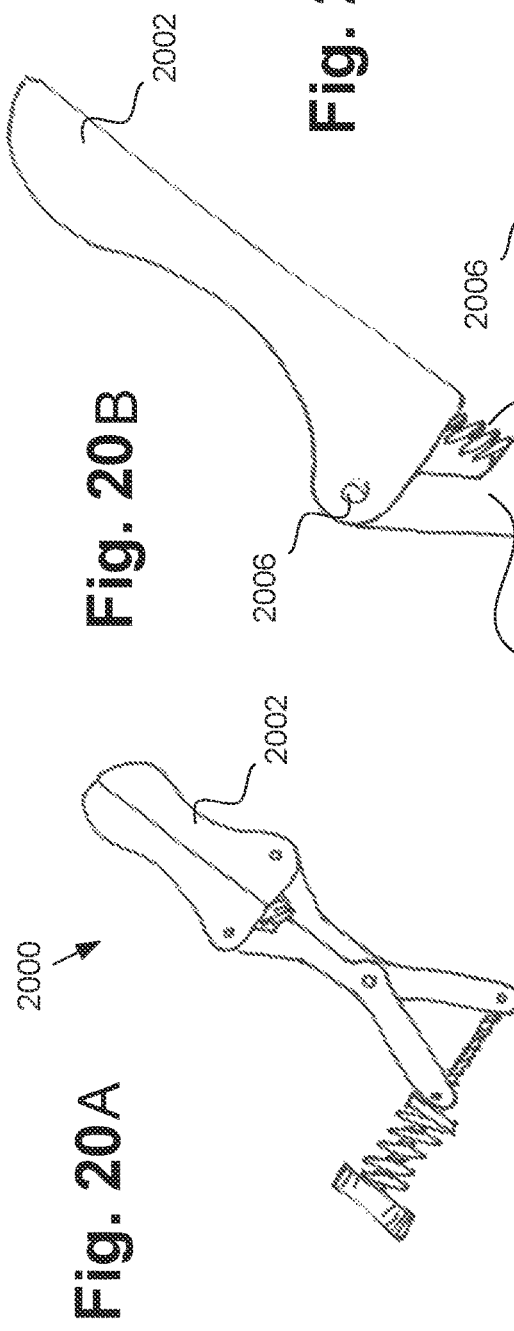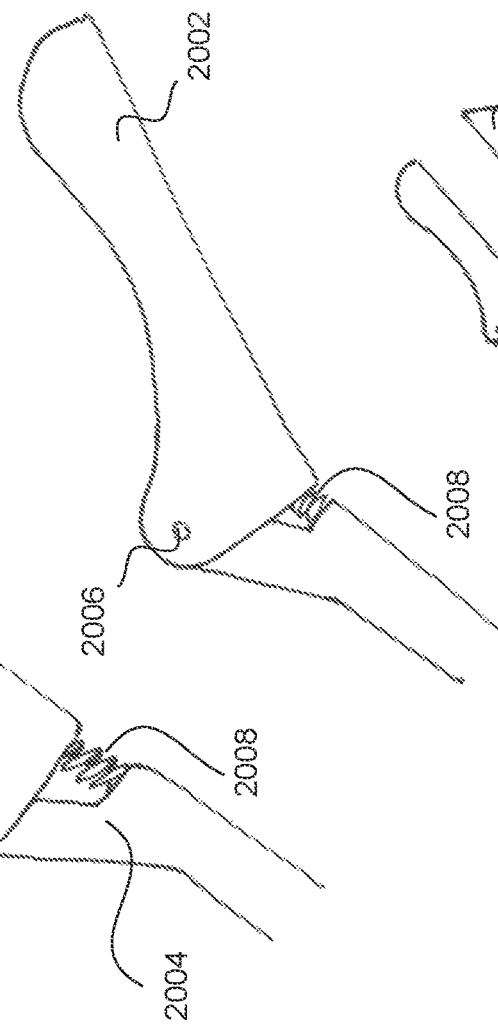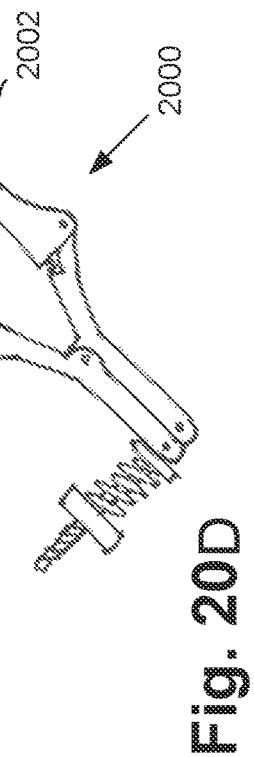

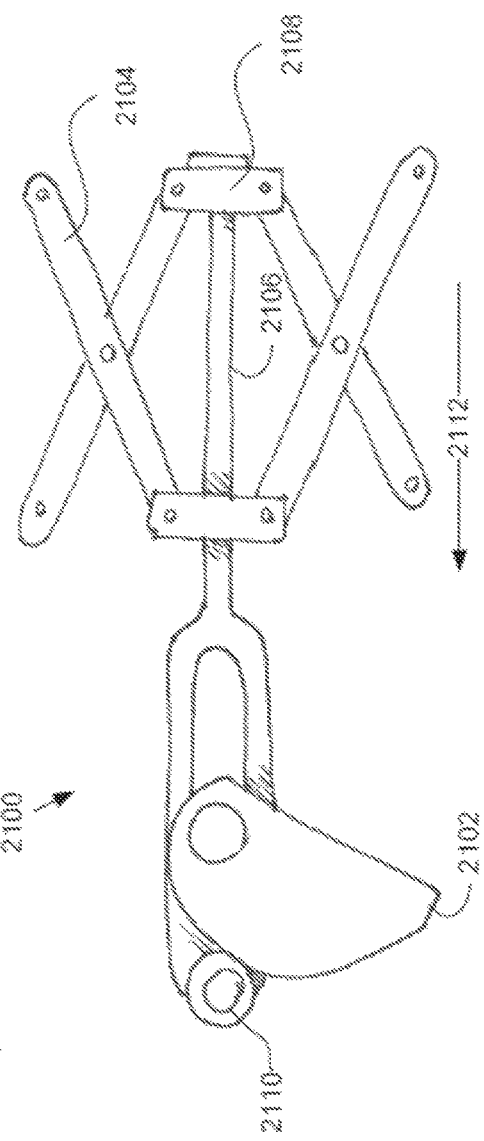
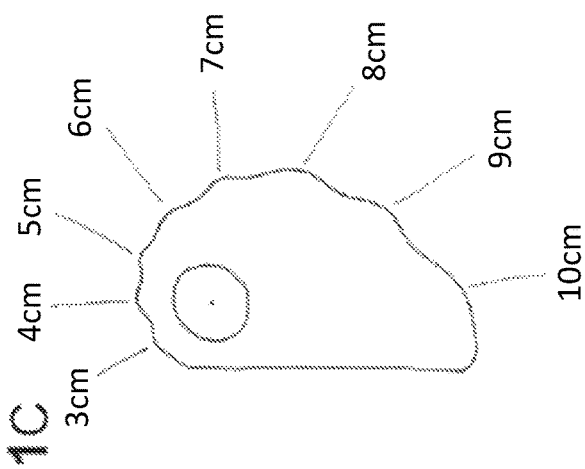
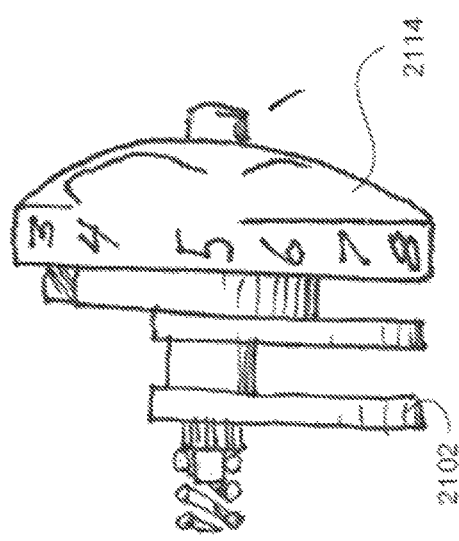
Fig. 21A
Fig. 21C
Fig. 21B

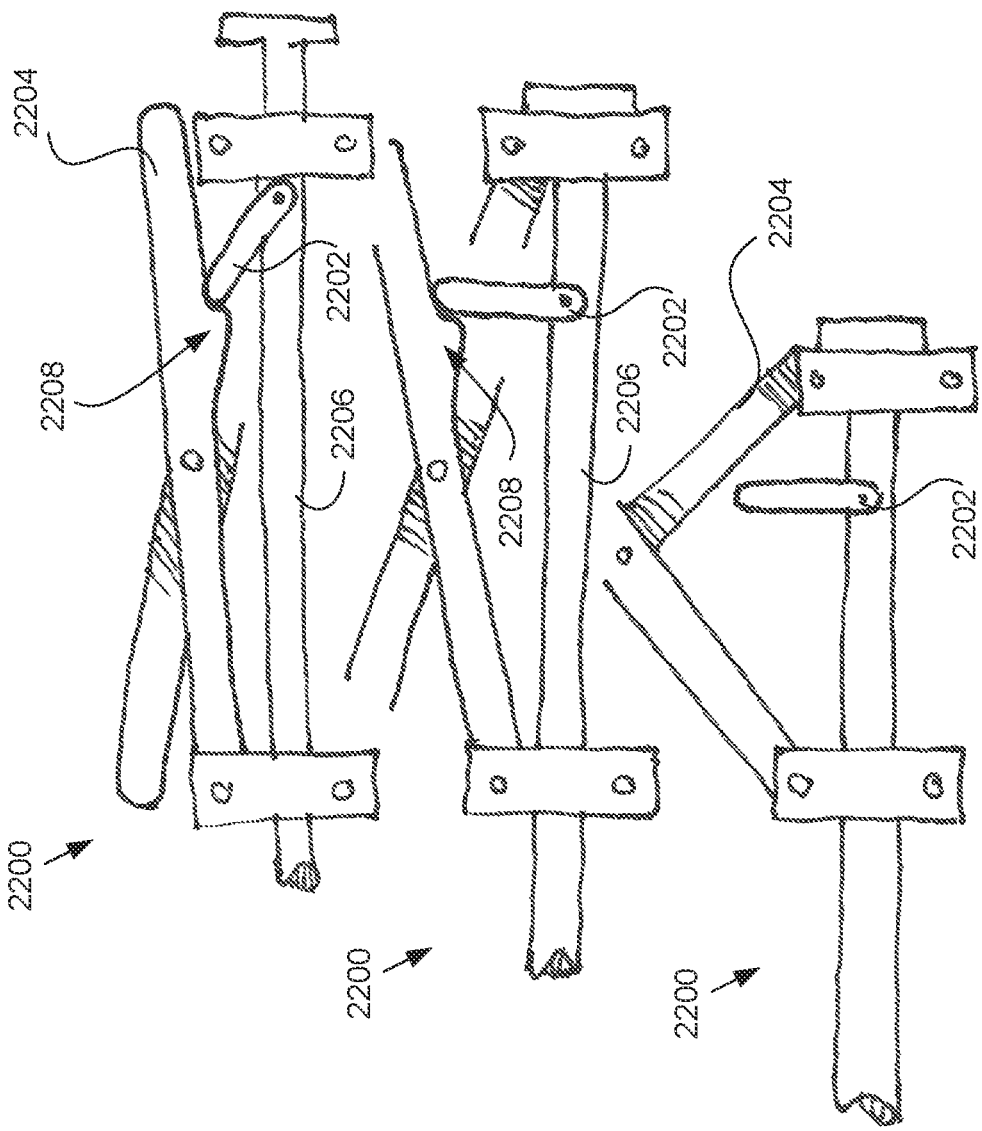

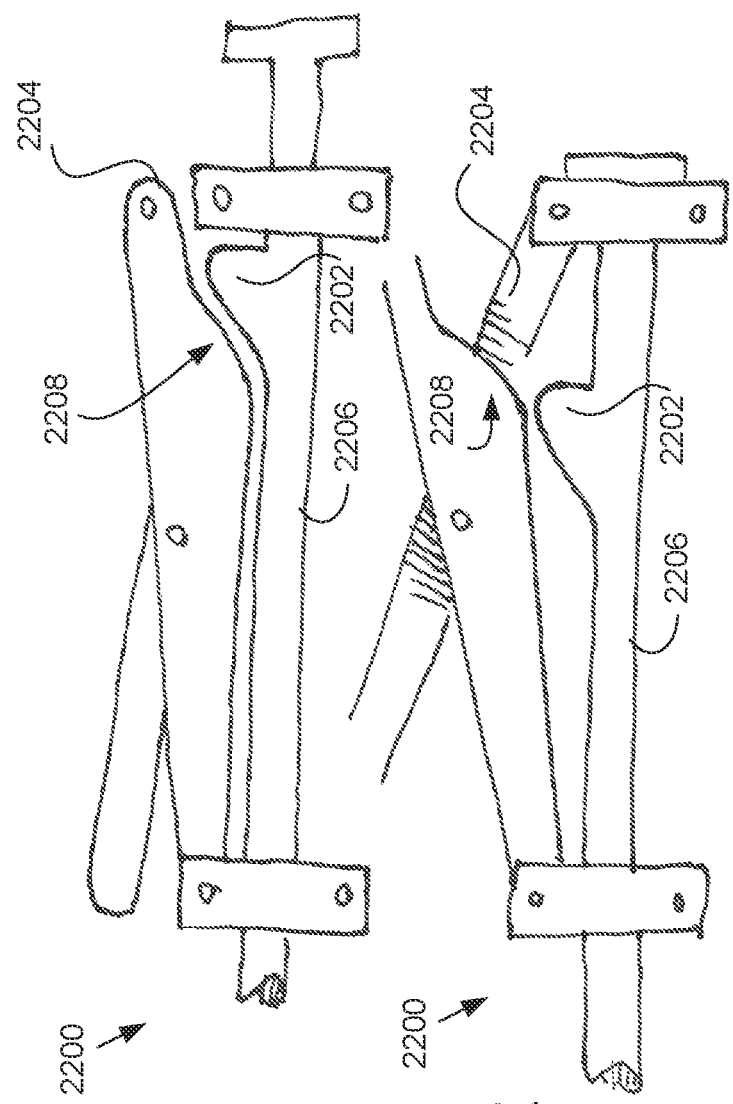

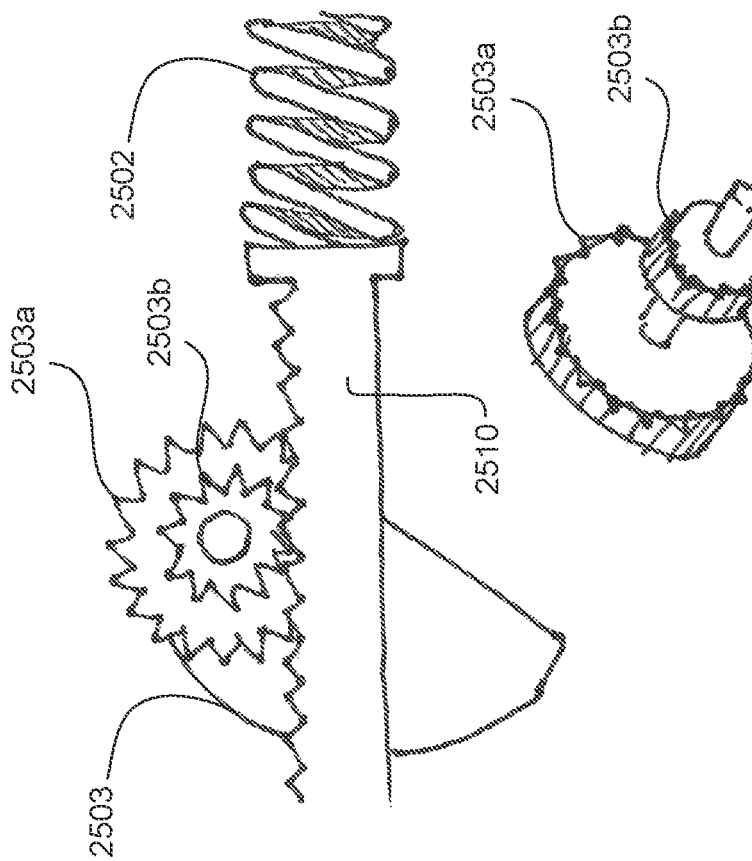
Fig. 25A
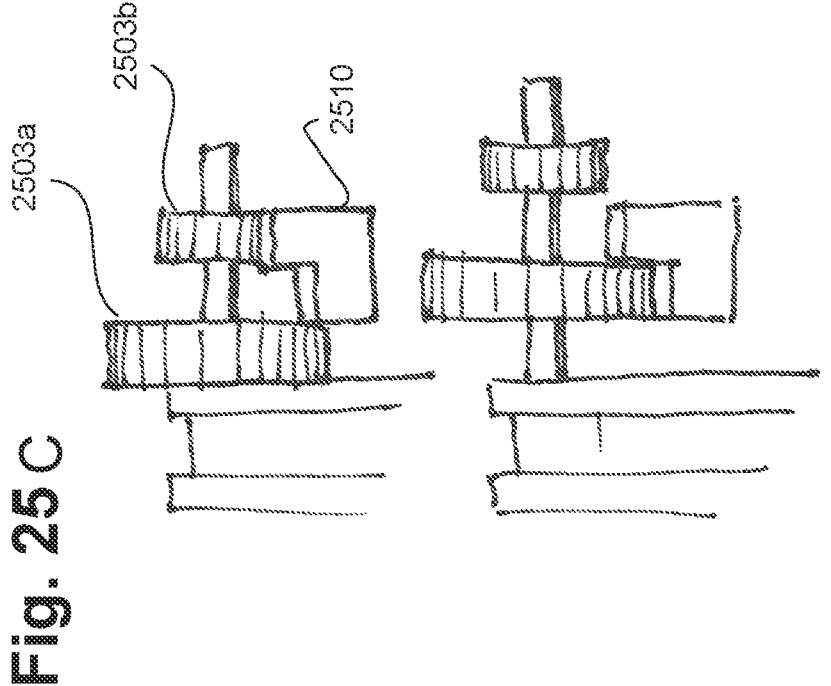
Fig. 25B
Fig. 25C

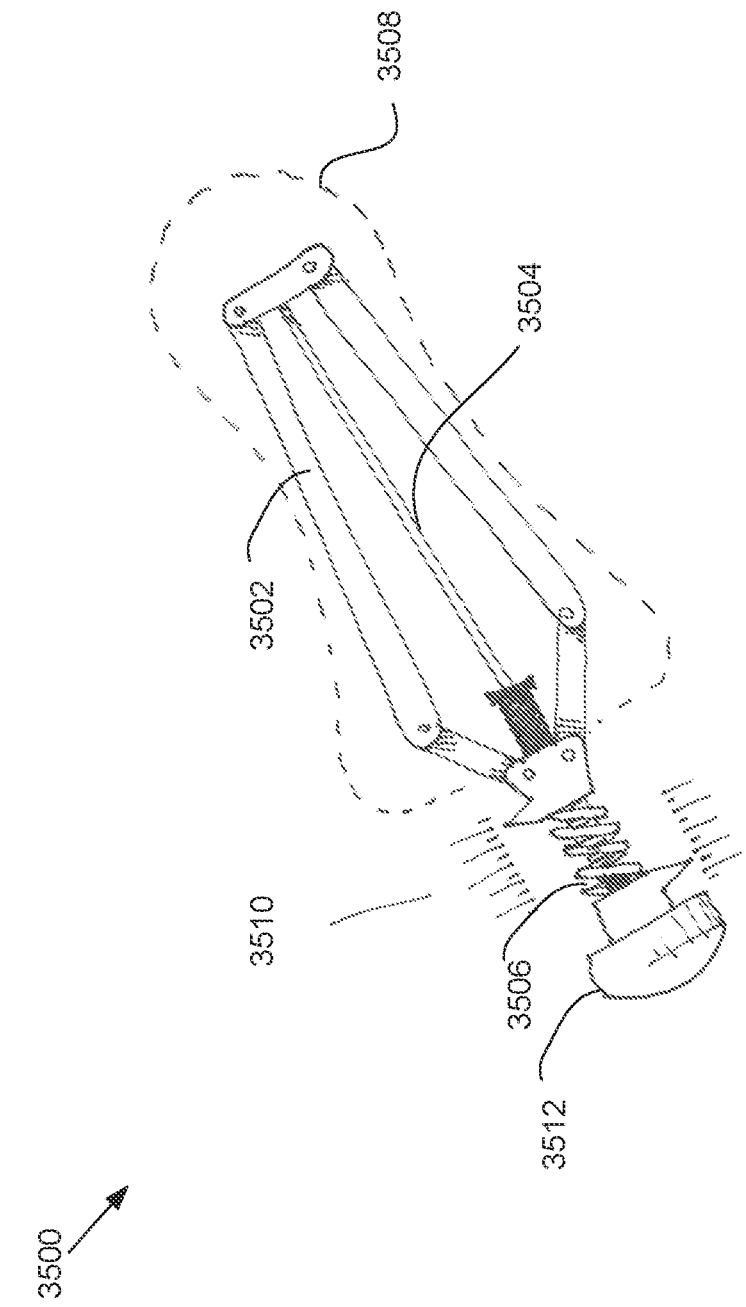

METHODS AND APPARATUS FOR PREVENTING VAGINAL LACERATIONS DURING CHILDBIRTH

CROSS REFERENCE TO RELATED APPLICATIONS

This application is a continuation of U.S. patent application Ser. No. 15/050,287, filed Feb. 22, 2016, now U.S. Patent Application Publication No. 2016/0166282, which is a continuation of U.S. application Ser. No. 13/876,920, filed Jun. 14, 2013, now U.S. Patent Application Publication No. 2013/0253376, which is a national phase of International Application No. PCT/US2011/032324, filed Apr. 13, 2011, which application is a continuation-in-part of International Application No. PCT/US2010/052528, filed Oct. 13, 2010. These applications are herein incorporated by reference in their entirety.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD OF THE INVENTION

Devices and methods are described generally relating to preparing tissue for childbirth. More specifically, the devices and methods described herein are intended to prepare and dilate vaginal tissue during labor so as to prevent pelvic floor damage, and vaginal and perineal lacerations.

BACKGROUND OF THE INVENTION

Approximately 134 million women give birth worldwide each year, of whom 3.0 million give birth vaginally in the United States. Approximately 8 out of 10 women who give birth vaginally will experience some degree of vaginal tearing. In the U.S., roughly 1.2 million, or 40%, experience a spontaneous laceration or episiotomy (planned surgical cut for high risk patients) that requires surgical repair. Between 1.5% and 15% of lacerations are considered severe and require extended healing time and pain management, and can result in difficult reparative surgery and a considerable decrease in quality of life measurements. Additionally, 15-35% of women suffer damage to their pelvic floor muscles, where the muscles are being physically pulled off of the pelvic bone or over-stretched to the point where they become functionally impaired. The direct costs of treating perineal lacerations to the healthcare system is estimated to total over $650 million each year, with treatments aimed at future pelvic floor disorders even higher.

Specific risk factors for perineal lacerations during childbirth have been identified, leading to above-average incidence in patient populations. These risk factors include nulliparity (primigravidity, first pregnancy), short perineal body, instrumental delivery (forceps-assisted delivery, vacuum-assisted delivery), prolonged second stage of labor (>1 hour), epidural analgesia, intrapartum infant factors (birth weight over 4 kg, persistent occipitoposterior position, shoulder dystocia), episiotomy, mediolateral or midline, previous anal sphincter tear, maternal age >30, and Asian ethnicity. In addition to the risk factors listed above, perineal lacerations have been linked with a higher incidence of many pelvic floor disorders such as infection, incontinence and prolapse. In general, pregnancy and birth have been linked as a cause of many pelvic floor disorders. However, the exact physiologic mechanisms that lead to many of these disorders are under investigation. It is thought that damage to the pelvic floor musculature during childbirth may be one of the most significant causes of pelvic floor disorders.

During vaginal delivery, labor and delivery are clinically divided into three stages. The first stage begins with cervical effacement and is completed with full cervical dilation that will allow the passage of the fetus through the birth canal. The second stage is defined by the passage of the fetus through the birth canal, described as the Cardinal Movements of Labor. It begins with complete cervical effacement and dilation and ends in the delivery of the fetus. The third stage is comprised of the separation and expulsion of the placenta.

During the first phase of labor, the birth canal is functionally closed and maintained in proper position by a number of layers of muscular and connective tissues that collectively form the pelvic floor. During the second phase of labor, the presenting part of the fetal head descends into the birth canal and exerts direct pressure on the pelvic floor. The fetus passes through the birth canal by stretching the fibers of the levator ani muscle and connective tissues, drastically distending and damaging the pelvic floor musculature, and stretching the perineum into a thin membranous structure that often lacerates during the process of delivery.

Pelvic floor and perineal tissues dilate rapidly during the second phase of labor. The introitus, or opening of the vagina, for the average woman, has a baseline resting diameter of roughly 2.6 cm. During the first phase of labor, while the cervix is dilating, the vagina stays at this baseline diameter and only when the baby has passed through the cervix does this tissue dilate from 2.6 cm up to 10 cm, the average head diameter of a newborn baby. This 3.8× expansion in diameter and approximately 15× expansion in area occurs in a matter of seconds to minutes.

Currently, there are no devices or tools that have proven to significantly reduce trauma to the pelvic floor during vaginal delivery, and there are no other devices that can be used to isolate the variables associated with pelvic floor disorders resulting from childbirth. No effective treatments exist to assist a woman in preconditioning the tissues of the vagina and perineum prior to and during labor.

Historically, gourds of increasing size have been used in Africa in an attempt to prepare the tissue for labor. Today, there are techniques such as perineal massage, hot compresses and "hands-on" delivery that can be performed in the hospital and have anecdotally showed promise, but none of these have been proven to be effective in the clinical trial setting.

One device previously introduced with the goal of pre-stretching tissue to prevent lacerations is called the Epi-No. The Epi-No is a small balloon that was intended to be used at home by the pregnant woman, 1-3 months before the baby was due. The goal was to inflate the balloon up to approximately 5 cm, at which time the woman would then practice pushing out the device. A problem with such a balloon-style dilator is that it can change in shape and size during expansion, which can result in poor stability of the device in the vagina and inability to accurately gauge and control the amount of dilation.

Vaginismus is a condition that causes involuntary tightness of the vagina during intercourse, caused by involuntary contractions of the pelvic floor muscles surrounding the vagina. Vaginismus can be painful, thereby preventing enjoyment of intercourse. Vaginal dilators combined with appropriate exercises have helped some women overcome these involuntary muscle contractions.

SUMMARY OF THE INVENTION

A vaginal dilation device is provided comprising a handle, a plurality of arms coupled to the handle, each arm having a pad disposed thereon that is shaped and configured to conform to a vagina, an expansion mechanism coupled to the arms and configured to move the arms and the pads radially outwards from the device, and a force sensor disposed on the device and configured to measure a force applied against the pads.

In some embodiments, each of the plurality of arms comprises a scissor-like assembly coupled to each of the pads. The expansion mechanism can be coupled to a central rod which is coupled to the handle and the arms, wherein axial movement of the central rod changes a distance of the pads from the central rod.

In one embodiment, actuation of the expansion mechanism is configured to move the central rod proximally towards the handle to move the arms and pads radially outwards from the central rod.

In some embodiments, the pads are arranged in a substantially parallel configuration as the arms and pads move radially outwards.

In some embodiments, the vaginal dilation device further comprises a closed configuration wherein the pads are arranged circumferentially around the central rod, and an expanded configuration wherein the pads are extended away from the central rod and away from adjacent pads. In one embodiment, an outer diameter of the pads in the closed configuration is less than 4 cm. In another embodiment, an outer diameter of the pads in the expanded configuration is approximately 8-10 cm.

In one embodiment, the vaginal dilation device further comprises a quick-release mechanism configured to quickly reduce an outer diameter of the device. In some embodiments, the device further comprises an actuation mechanism disposed on the handle that is configured to engage the quick-release mechanism. In another embodiment, the device further comprises a bump-release disposed on a distal portion of the device that is configured to engage the quick-release mechanism. In some embodiments, the bump-release is configured to be engaged by a baby entering a vaginal canal.

In some embodiments, a center of mass of the vaginal dilation device shifts forward under the pads as the device is expanded from the closed configuration to the expanded configuration.

In one embodiment, the vaginal dilation device further comprises a diameter sensor configured to indicate a dilation diameter of the vagina.

In some embodiments, the vaginal dilation device further comprises a controller coupled to the expansion mechanism and the force sensor, the controller configured to automatically move the arms and the pads radially outwards based on the force measured by the force sensor. For example, in some embodiments, the force sensor can measure a force applied by the pads, and the controller can automatically expand or contract the device based on the measured force. The controller can automatically increase the applied force if the measured force is too low, or can automatically decrease the applied force if the measured force is too high (e.g., the applied force is above a force threshold).

In some embodiments, the controller is configured to automatically move the arms and the pads radially outwards to apply a constant force to the vagina with the pads. In some embodiments, the vaginal dilation device further comprises a motor coupled to the central rod and a controller coupled to the force sensor and the motor, the controller configured to automatically move the central rod axially, and the arms and the pads radially outwards, based on the force measured by the force sensor. In some embodiments, the device further comprises a controller coupled to the expansion mechanism and the force sensor, the controller configured to automatically move the arms and the pads radially outwards until the force measured by the force sensor exceeds a force threshold.

In other embodiments, the controller is configured to automatically move the central rod axially to apply a constant force with the pads.

In some embodiments, the expansion mechanism is configured to automatically move the arms and the pads of the device radially outwards at a constant force. In some embodiments, the expansion mechanism comprises a spring coupled to the central rod, wherein the spring pushes against the central rod with a constant force to move the arms and the pads radially outwards from the central rod. In one embodiment, the constant force of the spring is user adjustable.

In some embodiments, a force applied by the spring to the dilation device can be adjusted. In other embodiments, the spring can be an adjustable clock spring. In some embodiments, a pivot point of the spring can be adjusted.

Some embodiments of the vaginal dilation device further comprise an expandable sheath disposed over the pads. Other embodiments further comprise a working channel disposed on or in the device.

In some embodiments of the vaginal dilation device, the force sensor comprises a plurality of force sensors disposed on the pads. In other embodiments, the force sensor comprises a plurality of force sensors disposed under the pads. In other embodiments, the force sensor comprises a plurality of force sensors disposed on the plurality of arms.

Some embodiments of the vaginal dilation device further comprise a clutching mechanism configured to prevent over-expansion of the pads. Other embodiments further comprise an automatic oscillation mechanism configured to prevent pressure necrosis.

In one embodiment of the vaginal dilation device, none of the pads contact a urethra or any nerve bundles positioned along an anterior portion of the vagina of the patient when the pads move radially outwards from the device. In other embodiments, none of the pads contact a perineum of the patient when the pads move radially outwards from the device.

In some embodiments, the expansion mechanism is remotely coupled to the arms via a flexible assembly.

In some embodiments, the vaginal dilation device further comprises a cam coupled to the expansion mechanism to linearize a force needed to expand the device from a closed configuration to an expanded configuration. In one embodiment, the cam is a ratcheted cam. In another embodiment, the cam is a geared cam mechanism with multiple gears. In some embodiments, a lever or bump mechanism can be utilized to linearize the force needed to expand the device from the closed configuration to the expanded configuration.

In some embodiments, the expansion mechanism can comprise a stent or yurt-like device. In other embodiments, the expansion mechanism can comprise a living hinge structure.

Another vaginal dilation device is provided, comprising, a handle, a plurality of arms coupled to the handle, each arm having a pad disposed thereon that is shaped and configured to conform to a vagina, and an expansion mechanism coupled to the arms and configured to move the arms and the pads radially outwards from the device at a constant force.

In some embodiments, each of the plurality of arms comprises a scissor-like assembly coupled to each of the pads. The expansion mechanism can be coupled to a central rod which is coupled to the handle and the arms, wherein axial movement of the central rod changes a distance of the pads from the central rod.

In one embodiment, actuation of the expansion mechanism is configured to move the central rod proximally towards the handle to move the arms and pads radially outwards from the central rod.

In some embodiments, the pads are arranged in a substantially parallel configuration as the arms and pads move radially outwards.

In some embodiments, the vaginal dilation device further comprises a closed configuration wherein the pads are arranged circumferentially around the central rod, and an expanded configuration wherein the pads are extended away from the central rod and away from adjacent pads. In one embodiment, an outer diameter of the pads in the closed configuration is less than 4 cm. In another embodiment, an outer diameter of the pads in the expanded configuration is approximately 8-10 cm.

In one embodiment, the vaginal dilation device further comprises a quick-release mechanism configured to quickly reduce an outer diameter of the device. In some embodiments, the device further comprises an actuation mechanism disposed on the handle that is configured to engage the quick-release mechanism. In another embodiment, the device further comprises a bump-release disposed on a distal portion of the device that is configured to engage the quick-release mechanism. In some embodiments, the bump-release is configured to be engaged by a baby entering a vaginal canal.

In some embodiments, a center of mass of the vaginal dilation device shifts forward under the pads as the device is expanded from the closed configuration to the expanded configuration.

In one embodiment, the vaginal dilation device further comprises a diameter sensor configured to indicate a dilation diameter of the vagina.

In some embodiments, the vaginal dilation device further comprises a controller coupled to the expansion mechanism and the force sensor, the controller configured to automatically move the arms and the pads radially outwards based on the force measured by the force sensor. For example, in some embodiments, the force sensor can measure a force applied by the pads, and the controller can automatically expand or contract the device based on the measured force. The controller can automatically increase the applied force if the measured force is too low, or can automatically decrease the applied force if the measured force is too high (e.g., the applied force is above or below a desired constant force threshold).

In some embodiments, the controller is configured to automatically move the arms and the pads radially outwards to apply a constant force to the vagina with the pads. In some embodiments, the vaginal dilation device further comprises a motor coupled to the central rod and a controller coupled to the force sensor and the motor, the controller configured to automatically move the central rod axially, and the arms and the pads radially outwards, based on the force measured by the force sensor. In some embodiments, the device further comprises a controller coupled to the expansion mechanism and the force sensor, the controller configured to automatically move the arms and the pads radially outwards to maintain the force applied by the device at the constant force. In other embodiments, the controller is configured to automatically move the central rod axially to apply a constant force with the pads.

In some embodiments, the expansion mechanism is configured to automatically move the arms and the pads of the device radially outwards at a constant force. In some embodiments, the expansion mechanism comprises a spring coupled to the central rod, wherein the spring pushes against the central rod with a constant force to move the arms and the pads radially outwards from the central rod. In one embodiment, the constant force of the spring is user adjustable.

Some embodiments of the vaginal dilation device further comprise an expandable sheath disposed over the pads. Other embodiments further comprise a working channel disposed on or in the device.

In some embodiments of the vaginal dilation device, the force sensor comprises a plurality of force sensors disposed on the pads. In other embodiments, the force sensor comprises a plurality of force sensors disposed under the pads. In other embodiments, the force sensor comprises a plurality of force sensors disposed on the plurality of arms.

Some embodiments of the vaginal dilation device further comprise a clutching mechanism configured to prevent over-expansion of the pads. Other embodiments further comprise an automatic oscillation mechanism configured to prevent pressure necrosis.

In one embodiment of the vaginal dilation device, none of the pads contact a urethra or any nerve bundles positioned along an anterior portion of the vagina of the patient when the pads move radially outwards from the device. In other embodiments, none of the pads contact a perineum of the patient when the pads move radially outwards from the device.

In some embodiments, the expansion mechanism is remotely coupled to the arms via a flexible assembly.

In some embodiments, the expansion mechanism is configured to move the arms and the pads radially outwards from the device at the constant force for a preset period of time. In some embodiments, the preset period of time comprises 5-10 minutes. In other embodiments, the preset period of time comprises 5-60 minutes. In additional embodiments, the preset period of time comprises less than 2 hours.

In another embodiment, a vaginal dilation device is provided, comprising a handle, a plurality of arms coupled to the handle, each arm having a pad disposed thereon that is shaped and configured to conform to a vagina, an expansion mechanism coupled to the arms and configured to move the arms and the pads radially outwards from the device, and a diameter sensor disposed on the device and configured to measure a diameter of the device.

In some embodiments, each of the plurality of arms comprises a scissor-like assembly coupled to each of the pads. The expansion mechanism can be coupled to a central rod which is coupled to the handle and the arms, wherein axial movement of the central rod changes a distance of the pads from the central rod.

In one embodiment, actuation of the expansion mechanism is configured to move the central rod proximally towards the handle to move the arms and pads radially outwards from the central rod.

In some embodiments, the pads are arranged in a substantially parallel configuration as the arms and pads move radially outwards.

In some embodiments, the vaginal dilation device further comprises a closed configuration wherein the pads are arranged circumferentially around the central rod, and an expanded configuration wherein the pads are extended away from the central rod and away from adjacent pads. In one embodiment, an outer diameter of the pads in the closed configuration is less than 4 cm. In another embodiment, an outer diameter of the pads in the expanded configuration is approximately 8-10 cm.

In one embodiment, the vaginal dilation device further comprises a quick-release mechanism configured to quickly reduce an outer diameter of the device. In some embodiments, the device further comprises an actuation mechanism disposed on the handle that is configured to engage the quick-release mechanism. In another embodiment, the device further comprises a bump-release disposed on a distal portion of the device that is configured to engage the quick-release mechanism. In some embodiments, the bump-release is configured to be engaged by a baby entering a vaginal canal.

In some embodiments, a center of mass of the vaginal dilation device shifts forward under the pads as the device is expanded from the closed configuration to the expanded configuration.

In some embodiments, the vaginal dilation device further comprises a controller coupled to the expansion mechanism and the diameter sensor, the controller configured to automatically move the arms and the pads radially outwards based on the diameter measured by the diameter sensor. For example, in some embodiments, the diameter sensor can measure a diameter of the device, and the controller can automatically expand or contract the device based on the measured diameter. The controller can automatically increase the diameter if the measured diameter is too low, or can automatically decrease the diameter if the measured diameter is too high.

In some embodiments, the vaginal dilation device further comprises a motor coupled to the central rod and a controller coupled to the diameter sensor and the motor, the controller configured to automatically move the central rod axially, and the arms and the pads radially outwards at a constant rate of dilation. In some embodiments, the device further comprises a controller coupled to the expansion mechanism and the diameter sensor, the controller configured to automatically move the arms and the pads radially outwards based on the diameter measured by the diameter sensor.

Some embodiments of the vaginal dilation device further comprise an expandable sheath disposed over the pads. Other embodiments further comprise a working channel disposed on or in the device.

Some embodiments of the vaginal dilation device further comprise a clutching mechanism configured to prevent over-expansion of the pads. Other embodiments further comprise an automatic oscillation mechanism configured to prevent pressure necrosis.

In one embodiment of the vaginal dilation device, none of the pads contact a urethra or any nerve bundles positioned along an anterior portion of the vagina of the patient when the pads move radially outwards from the device. In other embodiments, none of the pads contact a perineum of the patient when the pads move radially outwards from the device.

In some embodiments, the expansion mechanism is remotely coupled to the arms via a flexible assembly.

In some embodiments, the constant rate of dilation is user adjustable.

In some embodiments, the vaginal dilation device further comprises a timer configured to alert a user to increase the diameter of the device.

In one embodiment, the expansion mechanism comprises a trigger assembly configured to expand the device by a preset dilation increment with a single actuation of the trigger assembly. In some embodiments, the preset dilation increment is user adjustable.

A method of dilating a vagina during labor is provided, comprising inserting a vaginal dilation device into the vagina, measuring a force applied by the vaginal dilation device to the vagina, and dilating the vagina with the vaginal dilation device.

In some embodiments, the method further comprises pausing dilation of the vagina with the vaginal dilation device when the force applied by the vaginal dilation device to the vagina increases to a first force threshold. In one embodiment, the method further comprises resuming dilation of the vagina when the force applied by the vaginal dilation device to the vagina decreases to a second force threshold. In another embodiment, the resuming dilation step further comprises resuming dilation of the vagina with the vaginal dilation device until the force applied by the vaginal dilation device increases to the first force threshold. In one embodiment, the resuming dilation step further comprises resuming dilation of the vagina with the vaginal dilation device until the force applied by the vaginal dilation device increases to a third force threshold, the third force threshold being larger than the first force threshold. In one embodiment, the first force threshold is larger than the second force threshold. In another embodiment, the first force threshold is less than 8 lbs. of force.

In some embodiments of the method, the inserting step further comprises inserting the vaginal dilation device into the vagina during a first phase of labor. The method can further comprise removing the vaginal dilation device from the vagina prior to a second phase of labor.

In some embodiments, the measuring a force step further comprises measuring the force with the vaginal dilation device.

In one embodiment, the method further comprises measuring a diameter of the vagina with the vaginal dilation device. The method can further comprise dilating the vagina with the vaginal dilation device based on the measured diameter.

In some embodiments, the dilating step further comprises dilating the vagina at a constant force with the vaginal dilation device. In other embodiments, the dilating step further comprises manually dilating the vagina with the vaginal dilation device. In an additional embodiment, the dilating step further comprises automatically dilating the vagina with the vaginal dilation device.

In another embodiment, the dilating step further comprises dilating the vagina with the vaginal dilation device at a location remote from the patient.

Another method of dilating a vagina during labor is provided, comprising inserting a vaginal dilation device into the vagina, and applying a constant force to the vagina with the vaginal dilation device to dilate the vagina. In some embodiments, the constant force is less than 8 lbs. of force. In other embodiments, the constant force is adjustable.

In some embodiments of the method, the inserting step further comprises inserting the vaginal dilation device into the vagina during a first phase of labor. In other embodiments, the method comprises removing the vaginal dilation device from the vagina prior to a second phase of labor. In additional embodiments, the method comprises removing the vaginal dilation device from the vagina when the vagina is dilated to a diameter of approximately 8-10 cm.

In some embodiments, the method comprises measuring a diameter of the vagina with the vaginal dilation device.

In another embodiment, the applying step further comprises automatically applying a constant force to the vagina with the vaginal dilation device to dilate the vagina. In one embodiment, the applying step further comprises automatically applying the constant force to the vagina with a constant force spring disposed in the vaginal dilation device. In another embodiment, the applying step further comprises automatically applying the constant force to the vagina with an automated controller and a motor coupled to the vaginal dilation device. In another embodiment, the applying step further comprises applying the constant force to the vagina with the vaginal dilation device for a preset period of time to dilate the vagina. In some embodiments, the preset period of time comprises less than 5 minutes. In other embodiments, the preset period of time comprises 5-10 minutes. In additional embodiments, the preset period of time comprises 5-60 minutes. In yet another embodiment, the preset period of time comprises less than 2 hours.

Another embodiment of the method comprises measuring a force applied by the vaginal dilation device to the vagina.

A method of preventing tissue damage during childbirth is provided, comprising inserting a vaginal dilation device into a patient's vagina during a first phase of labor, and dilating the patient's vagina with the vaginal dilation device.

In some embodiments, the method further comprises removing the vaginal dilation device from the patient's vagina prior to a second phase of labor.

In another embodiment, the dilating step comprises dilating the patient's vagina to approximately 7-10 cm with the vaginal dilation device.

A vaginal exercise device is provided, comprising a handle, a plurality of arms coupled to the handle, each arm having a pad disposed thereon that is shaped and configured to conform to a vagina, an expansion mechanism coupled to the arms and configured to move the arms and the pads radially outwards from the device at a user-specified force, and a force sensor disposed on the device and configured to measure a force applied by the vagina against the pads.

In some embodiments, axial movement of the expansion mechanism engages a sloping interior cam surface of the pads to expand the pads radially outward. In other embodiments, the expansion mechanism comprises a cone shaped object.

In some embodiments, the expansion mechanism comprises a plurality of living hinges.

In one embodiment, the expansion mechanism is coupled to a central rod which is coupled to the handle and the arms, wherein axial movement of the central rod changes a distance of the pads from the central rod.

In some embodiments, actuation of the expansion mechanism is configured to move the central rod proximally towards the handle to move the arms and pads radially outwards from the central rod.

In some embodiments, the pads are arranged in a substantially parallel configuration as the arms and pads move radially outwards.

One embodiment further comprises a closed configuration wherein the pads are arranged circumferentially around the central rod, and an expanded configuration wherein the pads are extended away from the central rod and away from adjacent pads. In one embodiment, an outer diameter of the pads in the closed configuration is less than 1 cm. In another embodiment, an outer diameter of the pads in the expanded configuration is approximately 2-4 cm.

Some embodiments further comprise a diameter sensor configured to indicate a dilation diameter of the vagina.

In one embodiment, the expansion mechanism is configured to automatically move the arms and the pads of the device radially outwards at the user-specified force. In another embodiment, the expansion mechanism comprises a spring coupled to the central rod, wherein the spring pushes against the central rod with a constant force to move the arms and the pads radially outwards from the central rod.

In some embodiments, none of the pads contact a urethra or any nerve bundles positioned along an anterior portion of the vagina of the patient when the pads move radially outwards from the device.

In another embodiment, none of the pads contact a perineum of the patient when the pads move radially outwards from the device.

In one embodiment, the expansion mechanism is remotely coupled to the arms via a flexible assembly.

A cervical dilation device is provided, comprising a handle, a plurality of arms coupled to the handle, each arm having a pad disposed thereon that is shaped and configured to conform to a cervix of a patient, an expansion mechanism coupled to the arms and configured to move the arms and the pads radially outwards from the device at a constant force, a force sensor disposed on the device and configured to measure a force applied against the pads, and an extension mechanism coupling the handle to the arms and the expansion mechanism, the extension mechanism sized and configured to allow the arms to access the cervix while the handle remains outside of the patient.

In some embodiments, the expansion mechanism is coupled to a central rod which is coupled to the handle and the arms, wherein axial movement of the central rod changes a distance of the pads from the central rod.

In one embodiment, actuation of the expansion mechanism is configured to move the central rod proximally towards the handle to move the arms and pads radially outwards from the central rod.

In some embodiment, the pads are arranged in a substantially parallel configuration as the arms and pads move radially outwards.

Another embodiment of the device comprises a closed configuration wherein the pads are arranged circumferentially around the central rod, and an expanded configuration wherein the pads are extended away from the central rod and away from adjacent pads. In some embodiments, an outer diameter of the pads in the closed configuration is less than 1 cm. In other embodiments, an outer diameter of the pads in the expanded configuration is approximately 2-10 cm.

Some embodiments of the device further include a diameter sensor configured to indicate a dilation diameter of the cervix.

In some embodiments, the expansion mechanism is configured to automatically move the arms and the pads of the device radially outwards at the constant force.

In other embodiments, the expansion mechanism comprises a spring coupled to the central rod, wherein the spring pushes against the central rod with the constant force to move the arms and the pads radially outwards from the central rod.

In some embodiments, each of the plurality of arms comprises a scissor-like assembly coupled to each of the pads.

Some embodiments further comprise a quick-release mechanism configured to quickly reduce an outer diameter of the device.

In one embodiment, the device further comprises an actuation mechanism disposed on the handle that is configured to engage the quick-release.

Some embodiments further comprise a controller coupled to the expansion mechanism and the force sensor, the controller configured to automatically move the arms and the pads radially outwards based on the force measured by the force sensor.

In one embodiment, the controller is configured to automatically move the arms and the pads radially outwards to apply the constant force with the pads.

Some embodiments further comprise a motor coupled to the central rod and a controller coupled to the force sensor and the motor, the controller configured to automatically move the central rod axially, and the arms and the pads radially outwards, based on the force measured by the force sensor.

In some embodiments, the controller is configured to automatically move the central rod axially to apply the constant force with the pads.

Some embodiments further comprise a controller coupled to the expansion mechanism and the force sensor, the controller configured to automatically move the arms and the pads radially outwards until the force measured by the force sensor exceeds a force threshold.

A method of dilating a cervix during labor is provided, comprising inserting a cervical dilation device into the cervix, measuring a force applied by the cervical dilation device to the cervix, dilating the cervix with the cervical dilation device, and pausing dilation of the cervix with the cervical dilation device when the force applied by the cervical dilation device to the cervix increases to a first force threshold.

In some embodiments the method comprises resuming dilation of the cervix when the force applied by the cervical dilation device to the cervix decreases to a second force threshold. In one embodiment, the resuming dilation step further comprises resuming dilation of the cervix with the cervical dilation device until the force applied by the cervical dilation device increases to the first force threshold. In another embodiment, the resuming dilation step further comprises resuming dilation of the cervix with the cervical dilation device until the force applied by the cervical dilation device increases to a third force threshold, the third force threshold being larger than the first force threshold.

In some embodiments, the first force threshold is larger than the second force threshold. In other embodiments, the first force threshold is less than 8 lbs. of force.

In some embodiments, the inserting step further comprises inserting the cervical dilation device into the cervix during a first phase of labor.

Some embodiments further comprise removing the cervical dilation device from the cervix prior to a second phase of labor.

In one embodiment, the measuring a force step further comprises measuring the force with the cervical dilation device.

Other embodiments of the method further comprise measuring a diameter of the cervix with the vaginal dilation device.

Other embodiments of the method further comprise dilating the cervix with the cervical dilation device based on the measured diameter.

In some embodiments, the dilating step further comprises dilating the cervix at a constant force with the cervical dilation device. In additional embodiments, the dilating step further comprises manually dilating the cervix with the cervical dilation device. In another embodiment, the dilating step further comprises automatically dilating the cervix with the cervical dilation device. In another embodiment, the dilating step further comprises dilating the cervix with the cervical dilation device at a location remote from the patient.

A method of exercising pelvic muscles surrounding a vagina is provided, comprising inserting a vaginal exercise device into the vagina, applying a constant force to the vagina with the vaginal exercise device, and measuring the force applied by the vagina to the vaginal exercise device.

In some embodiments, the constant force is less than 8 lbs. of force. In other embodiments, the constant force is user adjustable.

In some embodiments, the vaginal exercise device expands outwardly to a diameter of 2-4 cm.

In one embodiment, the applying step further comprises automatically applying a constant force to the vagina with the vaginal exercise device.

In another embodiment, the applying step further comprises automatically applying the constant force to the vagina with a constant force spring disposed in the vaginal exercise device.

In one embodiment, the applying step further comprises automatically applying the constant force to the vagina with an automated controller and a motor coupled to the vaginal exercise device.

In some embodiments, the applying step further comprises applying the constant force to the vagina with the vaginal exercise device for a preset period of time to exercise the pelvic muscles surrounding the vagina.

In some embodiments, the preset period of time comprises less than 5 minutes, 5-10 minutes, 5-60 minutes, or less than 2 hours.

BRIEF DESCRIPTION OF THE DRAWINGS

FIGS. 1A-1D illustrate some embodiments of a vaginal dilation device.

FIG. 2 is one view of a vaginal dilation device in an expanded configuration.

FIGS. 7A-7B show embodiments of a vaginal dilation device with a protective sheath.

FIGS. 20A-20D illustrate another embodiment of a vaginal dilation device.

FIGS. 21A-21C illustrate another embodiment of a vaginal dilation device.

FIGS. 22A-22E illustrate another embodiment of a vaginal dilation device.

FIGS. 25A-25C illustrate another embodiment of a vaginal dilation device.

FIG. 35 illustrates another embodiment of a vaginal dilation device or a vaginal exercise device.

DETAILED DESCRIPTION OF THE INVENTION

Figure 1D:
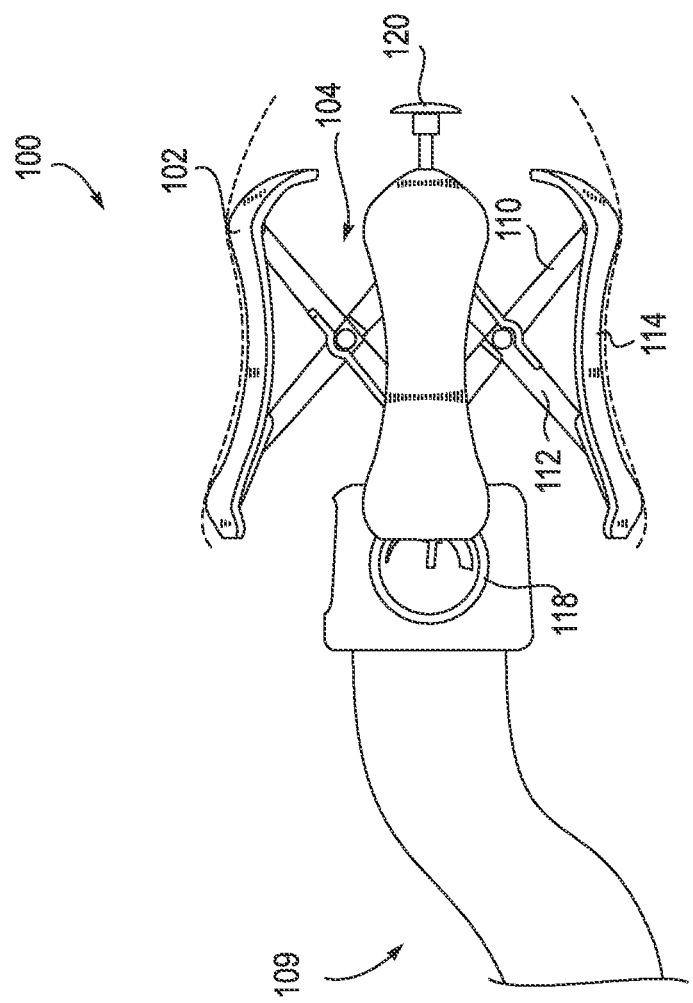

The devices and methods described herein are intended to prepare and dilate vaginal tissue during labor so as to prevent pelvic floor damage, and vaginal and perineal lacerations. Some embodiments of the device can stretch the perineal tissue until the diameter of the vaginal introitus has reached a target diameter of approximately 10 cm, roughly the size of the fetal head. In some embodiments, the device is a mechanical dilator that penetrates the first 3-4 cm of the vagina, the introitus, and gradually expands the vagina from a resting diameter of 2-3 cm to a fully expanded diameter equal to the size of the delivering fetus, approximately 10 cm. Expansion can be controlled either manually or via an automatic actuation system, and the device can be quickly collapsed and removed if needed.

The devices described herein can be inserted during the first phase of labor and removed just prior to the second phase of labor, allowing the rest of the birthing process to proceed as normal. The device is intended to be used prior to the second phase of labor to prevent a baby from contacting the device during delivery. Depending on how long it takes to achieve full vaginal dilation to approximately 10 cm, the device can be inserted early during the first phase of labor with only very minor amounts of dilation. The dilation diameter target of 10 cm means that the device should be used in a hospital under the supervision of trained obstetricians and nurses. The device can be used without any anesthesia, or under local anesthetic. The tissue can also be prepared after administering an epidural, which would eliminate any pain or discomfort the device may cause. Local anesthesia can also be placed on the tissue contacting surfaces of the device to minimize pain.

FIGS. 1A-1C illustrate one embodiment of a vaginal dilation device 100. Vaginal dilation device 100 can include rigid or semi-rigid pads 102, arms 104, handle 106, and expansion mechanism 108. In the embodiment of FIGS. 1A-1C, device 100 includes four sets of pads 102 and arms 104. In other embodiments, any number of pads and arms can be used. For example, one embodiment comprises as few as 2 or 3 sets of pads and arms, and other embodiments can include more than four sets of pads and arms, such as 5, 6, 7, or even 8 or more sets of pads and arms. The sets of pads and arms can be arranged symmetrically or asymmetrically around a central axis of the device.

The pads 102 can be coupled to arms 104, which can be coupled to a central rod (not shown) that extends along a longitudinal axis of the device, through the handle 106, and is coupled to expansion mechanism 108. The tissue contacting pads 102 can be designed to maintain stability through all dilation diameters. In some embodiments, the pads can have a saddle shape that maintains a constant waist size and pitch when expanded. These pads can be overmolded with a very compliant biocompatible elastomeric material to help evenly distribute force against the tissue and prevent trauma. Additional pad shapes and designs will be discussed below.

In the embodiment shown in FIGS. 1A-1C, arms 104 comprise a scissor-like assembly, and include shafts 110 and 112 which rotate around pivot 114. Shafts 110 and 112 can be coupled to the pads and to the central rod. In FIGS. 1A-1C, expansion mechanism 108 comprises a mechanical knob configured to expand the arms of the vaginal dilation device. Manual rotation of the knob can cause the knob to move away from the handle and the central rod to move proximally into the handle, allowing shafts 110 and 112 to rotate around pivot 114 and push pads 102 radially outwards from the central rod of the device. Since the arms 104 comprise a scissor-like assembly, the pads 102 can remain parallel to the device and to one another during expansion, which maintains the orientation of the pads to the tissue stable during dilation. Additionally, maintaining the pads in a parallel orientation can help keep the device in place in the tissue while maximizing force distribution along the pads.

Rotation of the knob in the opposite direction can cause the central rod to move distally, causing the scissor-like assembly to collapse and moving the pads inwards towards the central rod. In some embodiments, the sets of arms 104 can have varying radii of curvature, which can expand the arms out at different rates if desired.

Although most embodiments described herein show the arms as a scissor-like assembly, it should be understood that other methods and apparatus for expanding the pads can be used. For example, the arms can be singular arms attached to the pads (e.g., similar to a speculum).

The vaginal dilation device can be sized, shaped, and configured to penetrate approximately the first third, or 3-4 cm, of the vagina, and to gradually expand the vaginal introitus from a resting diameter of approximately 2 cm to a fully dilated diameter of approximately 10 cm. The vaginal dilation device 100 can be configured to expand from a compact, closed configuration, as shown in FIG. 1A, to an expanded configuration, as shown in FIG. 1C. When the device is in the closed configuration, the pads can be seamlessly closed against each adjacent pad so as to form a solid shape (e.g., circle, oval, etc.).

When the device is in the closed configuration of FIG. 1A, pads 102 can be configured to rest against each adjacent pad so as to reduce the outer diameter of the device. In some embodiments, the diameter of the pads in the closed configuration can be less than 4 cm. In one embodiment, the outer diameter of the pads in the closed configuration is approximately 2-4 cm. In other embodiments, the pads do not rest against adjacent pads in the closed configuration, but this can result in the minimum outer diameter of the pads being larger, or alternatively, in the individual pads 102 having a smaller surface area, which may lead to patient discomfort during tissue dilation.

As the device dilates to the expanded configuration, as shown in FIGS. 1B-1C, pads 102 and arms 104 move radially outwards from the device, causing the pads to separate from one another. In some embodiments, the maximum diameter of the pads in the expanded configuration can be approximately 10 cm. In one embodiment, the maximum outer diameter of the pads in the expanded configuration is approximately 8-12 cm.

The vaginal dilation device 100 is specifically designed to promote compactness, effective dilation, and good tissue contact during expansion. As the device expands from the closed configuration to the expanded configuration, the center of mass of the device can move under the pads, as shown by arrow 116 in FIG. 1C, which helps keep the device in place without rotating and falling out of the vagina.

The vaginal dilation device 100 can further comprise indicator(s) or gauge(s) 118. In the embodiment of FIGS. 1A-1C, the gauge 118 is disposed on handle 106, however the gauge can be disposed in any location on the device, or even remotely from the device such as on a display monitor. In some embodiments, the gauge gives the user an indication of the diameter of the pads 102. A user, such as a physician, can then use the gauge to know the exact amount of tissue dilation. Gauge 118 can comprise a simple binary readout (showing the diameter is above or below some threshold to continue dilating), or can have a scale showing the actual diameter of the device, for example.

In other embodiments, the vaginal dilation device 100 includes force sensors (not shown) configured to measure a force applied by the pads against tissue, or alternatively, to measure a force applied against the pads, and the gauge 118 can give the user an indication of the measured force. The force sensors can be strain gauges, whetstone bridges, piezoelectric crystals, hydraulic/pneumatic load cells, elastic devices, or any other force sensor or force transducer known in the art. Gauge 118 can comprise a simple binary readout (showing the force is above or below some threshold to continue dilating), or can have a scale showing the actual force being applied to the tissue, for example. In additional embodiments, gauge 118 can indicate both a diameter of the pads and a force sensed by the pads. Alternatively, the vaginal dilation device can comprise multiple gauges, including diameter gauges and force gauges.

The dilation device may additionally include a quick-release mechanism configured to collapse the device from the expanded configuration to the closed configuration. The quick-release mechanism can comprise bump-release 120 and quick-release lever 122. Additional details regarding the quick-release mechanism will be discussed below.

FIG. 1D illustrates one embodiment similar to the device of FIGS. 1A-1C, however the expansion mechanism 108 of FIG. 1D remotely coupled to the rest of the device (e.g., remotely coupled to the central shaft, arms, and pads) via flexible assembly or flexible tube 109. The device of FIG. 1D operates in the same manner as the device described above in FIGS. 1A-1C, however the remote expansion mechanism allows a user to expand/dilate the device from a distance away from the patient. This is advantageous because during labor, the patient's legs are typically covered with sheets or a blanket, so the remote expansion mechanism allows for actuation of the device without having to remove the covers, protecting the patient's privacy.

In other embodiments, the device can include an alarm or alert mechanism, such as a visual alert (e.g., a light, or a warning indicator on a display) or an audible alert (e.g., a buzzer or an alarm sound) to indicate to a user that the device is applying too much, or too little force to the vagina. The alert mechanism can also include a timer configured to alert the user (e.g., by an audible or visual signal) when to dilate the device.

FIG. 2 is a cutaway view of a vaginal dilation device 200 in an expanded configuration, showing the operation of a diameter gauge 218 according to one embodiment. Vaginal dilation device 200 is a variation of the vaginal dilation device 100 described above. FIG. 2 illustrates the interior of handle 206, including expansion mechanism 208, diameter gauge 218, central rod 224, spring 226, and nut 228. Rotation of the expansion mechanism can cause central rod 224 to move proximally into the handle, which in turn causes nut 228 to move proximally to compress spring 226. As the spring is compressed, it can apply pressure to the diameter gauge 218, causing it to move according to the diameter of the pads 202 and arms 204 as they expand radially outwards. Since the outward movement of a scissor-like mechanism as shown in FIG. 2 is not linear, the vaginal dilation device may further include a diameter gauge amplifying mechanism 230, such as an additional spring coupled to a rotating portion of the gauge, to provide a more linear read out for the diameter gauge 218.

The tip of gauge 218 may extend out through a window in the handle 206. In some embodiments, the handle can include indicator marks or diameter measurements along the length of the window to provide an indication to the user of the diameter of the device. The marks can be colors, such as green, yellow, red, to give an indication of the amount of dilation, or can be accurate diameter measurements, such as marks indicating 0-10 cm of dilation. Other marks or indicators can also be used, as long as they give an approximate or accurate read-out of the diameter of the device as it expands.

Figure 3A:
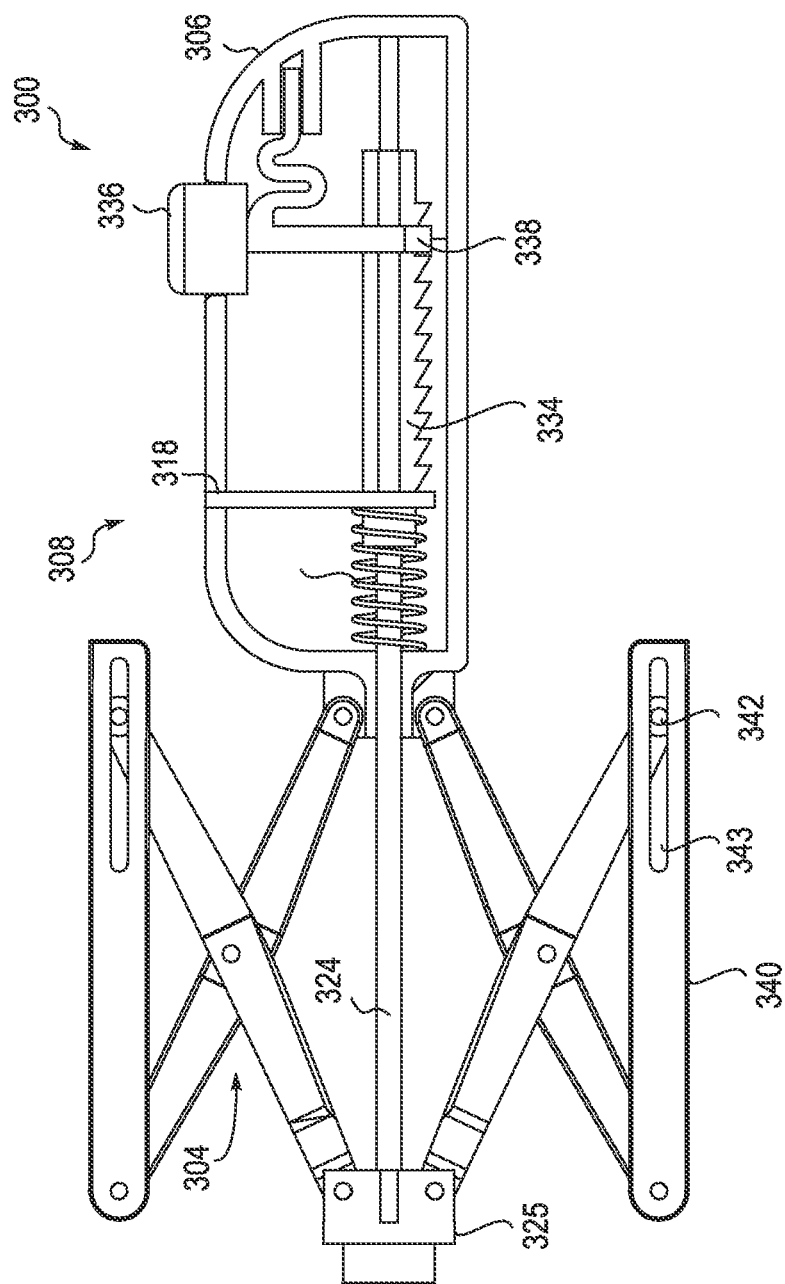
FIGS. 3A-3D show cross-sectional views of a vaginal dilation device.
Figure 3B:
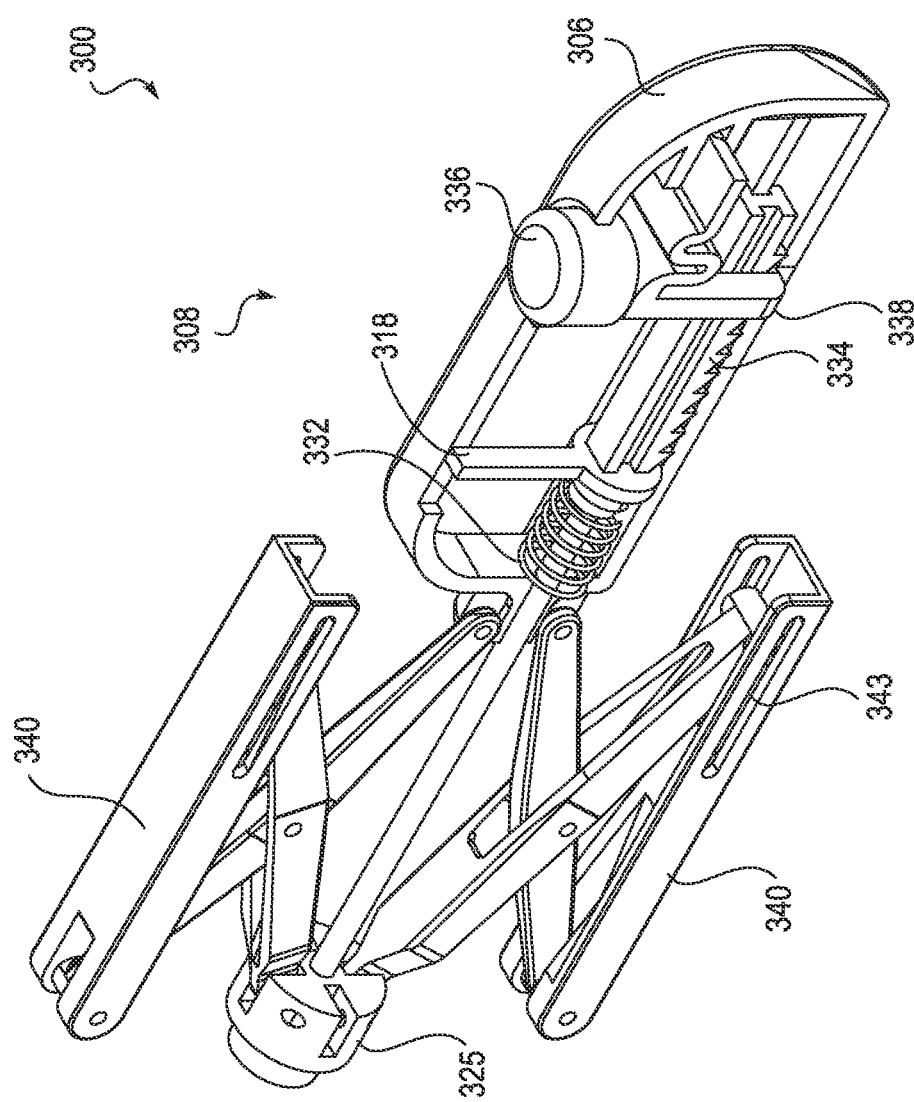

FIGS. 3A-3B show cross-sectional views of another embodiment of a vaginal dilation device 300. The vaginal dilation devices described above in FIGS. 1 and 2 were directed to a device actuated by manual rotation of a knob. However, the vaginal dilation device 300 of FIGS. 3A-3B can include an actuation mechanism that comprises a constant force device 332 and a button 336 to actuate expansion of the device. In the embodiment shown in FIGS. 3A-3B, the constant force device 332 comprises a spring. However, any similar stored energy device can be used in place of the spring, including a pump or a piston, an elastic band, or gears, for example.

The vaginal dilation device of FIGS. 3A-3B can include arms 304, handle 306, gauge 318, central rod 324, shuttle assembly 325, rack assembly 334, button 336, and pad supports 340. In the embodiment of FIGS. 3A-3B, button 336 can be coupled to a pin 338. Pad supports are configured to support pads, such as pads 102 or 202 described above. It should be understood that button 336 could be any other form of actuating device, such as a lever, a trigger, or a rotating dial, for example.

Referring still to FIGS. 3A-3B, the operation of vaginal dilation device 300 will now be described. As shown, arms 304 can comprise a scissor-like assembly. A proximal portion of the scissor-like assemblies can be coupled to the handle 306, and a distal portion of the scissor-like assemblies can be coupled to shuttle assembly 325. Central rod 324 can extend from shuttle assembly 325 along a longitudinal axis of the device into handle 306, terminating at rack assembly 334. Constant force device 332, such as a spring, can be disposed inside the handle around the central rod, compressed between an inner wall of the handle and the rack assembly. The rack assembly can comprise a plurality of gears or teeth, which can engage pin 338 of button 336.

When button 336 is depressed, pin 338 disengages rack assembly 334. Constant force device 332 (e.g., a spring) is then allowed to decompress and expand, thereby applying a constant force against the rack assembly and the central rod 324, and thus shuttle assembly 325, proximally towards handle 306. As the distance between shuttle assembly 325 and handle 306 decreases, the scissor-like assemblies expand, pushing pad supports and pads (not shown) radially outward from the device. It should also be understood that device 300 of FIGS. 3A-3B can comprise an actuation mechanism remotely coupled to the device (e.g., via a flexible tube as shown in FIG. 1D) so as to allow for expansion of the device from a location remote from or a distance away from the patient.

As the constant force device 332 pushes against rack assembly 334 and central rod 324, gauge 318 moves proximally with the rack assembly, giving the user an indication of the dilation diameter of the pads of the vaginal dilation device. Expansion of the device continues until the next tooth or gear in the rack assembly engages pin 338 of button 336. The teeth of rack assembly 334 can be spaced at specific increments of dilation, for example, spaced 1 cm apart along the desired range of dilation, such as from 1 cm to 10 cm. Once the rack assembly has re-engaged pin 338, the user can again depress button 336 to initiate the next interval of dilation. In some embodiments, the button can also remain in the pushed "on" position, which would allow the device to continue expanding and dilating tissue with a constant force. Similarly, in another embodiment, the rack assembly can include only a single tooth or gear, allowing the device to continue to expand at a constant force once the pin 338 has disengaged the single tooth.

Since the vaginal dilation device is configured to expand at a constant force, the amount of force applied by the device to tissue can be determined and controlled so as to maximize effectiveness of the device and prevent the device itself from causing tissue damage. The constant force can be set at a level to reduce the risk of causing trauma, yet be enough to successfully, controllably dilate the tissue. In another embodiment, the vaginal dilation device can include a clutching mechanism, such as another spring or a torque-wrench type mechanism to prevent over-expansion of the pads. The clutching mechanism can be configured to engage at a preset force threshold to prevent the device from applying a force higher than the force threshold to tissue. In other embodiments, the device can include an alarm or alert mechanism, such as a visual alert (e.g., a light, or a warning indicator on a display) or an audible alert (e.g., a buzzer or an alarm sound) to indicate to a user that the device is applying too much, or too little force to the vagina. The alert mechanism can also include a timer configured to alert the user (e.g., by an audible or visual signal) when to dilate the device.

As described above, the constant force device 332 can comprise any device configured to apply a constant force, such as a spring, a piston, or a pump. The constant force device can be configured to automatically apply a constant force of any desired amount from the pads of the device to tissue. In some embodiments, the constant force device can apply a constant force to tissue ranging from approximately less than 10 lbs. of force. In some embodiments where a spring is used as the constant force device, the spring coils can have a variable thickness in order to adjust for gains in mechanical advantage as the vaginal dilation device is expanded, thus keeping the force applied by the device to tissue as a constant.

FIGS. 3A-3B also illustrate the mechanisms that allow the pads and pad supports 340 to remain parallel as the device expands. Arms 304 can include a rotating pivot point 342 configured to slide in slot 343 as the device expands. Movement of the pivot point along the slot allows the pads to remain parallel to the central rod of the device during tissue dilation.

FIGS. 20A-20D illustrate another embodiment of a mechanism configured to allow pads 2002 to remain parallel as device 2000 expands. Referring to FIGS. 20A-20C, pads 2002 can connect to arms 2004 at pivot 2006. Spring 2008 can be configured to push against pads 2002. As the device 200 expands, the load against the pads increases, compressing the spring. The spring can be configured to provide enough force to overcome any initial load applied against the pads by the tissue. Thus, the spring can be chosen that has a rate to allow the pads to remain parallel as the device expands. FIG. 20D illustrates the device in an expanded configuration, with the springs 2008 pushing against pads 2002 to cause the pads to remain parallel. The device illustrated in FIGS. 20A-20D can be configured for use as a vaginal dilator device or as a vaginal exercise device.

Figure 3C:
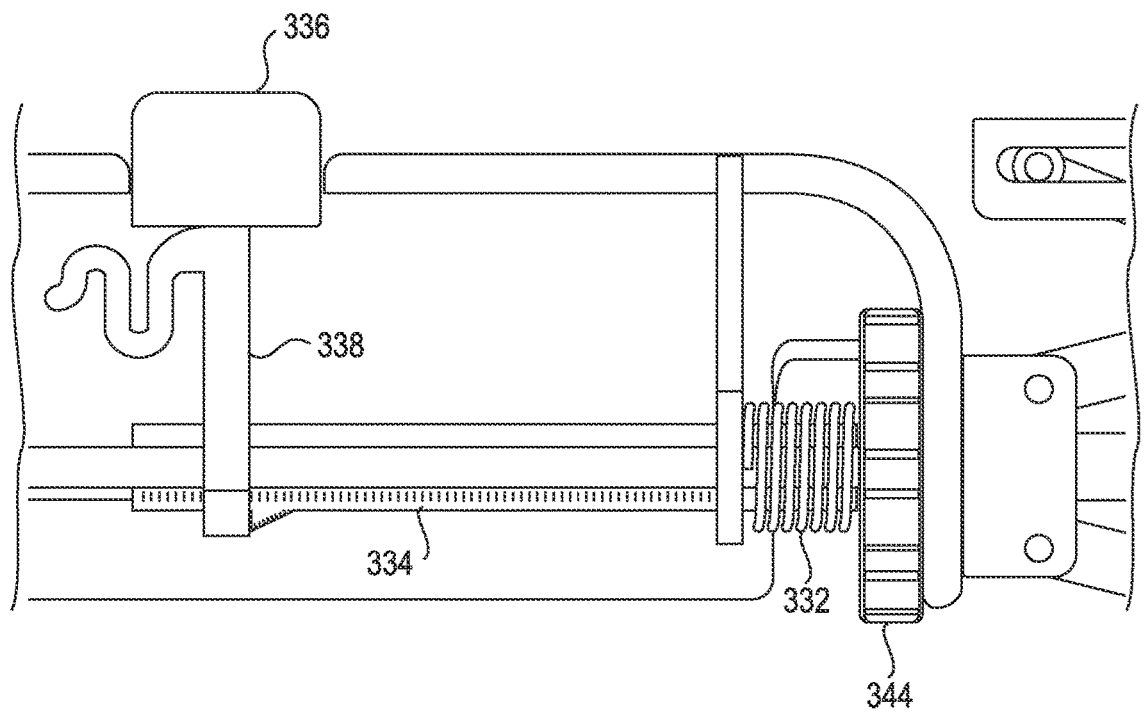
Figure 3D:
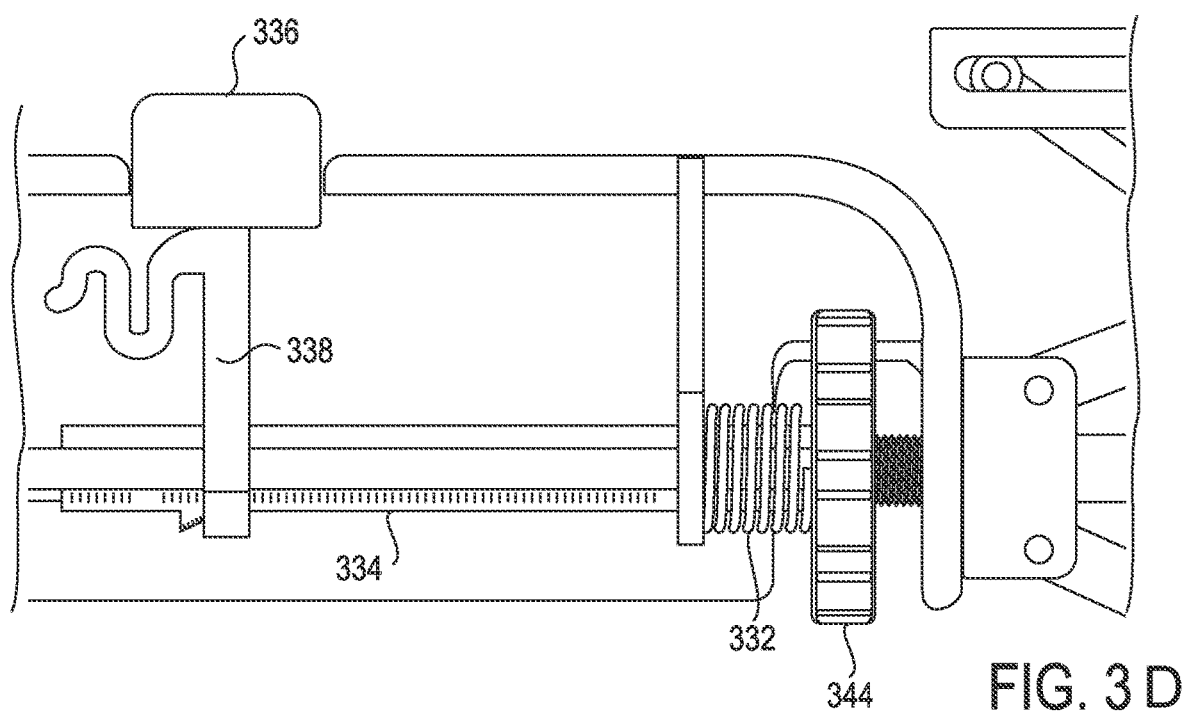

In another embodiment, as shown in FIGS. 3C-3D, the vaginal dilation device comprises a constant force mechanism 332, such as the spring described above, and further includes a force adjustment mechanism 344 configured to change the amount of force that the constant force mechanism, and thus the vaginal dilation device, applies to tissue. As shown in FIGS. 3C-3D, the force adjustment mechanism 344 can comprise a wheel or knob positioned adjacent to the spring. When the force adjustment mechanism is adjusted from a minimum position, as shown in FIG. 3C, to a tensioned position, as shown in FIG. 3D, the force adjustment mechanism compresses the spring, and adds force to which the spring will push back against the rack mechanism, thereby increasing the force the vaginal dilation device can apply to tissue.

In some embodiments, the vaginal dilation device of FIGS. 3A-3D can include a dampener (not shown), to limit any rapid dilation caused by the device. The dampener can be a piece of foam, a spring, or a piston mechanism at the proximal end of the device, for example.

FIG. 21A-21C illustrate another embodiment of a vaginal dilation device 2100, including a cam 2102 configured to normalize the force curve of arms 2104 as they expand. Certain features of a vaginal dilation device not illustrated in FIGS. 21A-21C can be found in other illustrations of vaginal devices described herein, specifically FIGS. 1-3. Referring to FIG. 21A, vaginal dilation device 2100 can include arms 2104 (e.g., a scissor-like mechanism) coupled to central rod 2106 and shuttle assembly 2108. Cam 2102 can be coupled to the central rod, and can be in contact with wheel 2110. The device can further include a constant force device (not shown in FIG. 21A) similar in function and operation to constant force device 332 described above in FIGS. 3A-3D. As the constant force device pulls central rod 2106 and shuttle assembly 2108 in the direction indicated by arrow 2112 to expand device 2100, cam 2102 pivots along wheel 2110. In a vaginal dilation device utilizing a scissor-like expansion mechanism, the device requires more force to expand at the beginning of expansion than at the end of expansion (e.g., the vaginal dilation device requires more force to expand from 1 cm to 2 cm than it does to expand from 9 cm to 10 cm). This is because a scissor-like expansion mechanism gains mechanical advantage during expansion. The cam 2102 of FIGS. 21A-21C can be configured to linearize the force of vaginal dilation device 2100 during expansion. To do so, the cam 2102 can be designed to lose mechanical advantage at the same rate that the scissor-like arms 2104 gain mechanical advantage during expansion. For example, in one embodiment, a particular angular change in the cam 2102 can lead to a corresponding change in diameter of the pads and arms 2104 of the dilation device 2100.

FIG. 21B illustrates a cam 2102 comprising a diameter gauge 2114, wherein the diameter gauge is configured to display a diameter of the vaginal dilation device. FIG. 21C illustrates another embodiment of a cam 2102 including mechanical stops, rests, or detents to provide feedback during the expansion process. In one embodiment, shown in FIG. 21C, stops can be placed along the cam 2102 corresponding to a pre-set device diameter. Thus, in FIG. 21C, the stops are located at centimeter intervals ranging from 3 cm-10 cm (e.g., a stop is placed at positions on the cam corresponding to device expansion diameters of 3 cm, 4 cm, 5 cm . . . 10 cm). In some embodiments, the stops on cam 2102 can prevent the vaginal dilation device from overexpanding without input from a user.

FIGS. 22A-22E illustrate additional embodiments for overcoming low angle forces of a scissor-like expansion mechanism in a vaginal dilation device 2200. Certain features of a vaginal dilation device not illustrated in FIGS. 22A-22C can be found in other illustrations of vaginal devices described herein, specifically FIGS. 1-3. In the embodiment of FIGS. 22A-22C, lever 2202 can be pivotably coupled to central rod 2206, and the lever can be configured to engage a detent or bump 2208 on arm 2204. As the dilation device expands and central rod 2206 moves towards a proximal end of the device, lever 2202 provides additional mechanical advantage to arms 2204 because it is at a greater angle relative to the central rod than the arms of the device. FIG. 22B illustrates the lever 2202 fully expanded as the dilation device and arms 2204 continue to expand. Referring now to FIG. 22C, the arms 2204 of the dilation device have expanded beyond the point of lever 2202 engaging detent 2208, so that the lever floats freely and the arms are allowed to expand on their own. The lever can continue to float until the arms collapse back to a point at which the lever can once again engage the detent 2208.

FIGS. 22D-22E illustrate a similar concept to the device illustrated in FIGS. 22A-22C. Certain features of a vaginal dilation device not illustrated in FIGS. 22D-21E can be found in other illustrations of vaginal devices described herein, specifically FIGS. 1-3. In FIGS. 22D-22E, the central rod 2206 can include a detent or bump 2202 instead of a lever, and the detent 2202 can be configured to engage a corresponding detent or bump 2208 on the arms 2204. This interaction between the detents 2202 and 2208 provides additional mechanical advantage to arms 2204 during the initial stages of expansion. Once the arms are sufficiently expanded to the point where the detents are not contacting another, as shown in FIG. 22D, the scissor-like mechanism can continue to expand like normal.

Figure 23A:
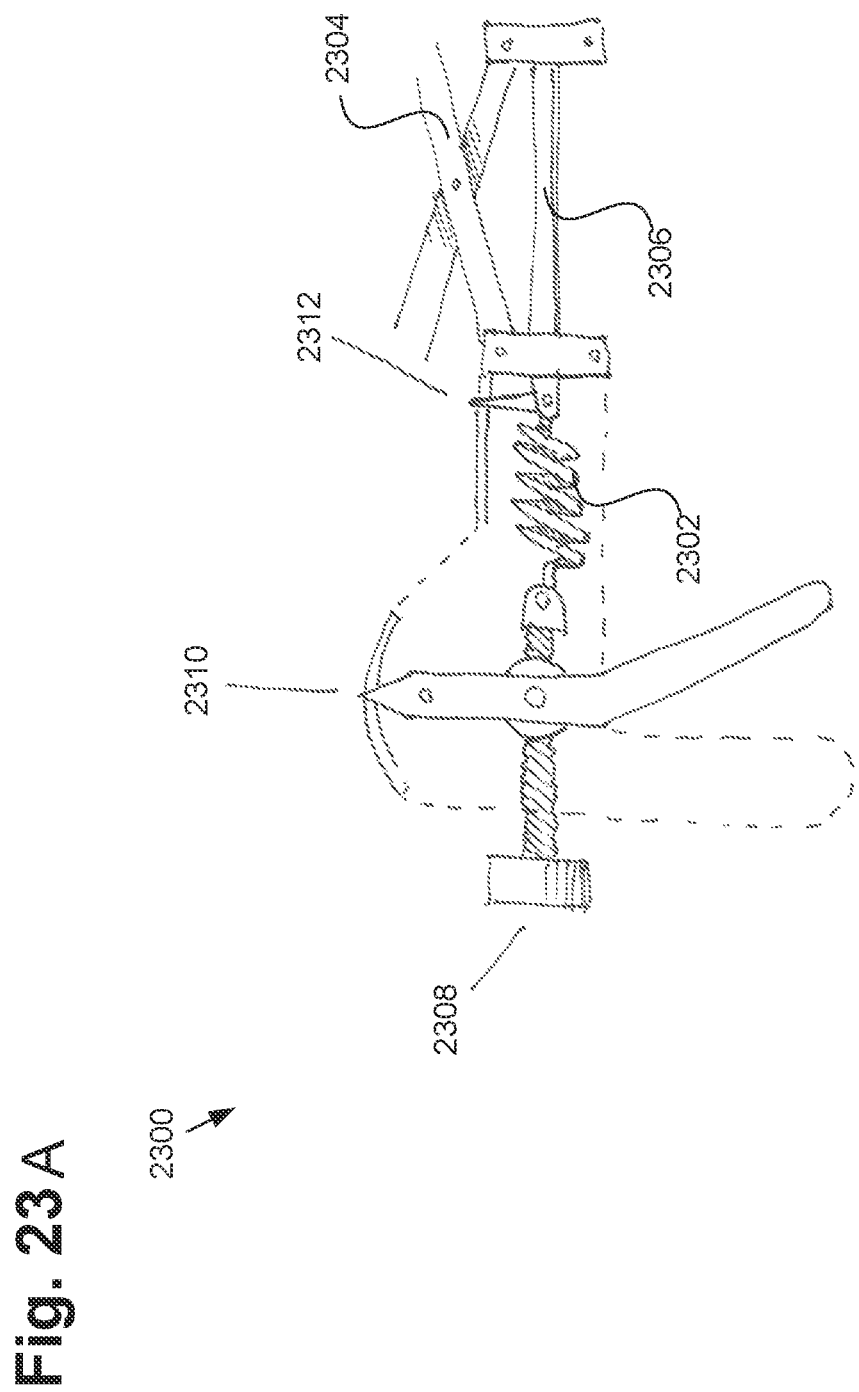
FIGS. 23A-23B illustrate another embodiment of a vaginal dilation device.
Figure 23B:
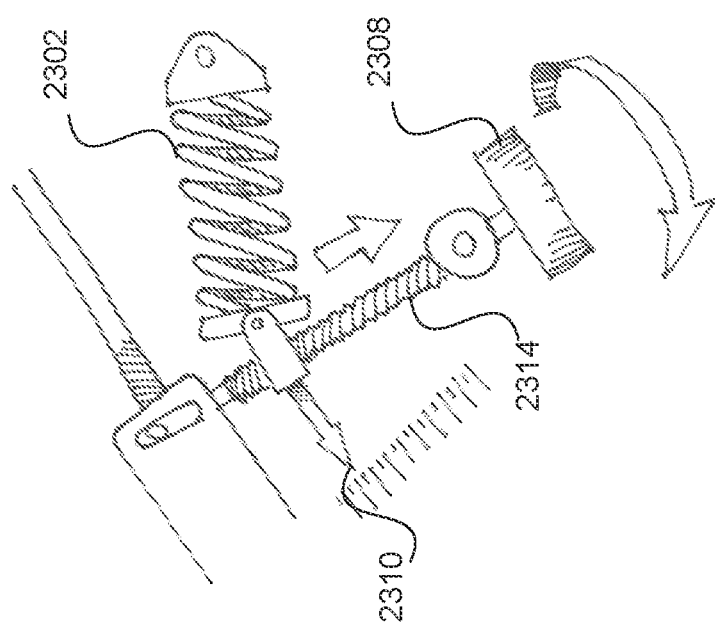

FIGS. 23A-B illustrate another embodiment of a vaginal dilation device 2300 comprising an adjustable force mechanism. Certain features of a vaginal dilation device not illustrated in FIGS. 23A-23B can be found in other illustrations of vaginal devices described herein, specifically FIGS. 1-3. Referring to FIG. 23A, dilation device 2300 comprises force mechanism 2302 (e.g., a spring), arms 2304, central rod 2306, force adjustment mechanism 2308, target diameter gauge 2310, and actual diameter gauge 2312. The device can operate in a manner similar to the device described herein, namely, the force mechanism 2302 pulls against central rod 2306, which causes arms 2304 to expand outward and increase the diameter of the device. In the embodiment shown in FIG. 23A, force adjustment mechanism 2308 can be used to change the compression of force mechanism 2302. In some embodiments, force mechanism 2308 is coupled to a target diameter gauge 2310, which is configured to display a target diameter of dilation based on the current compression setting of force mechanism 2302. Actual diameter gauge 2312 can be configured to display the actual dilation diameter of the device. For example, if the vaginal dilation device 2300 is inserted into a patient, and has achieved a maximum dilation for that particular force setting, a user can adjust the force setting of force mechanism 2302 with adjustment mechanism 2308 to increase or decrease the diameter of the device. The desired diameter can be dialed in according to target diameter gauge 2310, and the user can monitor the progress of the device with actual diameter gauge 2312.

FIG. 23B is another embodiment of an adjustable force mechanism for use with a vaginal dilation device. Certain features of a vaginal dilation device not illustrated in FIG. 23B can be found in other illustrations of vaginal devices described herein, specifically FIGS. 1-3. Instead of changing the compression of a force mechanism (e.g., a spring) as in the embodiment of FIG. 23A, in this embodiment, force mechanism 2302 can be translated up and down lever 2314 by rotating adjustment mechanism 2308. Adjusting the location of the force mechanism along the lever acts like changing the point of a fulcrum on a lever, which can adjust the amount of force the force mechanism applies to the device. Thus, a user can monitor the actual diameter gauge (not shown) and the force gauge 2310, and adjust the position of the force mechanism according to a desired diameter or force of the device.

Figure 24A:
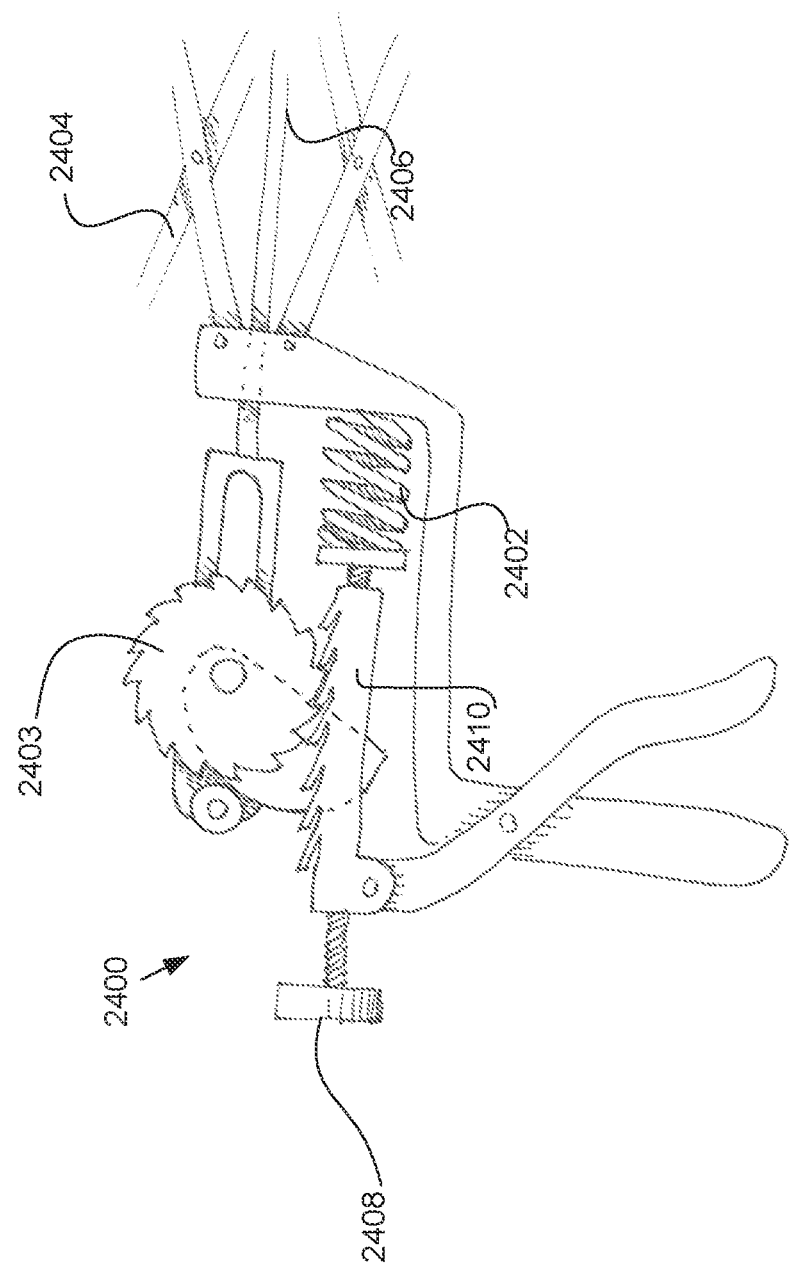
FIGS. 24A-24C illustrate another embodiment of a vaginal dilation device.
Figure 24B:
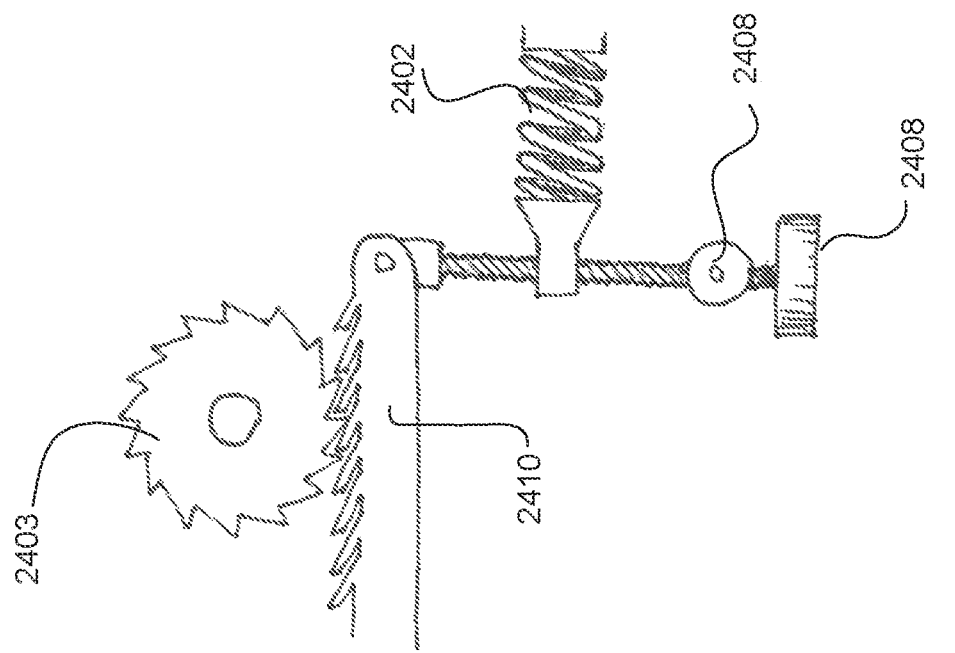
Figure 24C:
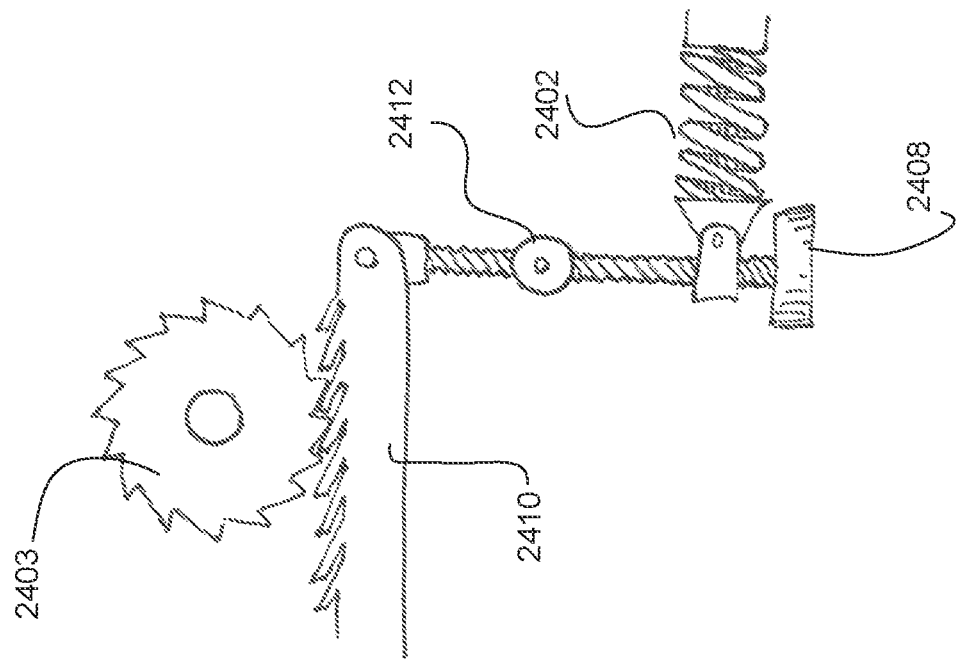

FIGS. 24A-24C illustrate another embodiment of a vaginal dilation device 2400, including a ratcheted cam 2403. Certain features of a vaginal dilation device not illustrated in FIGS. 24A-24C can be found in other illustrations of vaginal devices described herein, specifically FIGS. 1-3. Similar to the embodiments described above that employ a cam, the ratcheted cam of this embodiment can linearize the force needed to expand the device. In this embodiment, force mechanism 2402 can push against rack 2410, which engages ratcheted cam 2403. This causes central rode 2406 to move proximally towards the ratcheted cam, which expands arms 2404 and dilates the device outwardly. Force adjustment mechanism 2408 can be configured to change the compression of force mechanism 2402, as described above.

FIGS. 24B-C illustrate additional ways of adjusting the force applied by the device, similar to the embodiment described above in FIG. 23B. In FIG. 24B, force adjustment mechanism 2408 can be configured to adjust a pivot point 2412 of the device. The pivot point can then be connected to the central rod (not shown, but described above) to facilitate expansion of the device. In FIG. 24C, the pivot point 2412 is fixed, so the force adjustment mechanism 2408 is configured to adjust the position of the force mechanism 2402 relative to the pivot point (similar to the fulcrum embodiment described above in FIG. 23B).

FIGS. 25A-25C illustrate another embodiment of a vaginal dilation device comprising a ratcheted cam with multiple gears. Certain features of a vaginal dilation device not illustrated in FIGS. 25A-25C can be found in other illustrations of vaginal devices described herein, specifically FIGS. 1-3. Similar to the embodiment of FIGS. 24A-24C, force mechanism 2502 can be configured to apply pressure to rack 2510, which engages ratcheted cam 2510 of the device, causing scissor-like arms (not shown) to expand outwardly from a central rod of the device. In this embodiment, the ratcheted cam can include multiple gears, such as gears 2503a and 2503b having varying diameters. Referring to the side views of cam 2503 and rack 2510 in FIG. 25C, it can be seen that rack 2510 can include multiple levels configured to align with the various gears of the ratcheted cam. Using multiple gears allows a user to change the amount of force applied to the arms of the device. For example, smaller gear 2503b requires more force to expand the arms of the dilation device than larger gear 2503a. Engaging the different gears can be implemented in a number of ways. In one embodiment, the ratcheted cam 2503 can be pushed laterally (e.g., in the direction of arrow 2512) to change from smaller gear 2503b to larger gear 2503a. Although the embodiment of FIGS. 25A-25C illustrates only two gears, it should be understood that any number of gears can be used.

Figure 26A:
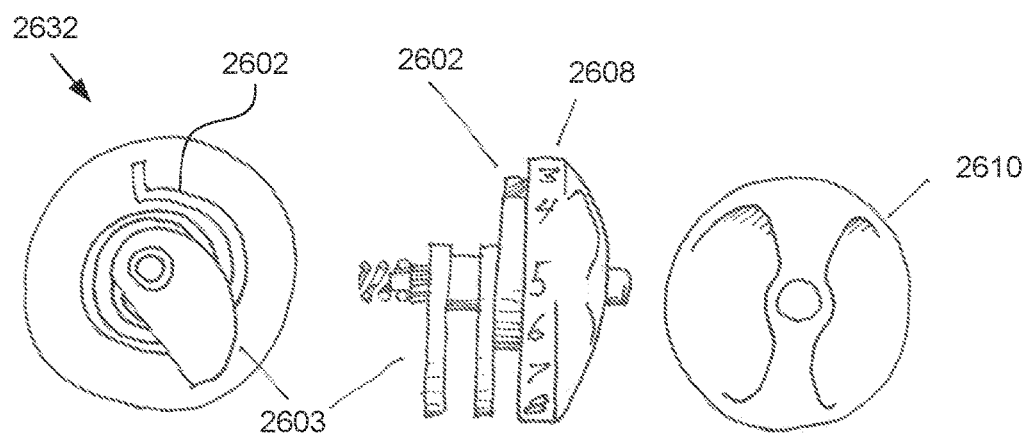
FIGS. 26A-26C illustrate another embodiment of a vaginal dilation device.
Figure 26B:
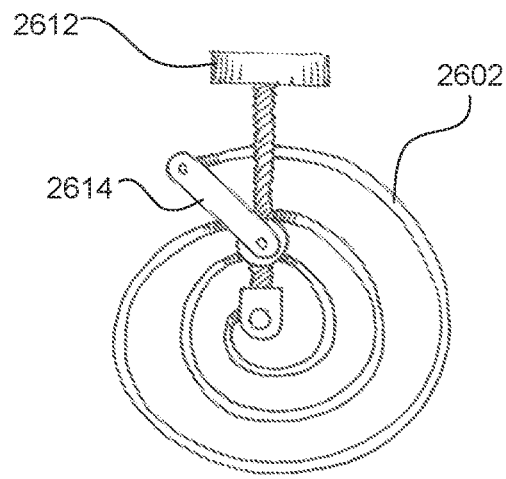
Figure 26C:
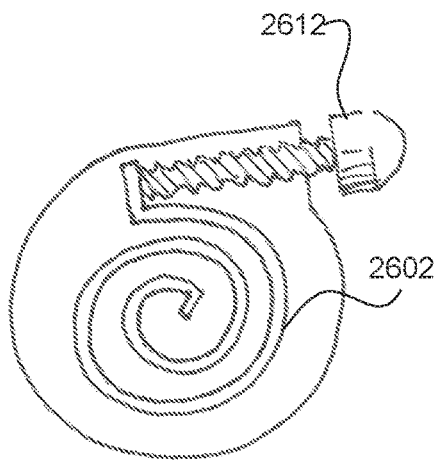

FIGS. 26A-26C illustrate various embodiments of a constant force spring that can be used in a vaginal dilation device. Certain features of a vaginal dilation device not illustrated in FIGS. 26A-26C can be found in other illustrations of vaginal devices described herein, specifically FIGS. 1-3. The constant force spring illustrated in FIGS. 26A-26C can be used, for example, as the constant force mechanism 332 of FIGS. 3C-3D above. FIG. 26A illustrates back, side, and front views, respectively, of a constant force mechanism 2632, comprising a cam 2603, a clock spring 2602, a target diameter gauge 2608, and a dial 2610. Ratchet features disposed on the dial (not shown) can prevent the dial from unwinding. The spring would then be configured to transmit force from the cam 2603 through a central rod (not shown, but similar in function to the central rods described above), which would then expand arms of the vaginal dilation device. The embodiment of FIG. 26A could also include an actual diameter gauge (not shown) in addition to the target diameter gauge.

FIGS. 26B-26C illustrate various embodiments for adjusting the force of the clock spring 2602 of FIG. 26A. In FIG. 26B, force adjustment mechanism 2612 can adjust a pivot point of lever 2614, which changes the compression of clock spring 2602. In FIG. 26C, force adjustment mechanism 2612 compresses the spring directly, causing an increase or decrease in the force applied by the spring to the cam.

Figure 27:
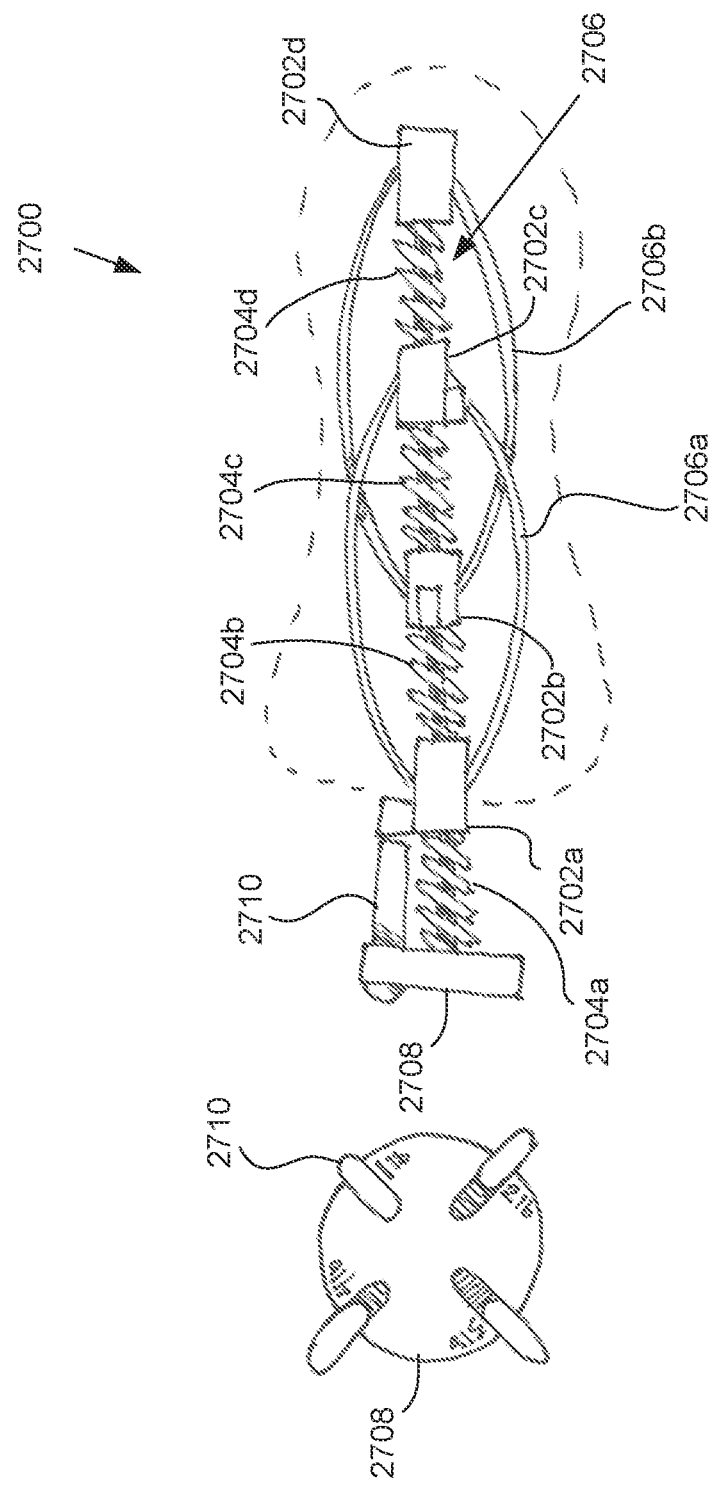
FIG. 27 illustrates another embodiment of a vaginal dilation device.

FIG. 27 illustrates another embodiment of a constant force vaginal dilation device 2700. In FIG. 27, the vaginal dilation device includes a series of cylinders 2702a-d slidably connected to central rod 2706. The cylinders can be separated by compression springs 2704a-d. Flexible arch features 2706a-b (e.g., leaf springs, living hinges) can also span from one cylinder to the next. When the system is compressed, the arches bend and the device expands in diameter. A dial feature 2708 can house a hard stop 2710 for each cylinder (only one hard stop is illustrated in FIG. 27). Engaging a particular hard stop on the dial locks out a corresponding spring(s). The force required to compress the system becomes greater with each spring that is locked out. As shown in the front view of dial 2708 in FIG. 27, the dial can include a number of user actuatable hard stops corresponding to various springs, and thus, various forces. For example, in one embodiment, the dial includes force settings of 1 lb., 2 lbs., 3 lbs., and 4 lbs., corresponding to actuating each of the hard stops 2710. It should be understood that other forces and number of hard stops/springs can be used in other embodiments.

Figure 28:
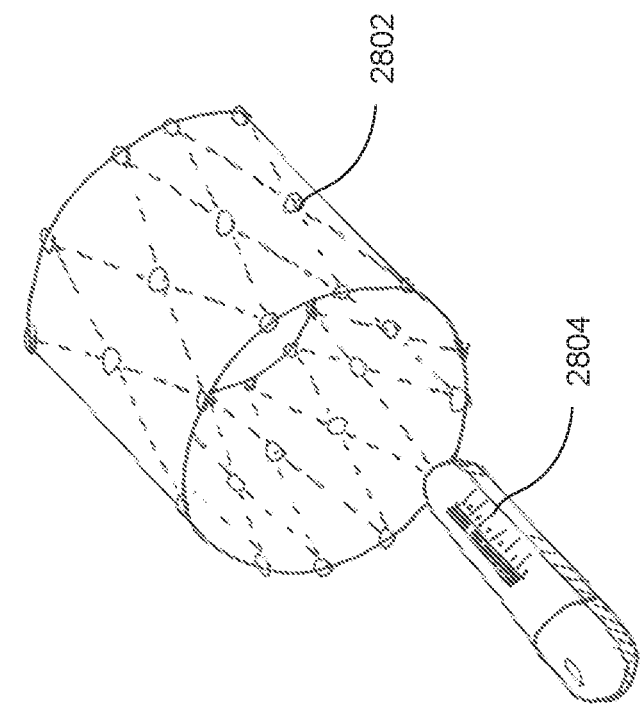
FIG. 28 illustrates another embodiment of a vaginal dilation device.

FIG. 28 illustrates another embodiment of a vaginal dilation device 2800, comprising a stent or yurt-like design. In FIG. 28, the device can comprise a plurality of scissor-like stent features 2802 that are pre-biased to expand. When the device is inserted into tissue, for example into the vagina, the stent features can automatically expand to cause the device to increase in diameter. In some embodiments, the stent features 2802 comprise a shape memory material, such as nitinol. The stent features can be configured to expand at a preset force, depending on the application and the maximum diameter desired. In some embodiments, the device can include a diameter gauge 2804 configured to display a diameter of the device. The device of FIG. 28 provides open access to the interior of the device, allowing a physician or user to gain access to the body cavity being dilated.

Figure 29:
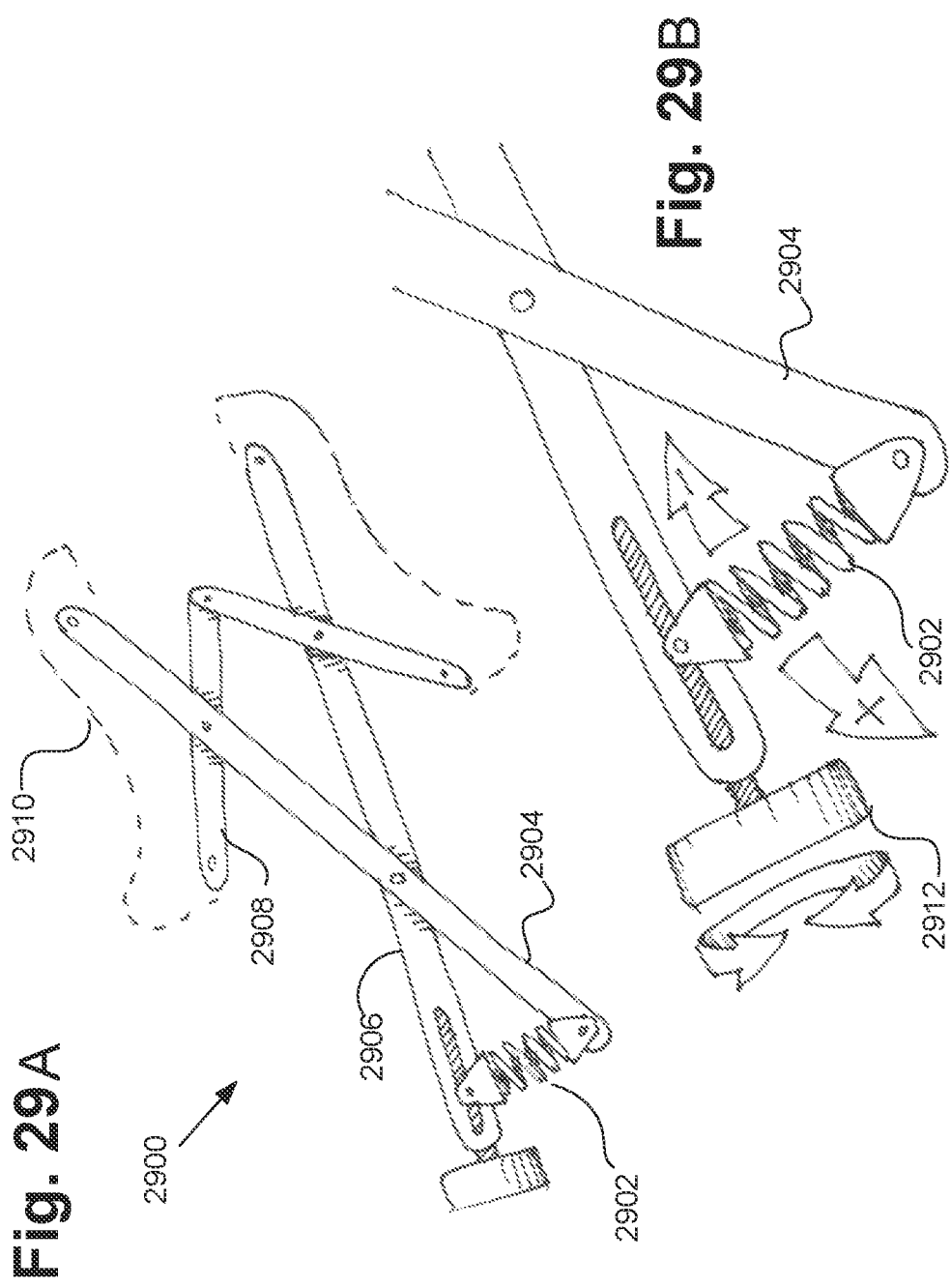
FIGS. 29A-29B illustrate another embodiment of a vaginal dilation device.

FIGS. 29A-29B illustrate another embodiment of a vaginal dilation device 2900, utilizing a simplified expansion mechanism to replace the scissor-like mechanisms described above. In FIG. 29A, a force mechanism 2902 (e.g., a spring) can apply a force to arm 2904, which pivots against central rod 2906. Arm 2904 can also pivotably connect to V-shaped mechanism 2908, which also pivots against the central rod. As the spring expands and applies force against arm 2904, it pivots against the central rod and expands V-shaped mechanism 2908. Expansion of the arm 2904 and V-shaped mechanism can cause the vaginal dilation device to expand, for example, by pushing pads 2910 outward. FIG. 29B illustrates how adjustment of dial 2912 in either direction can cause the spring to shuttle in both directions along the central arm, thereby adjusting the force applied by the force mechanism to the arm.

Figure 30:
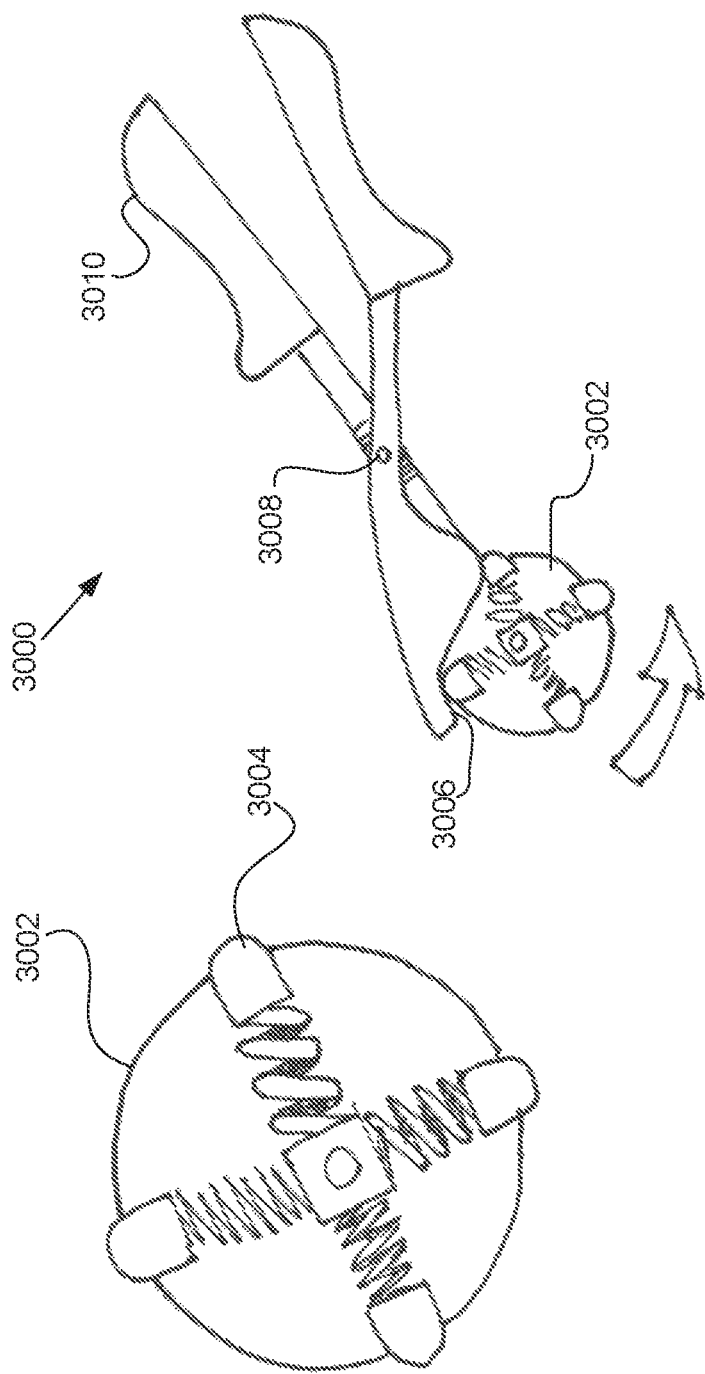
FIG. 30 illustrates another embodiment of a vaginal dilation device.

FIG. 30 illustrates yet another embodiment of a vaginal dilation device 3000, including a simplified expansion mechanism. The embodiment of FIG. 30 includes a rotating array 3002 comprising a plurality of spring plungers 3004. In some embodiments, each spring plunger applies a different force to a surface 3006 of the device. For example, referring to FIG. 30, each of the four spring plungers 3004 can have a different strength spring to apply a different force to the device. The rotating array can be rotated to change which spring plunger comes into contact with the surface of the device. As shown in FIG. 30, the spring plungers can have varying thicknesses to determine how much force is exerted by the spring. When the spring plunger exerts a force against surface 3006, the device can pivot at pivot point 3008, allowing pads 3010 to expand outwards from the device to dilate tissue.

Figure 4A:
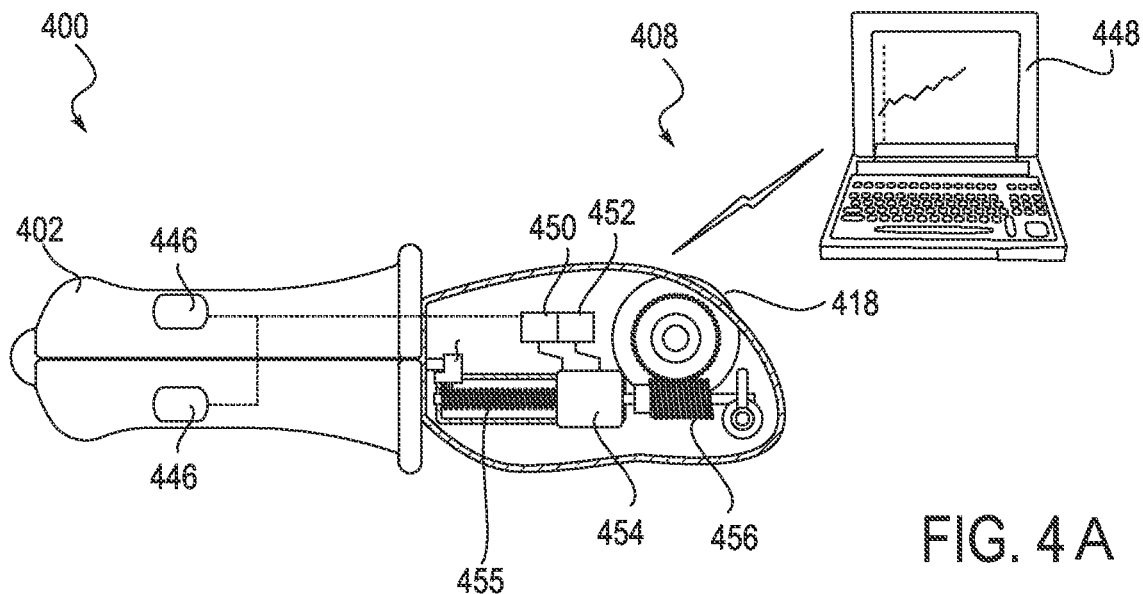
FIGS. 4A-4B show cross-sectional views of an automated vaginal dilation device.
Figure 4B:
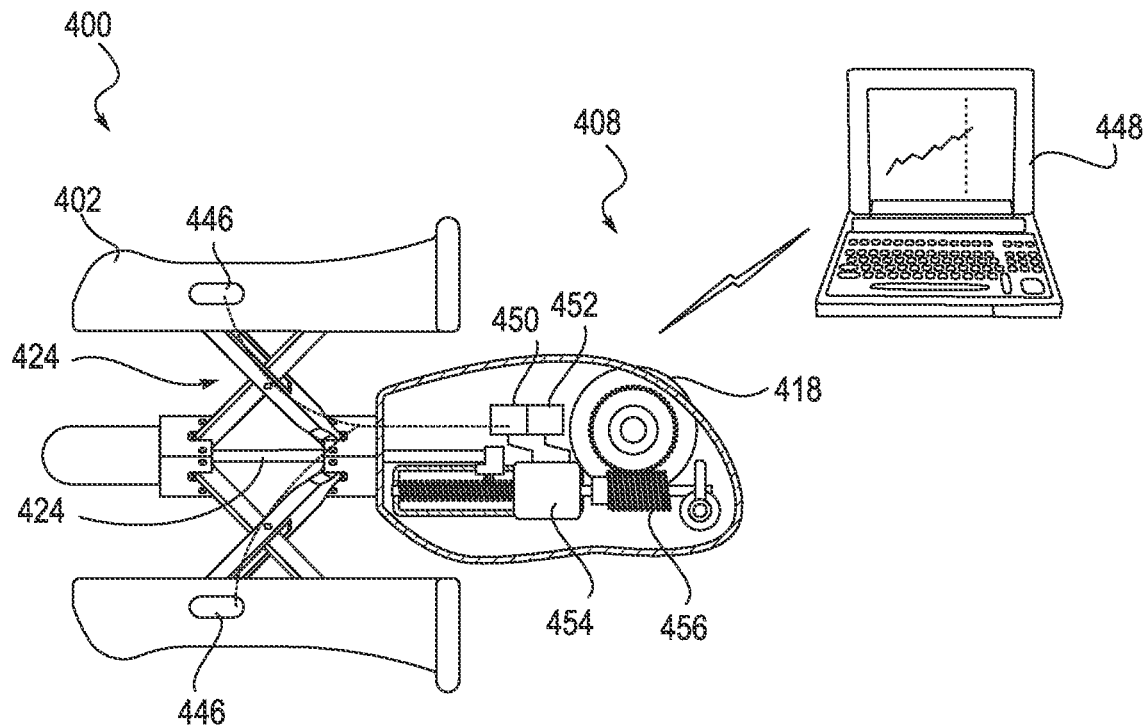
Figure 5A:
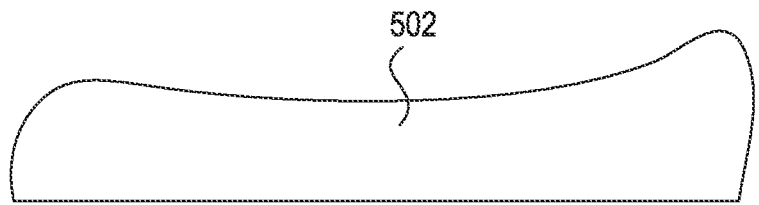
FIGS. 5A-5D illustrate various embodiments of pad shapes for use with a vaginal dilation device.
Figure 5B:
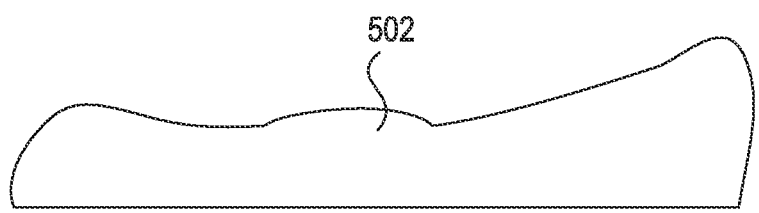
Figure 5C:
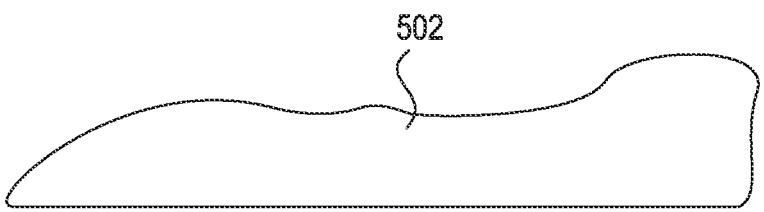
Figure 5D:
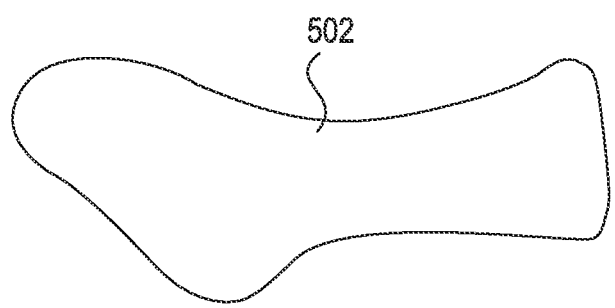

FIGS. 4A-4B show cross-sectional views of an automated vaginal dilation device 400. In contrast to the manual or semi-automated devices above, vaginal dilation device 400 can comprise a semi-automated or fully-automated actuation mechanism 408 comprising a controller 448 coupled to a motor 454 within the device and configured to automatically dilate, expand, and contract the pads and arms. Automated vaginal dilation device 400 can comprise pads 402, arms 404, handle 406, diameter sensor 418, central rod 424, force sensors 446, controller 448, receiver 450, transmitter 452, motor 454, and worm gear 456. Pads 402 and arms 404 move mechanically in a manner similar to that described above in FIGS. 1-3.

In FIGS. 4A-4B, controller 448 (e.g., a computer comprising hardware and software configured) can communicate with vaginal dilation device either wirelessly, via receiver 450 and transmitter 452, or by wire (not shown). The vaginal dilation device can measure a force applied by pads 402 to tissue, or alternatively, can measure a force applied against the pads, and transmit the measured force to controller 448 (e.g., either wirelessly or by wire). The controller 448 can be configured to automatically move the arms 404 and the pads 402 radially outwards based on the force measured by the force sensor.

For example, hardware and software installed in controller can drive motor 454 based on the measured force. Motor 454 can include a threaded shaft 455, which can engage a rack assembly disposed on central rod 424. When the motor 454 is actuated by controller 448, the threaded shaft 455 can control movement of the central rod, causing the arms and pads to expand and contract away and towards the central rod of the device. In some embodiments, motor 454 can be replaced with a pump or a computer actuated piston, for example.

Motor 454 can also be attached to a second threaded shaft 456, which can engage gears on diameter sensor 418. As the motor actuates the vaginal dilation device to expand or contract, the second threaded shaft can engage and rotate sensor 418 to indicate the diameter of the device. The measured diameter of the device can also be transmitted to controller 448 as an analog or digital signal (e.g., either wirelessly or by wire).

In other embodiments, the vaginal dilation device can include an alarm or alert mechanism, such as a visual alert (e.g., a light, or a warning indicator on a display) or an audible alert (e.g., a buzzer or an alarm sound) to indicate to a user that the device is applying too much, or too little force to the vagina. The alert mechanism can also include a timer configured to alert the user or the controller (e.g., by an audible or visual signal or by an input to the controller) when to dilate the device.

Many modes of operation are possible with the vaginal dilation device shown in FIGS. 4A-4B. For example, controller 448 can be configured to actuate motor 454 to dilate the device outwards at a constant force (e.g., a predetermined constant of approximately less than 10 lbs. of force). In another embodiment, the controller 448 can be configured to actuate motor 454 to dilate the device outwards at a time-varying force. For example, the controller can be configured to actuate motor 454 to dilate the device until the force applied by the device to tissue approaches a force threshold.

In another embodiment, a physician may initially want to dilate the vaginal tissue at a first constant force. The first constant force may be low, such less than 3 lbs. of force. After a set period of time has passed, the controller can be configured to automatically stop dilating tissue until receiving more instructions from the user, or alternatively, the controller can be configured to automatically dilate the vaginal tissue at a second constant force. The second constant force may be different than the first constant force, such as approximately 3-5 lbs. of force. In this embodiment, the vaginal dilation device 400 can automatically dilate tissue at a constant force for a set period of time, and then can either stop dilating tissue or continue to dilate at a second constant force. The controller can be configured to automatically adjust the force applied by the device to the tissue (e.g., either raise or lower the constant force) until the device achieves the desired amount of tissue dilation (e.g., 10 cm of dilation).

In another embodiment, the vaginal dilation device does not automatically dilate for a set period of time, but rather, the vaginal dilation device is configured to automatically expand and dilate tissue until a threshold force is reached (as measured by sensors 446). For example, a physician or the controller may set a threshold force of approximately 3 lbs. of force. The vaginal dilation device can then be configured to automatically dilate vaginal tissue until sensors 446 measure a force greater than or equal to the threshold force of 3 lbs. of force, at which point the device would automatically stop dilating the tissue. It should be understood that in other embodiments, the threshold force can be any force and is not limited to 3 lbs.

In yet another embodiment, the controller can be configured to actuate the vaginal dilation device to expand until a threshold force is measured, and the controller can automatically actuate the device to contract slightly upon reaching the threshold force so as to allow the vaginal tissues to relax, and thus allow the force applied by the device to the tissue to decrease.

In yet an additional embodiment, the controller can be configured to actuate the vaginal dilation device based on a sensed diameter of the device, or alternatively, based on a sensed force and a sensed diameter of the device. The diameter can be measured or sensed with diameter sensor 418. In some embodiments, the controller can be configured to dilate the device until the device reaches a preset diameter. In other embodiments, the controller can be configured to actuate the device at a first force until the device reaches a first diameter, and then to actuate the device at a second force until the device reaches a second diameter. For example, the controller can actuate the device at a force of 3 lbs. until the device reaches a diameter of 3 cm. Upon dilating to 3 cm, the controller can then automatically actuate the device at a force of 4 lbs. until the device reaches a diameter of 4 cm. This process of varying the force applied until preset diameters are reached can be continued until the target dilation diameter is achieved.

Figure 31:
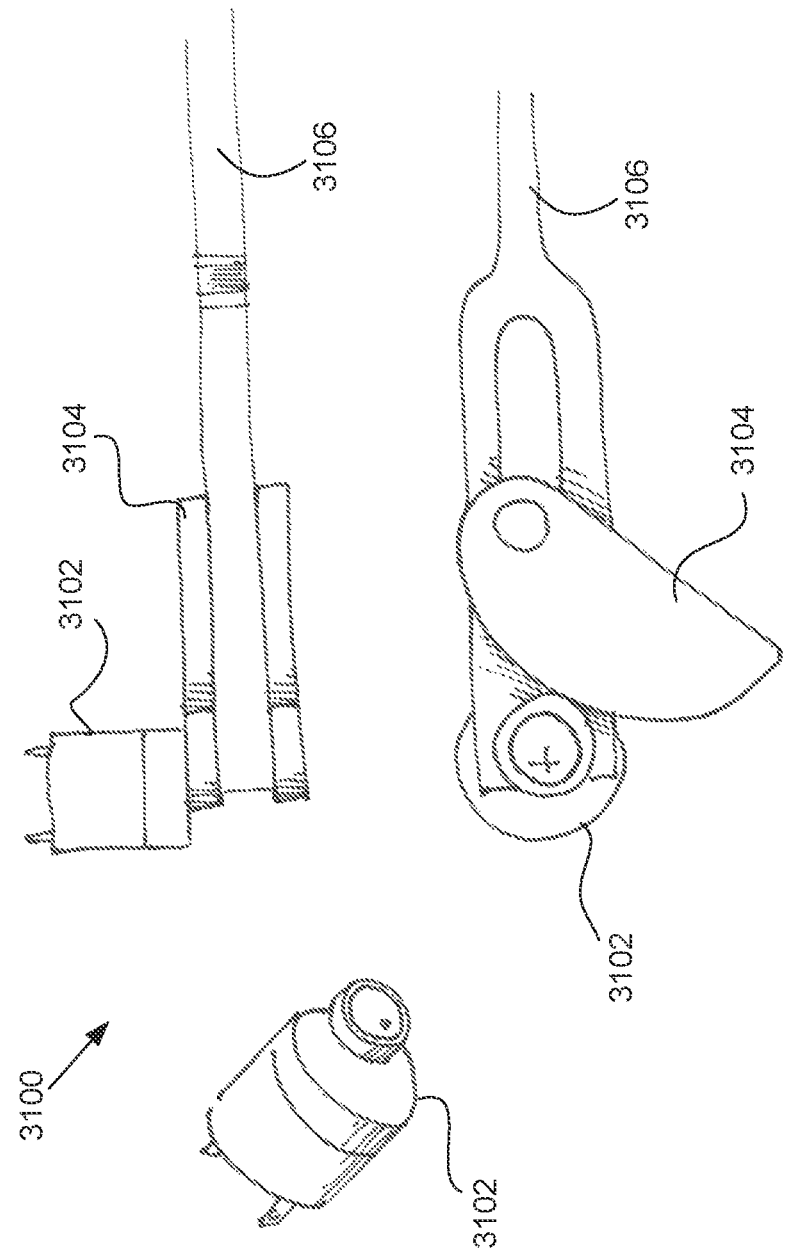
FIG. 31 illustrates another embodiment of a vaginal dilation device.

FIG. 31 illustrates another embodiment of a vaginal dilation device 3100, comprising a cam and a motor configured to automatically oscillate the device. Certain features of a vaginal dilation device not illustrated in FIG. 31 can be found in other illustrations of vaginal devices described herein, specifically FIGS. 1-3. The device functions similar to the cammed vaginal dilation device of FIGS. 21A-21C. In operation, motor 3102 can include an offset wheel which rotates against cam 3104, causing the arms (not shown) and pads (not shown) of the vaginal dilation device to oscillate. The arms and pads, and thus the device, can then oscillate radially inward and outward as described herein in other embodiments, either to promote tissue relaxation and dilation or to prevent pain.

Figure 32:
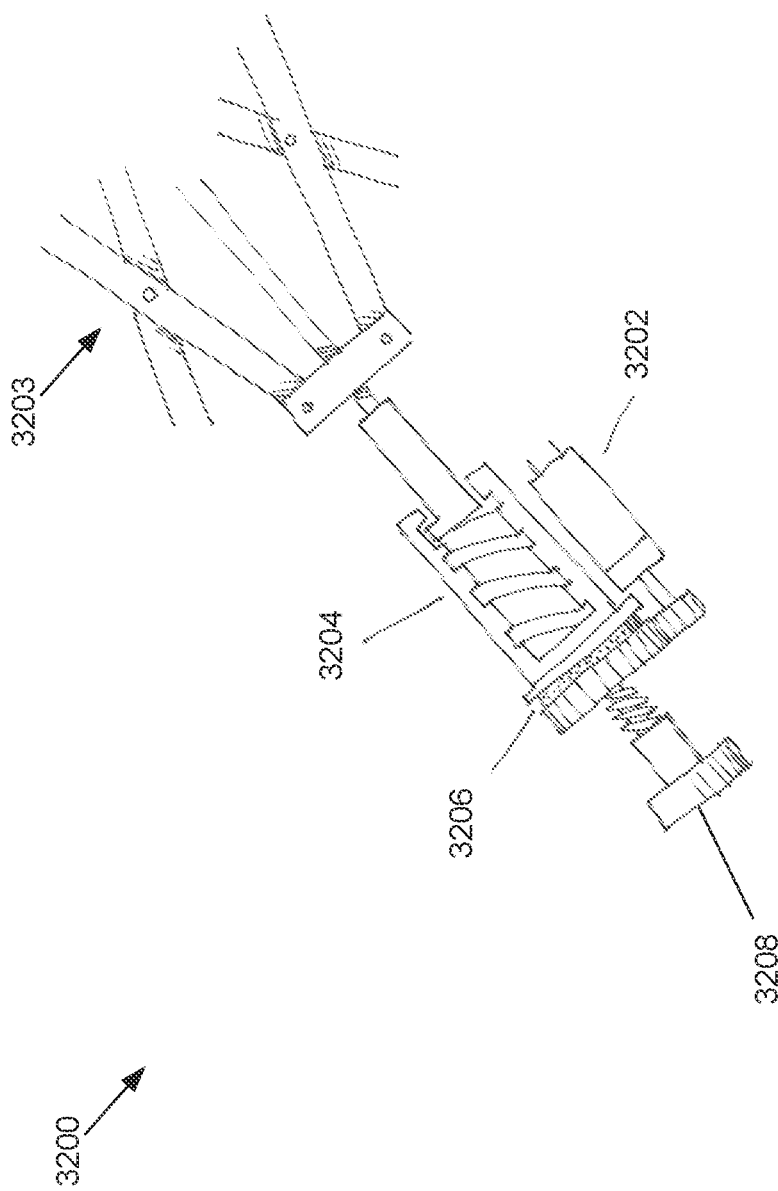
FIG. 32 illustrates another embodiment of a vaginal dilation device.

FIG. 32 describes another embodiment of a vaginal dilation device 3200 utilizing a motor 3202 and a barrel cam 3204 to normalize a force curve of the device as it expands. Certain features of a vaginal dilation device not illustrated in FIG. 32 can be found in other illustrations of vaginal devices described herein, specifically FIGS. 1-4. A barrel cam with a variable pitch groove can compensate for the varying force curve found in devices with a scissor-like expansion mechanism 3203. The pitch of the cam groove can be high at the start of a device expansion and decrease as the device progresses towards full expansion at the end. This means the barrel cam would lose mechanical advantage at the same rate the scissor mechanism gains it.

A motor driving the barrel cam would see a constant load. Adding a clutch 3206 with adjustable preload 3208 between the motor and barrel cam would allow the user to control how much force is transmitted to the scissor mechanism. The clutch could act as a failsafe, preventing the device from "running away" and opening uncontrollably. In some embodiments, irregularities or "bumps" could be added to the cam groove to cause the scissor mechanism to oscillate during expansion.

FIGS. 5A-5D illustrate various embodiments of pad shapes for use with a vaginal dilation device. The pads described herein can be covered by a soft atraumatic material made of a foam, silicone, or other rubber or gel like material. Pads 502 typically have a "saddle" shape, wherein both the distal and proximal portions of the pads are raised so as to cradle and conform to the vaginal tissue. The distal or anterior curve may better conform to the natural shape of the anatomy in order to more effectively distribute the force and provide greater stability. The proximal or posterior curve can resemble a "heel" shape to help keep the device from sliding out of the patient. As the vaginal dilation device expands and engages tissue, the tissue may slide slightly on the pad. However, the contacting surface of the introitus will remain in the "valley" of the pads. In some embodiments, such as those shown in FIGS. 5B-5C, the pads can include notches or raise portions in an intermediate area of the pad to further conform to or engage the anatomy. In other embodiments, the pads may include slits to avoid putting pressure on the anterior or posterior anatomy.

In additional embodiments, springs can be incorporated into or below the pads. These springs can keep the force of the pad on the tissue within a particular range to keep a user from over dilating the device. For example, springs incorporated into or below the pads may apply a constant force against the pads, similar to the constant force device described above in FIG. 3. In yet an additional embodiment, the device or the pads may further include an automatic oscillation mechanism configured to prevent pressure necrosis. For example, springs or other similar devices on or under the pads can be configured to automatically oscillate to reduce pressure applied to the tissue. In addition, the pads can include heating or vibrating elements to increase tissue relaxation.

Figure 6A:
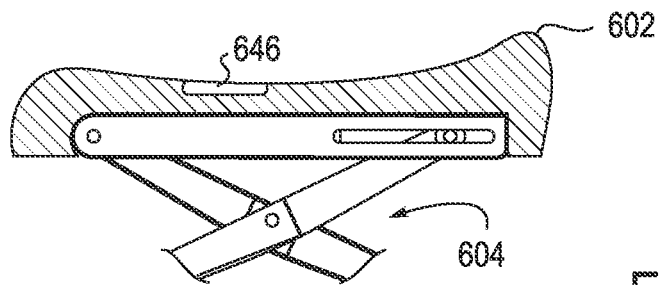
FIGS. 6A-6G illustrate various embodiments of force sensors disposed on or in a vaginal dilation device.
Figure 6B:
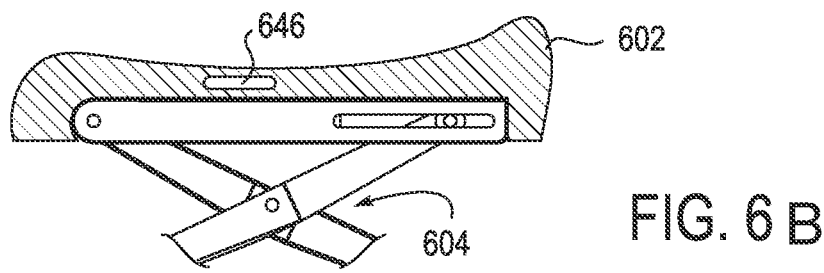
Figure 6C:
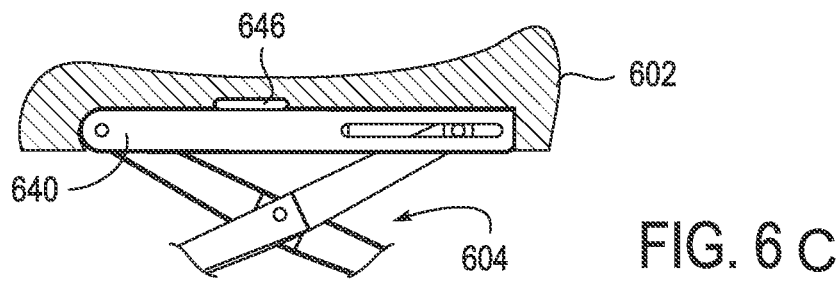
Figure 6D:
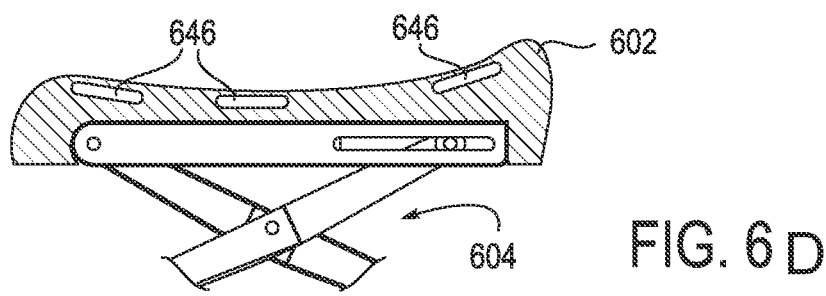
Figure 6E:
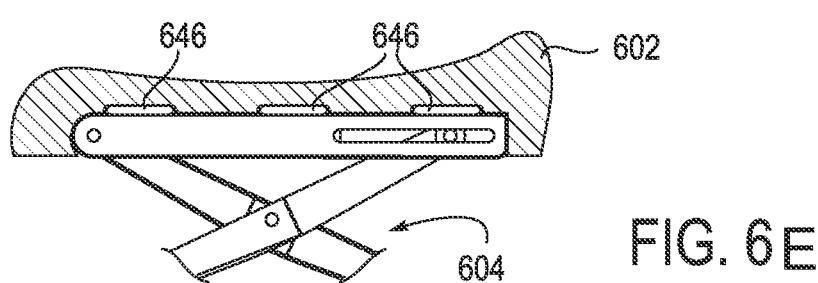
Figure 6:
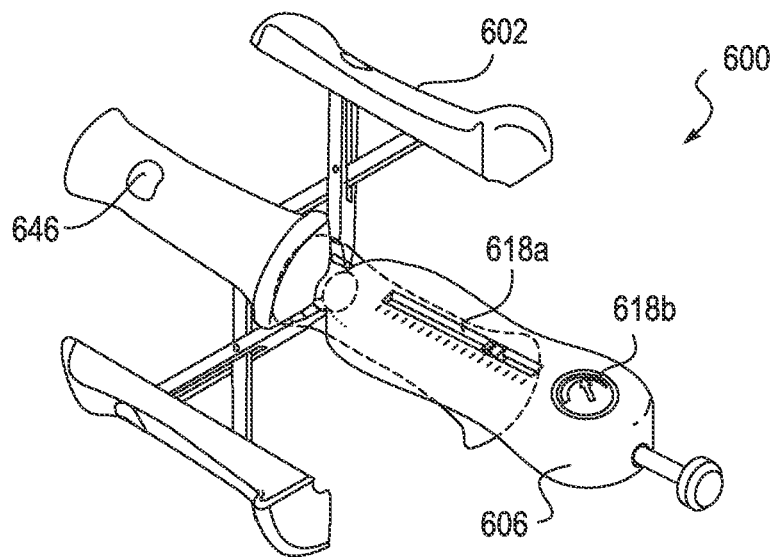
Figure 6:
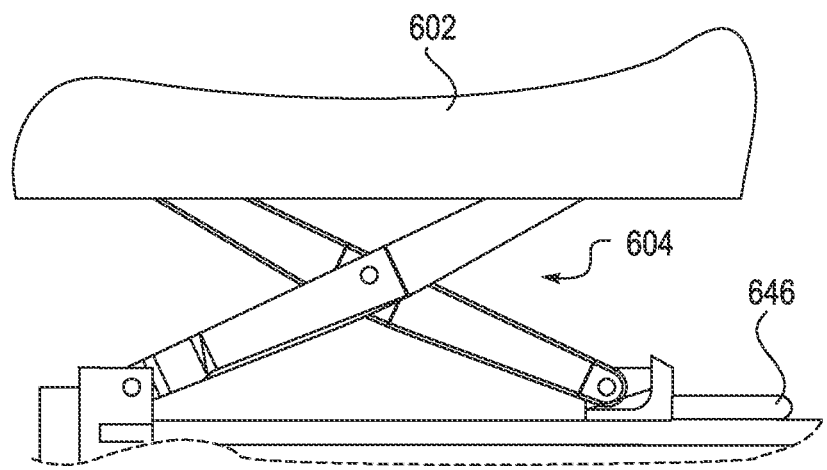

FIGS. 6A-6G illustrate various embodiments of force sensors disposed on or in a vaginal dilation device. In FIG. 6A, force sensor 646 is disposed on a surface of pad 602. In FIG. 6B, force sensor 646 is disposed below a surface of pad 602. In FIG. 6C, force sensor 646 is disposed on a surface of pad support 640, below pad 602. In FIG. 6D, multiple force sensors 646 are disposed below a surface of pad 602. In FIG. 6E, multiple force sensors 646 are disposed on a surface of pad support 640, below pad 602. FIG. 6F illustrates on embodiment of a vaginal dilation device 600, including both a diameter gauge 618a and a force gauge 618b, as well as force sensors 646 disposed on pads 602. In FIG. 6G, force sensor 646 is positioned proximally from arms 604. When arms 604 and pads 602 expand to dilate tissue, the arms can apply pressure to 646, which can measure the applied force.

FIGS. 7A-7B show embodiments of a vaginal dilation device 700 covered with a protective sheath 758, to create an expandable sterile barrier to prevent infection prior to and after delivery. The protective sheath can be an elastic material, such as latex, silicon, etc. In some embodiments, the sheath could also be made from a non-elastic material that is folded in and around the device, and unfolds as the device is expanded.

Figure 8A:
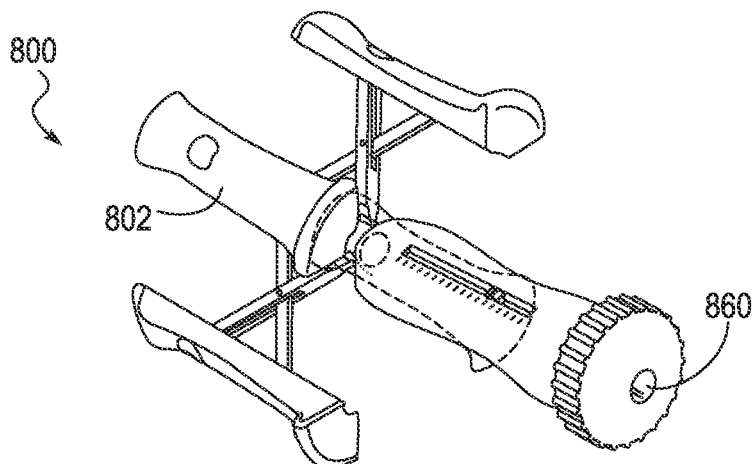
FIGS. 8A-8D illustrate various embodiments of a vaginal dilation device having working channels or through ports.
Figure 8B:
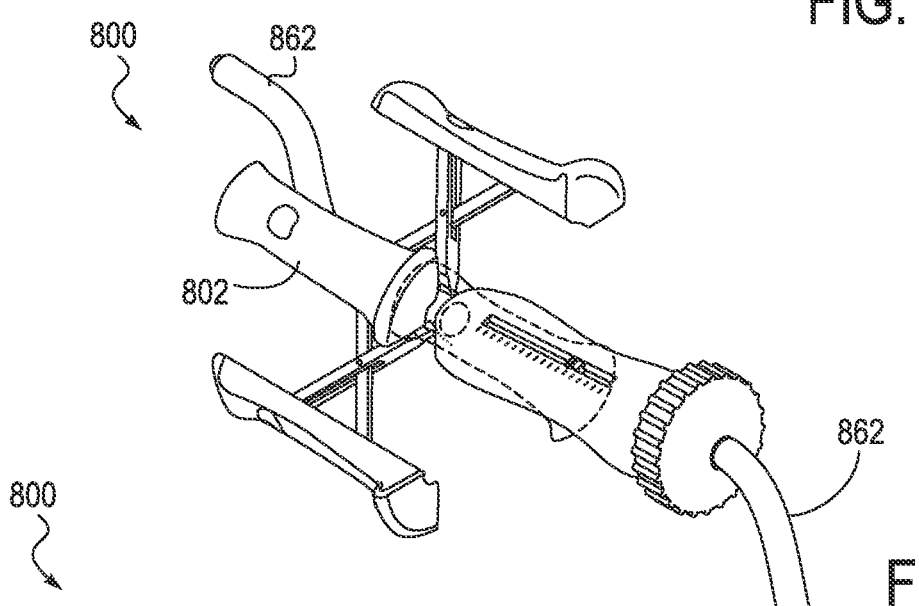
Figure 8C:
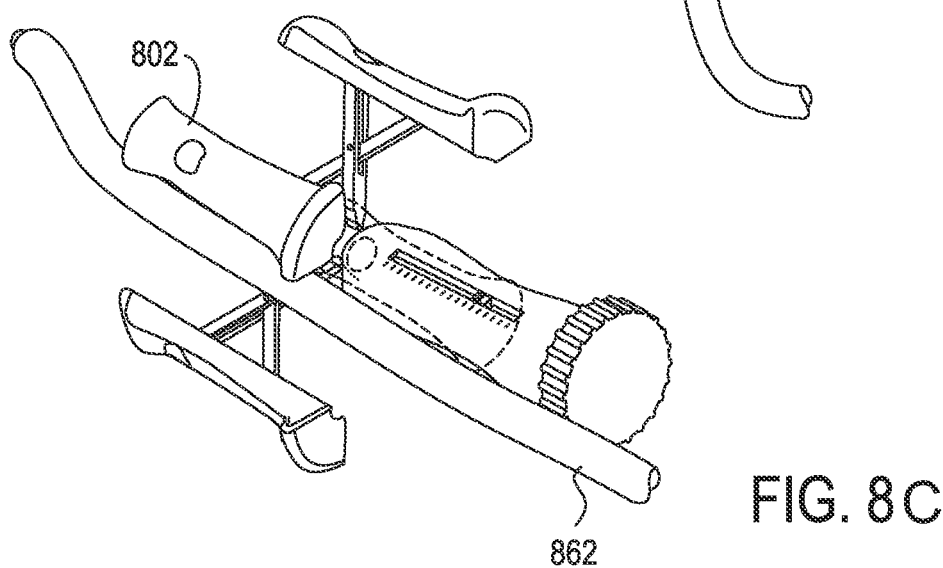
Figure 8D:
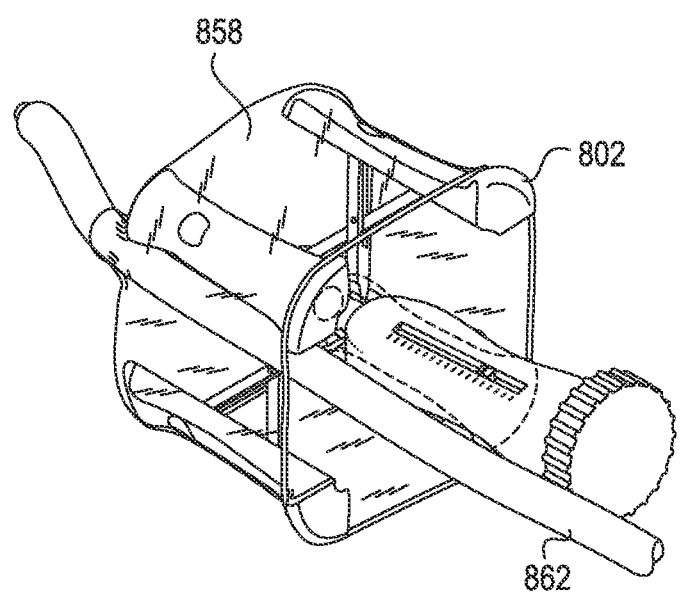

FIGS. 8A-8D illustrate various embodiments of a vaginal dilation device 800 comprising working channels or through-ports. In FIG. 8A, device 800 includes a through-port 860 through which a user can insert other devices such as cervical monitoring devices, scopes, fetal monitoring devices, or cervical dilating devices. In addition, other commonly used tools such as air, water, suction, surgical cutting devices, ultrasound or other imaging devices, etc can be inserted into the through port. In FIGS. 8B-8C, vaginal dilation device 800 can include a flexible working channel 862. The working channel can comprise a flexible, bendable material, and can accommodate any of the devices described above. In FIG. 8B, the working channel can be routed through the handle of the vaginal dilation device and out through a central axis of the pads 802. In FIG. 8C, the working channel can be routed along the side of the handle of the device, through the open space between the pads when they are expanded. FIG. 8D illustrates the working channel routed along the side of the handle and through the open space between pads 802, extending out through a protective sheath 858. There could be seals around the working channels and through-ports of FIGS. 8A-8D to keep the anatomy sterile. The working channels or through-ports can incorporate a one way valve to allow removal of fluids or tissue without allowing bacteria or other particles to enter the patient.

Figure 9:
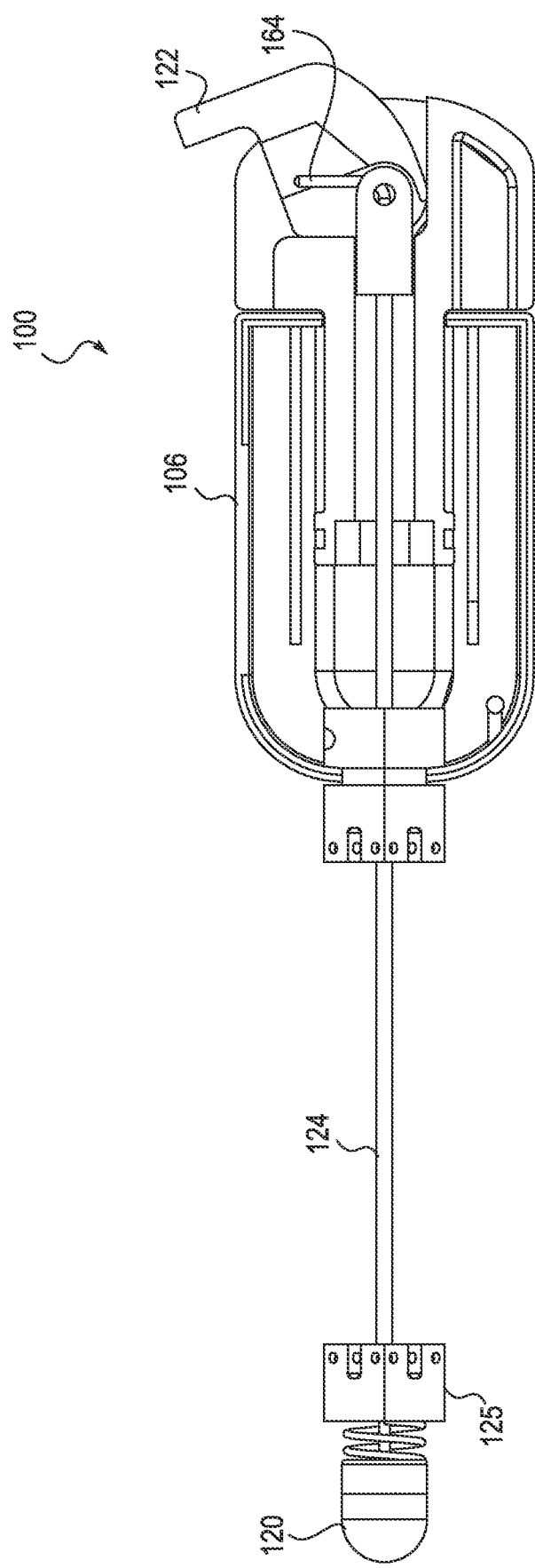
FIG. 9 illustrates a vaginal dilation device with a quick-release mechanism.

FIG. 9 illustrates a vaginal dilation device 100 having a quick-release mechanism. The quick-release mechanism can comprise bump-release 120, quick-release lever 122, and quick-release pin 164. The device shown in FIG. 9 is a simplified version of the device 100 described above, and includes central rod 124 and shuttle assembly 125. The description relating to the quick-release mechanism can be applied to any of the vaginal dilation devices described herein.

In situations where the vaginal dilation device 100 needs to be removed from the patient quickly, quick-release lever 122 can be pulled or flipped to and contract the device back to a near closed configuration. This feature allows the user to quickly stop the device from applying force to the tissue, and prevents tissue from being pinched during a quick retraction. When quick-release lever 122 is actuated, it releases a spacer which allows central rod 124 to move distally away from the handle 106 of the device. This moves shuttle assembly 125 away from the handle which changes the angle of the arms and moves the pads (not shown) towards the central rod of the device.

Figure 10B:
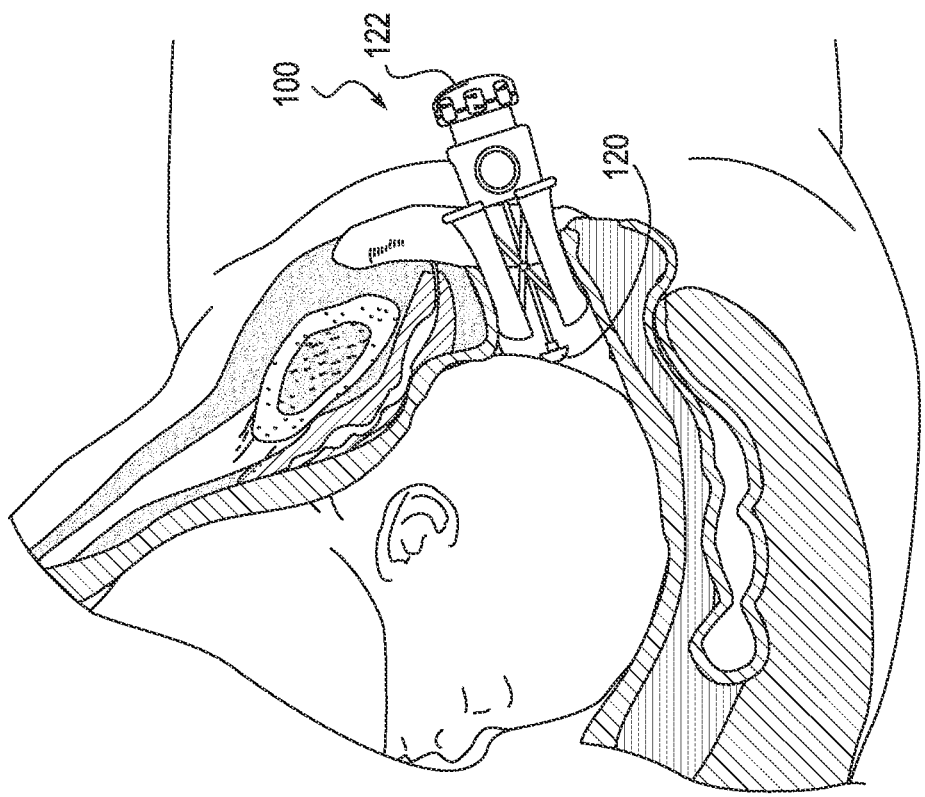
FIGS. 10A-10B illustrate a vaginal dilation device with a quick-release mechanism inserted into a female patient during labor.
Figure 10A:
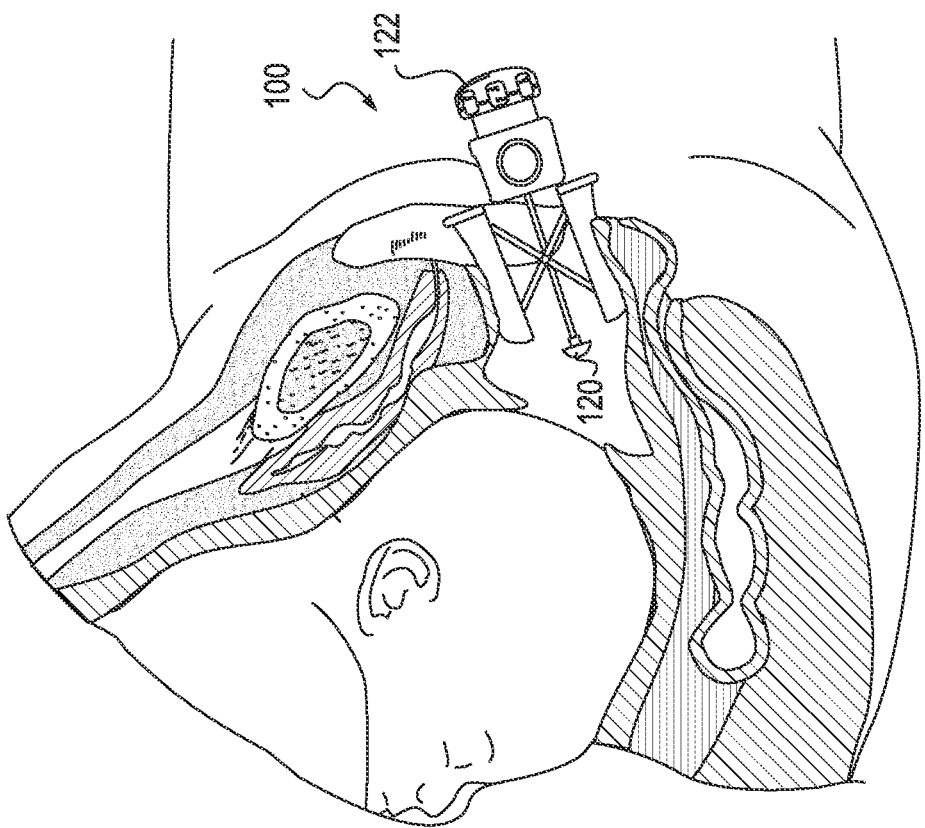

FIGS. 10A-10B illustrate a vaginal dilation device 100 having a quick-release mechanism in use. In FIG. 10A, the device 100 is shown inserted into the patient's vagina as the fetus is near delivery. Ideally, the device can be removed prior to the fetus breaching the cervix, so the user can actuate quick-release lever 122 to collapse the device into the closed configuration for removal. However, in some instances, the fetus may enter the vaginal canal with the device 100 still in place. In this situation, the fetus can engage the bump-release 120, as shown in FIG. 10B, to collapse the device into the closed configuration for easy removal. In some embodiments, actuation of the bump-release can trigger an alarm or visual/audible signal to alert a physician that the fetus has contacted the device.

Figure 11:
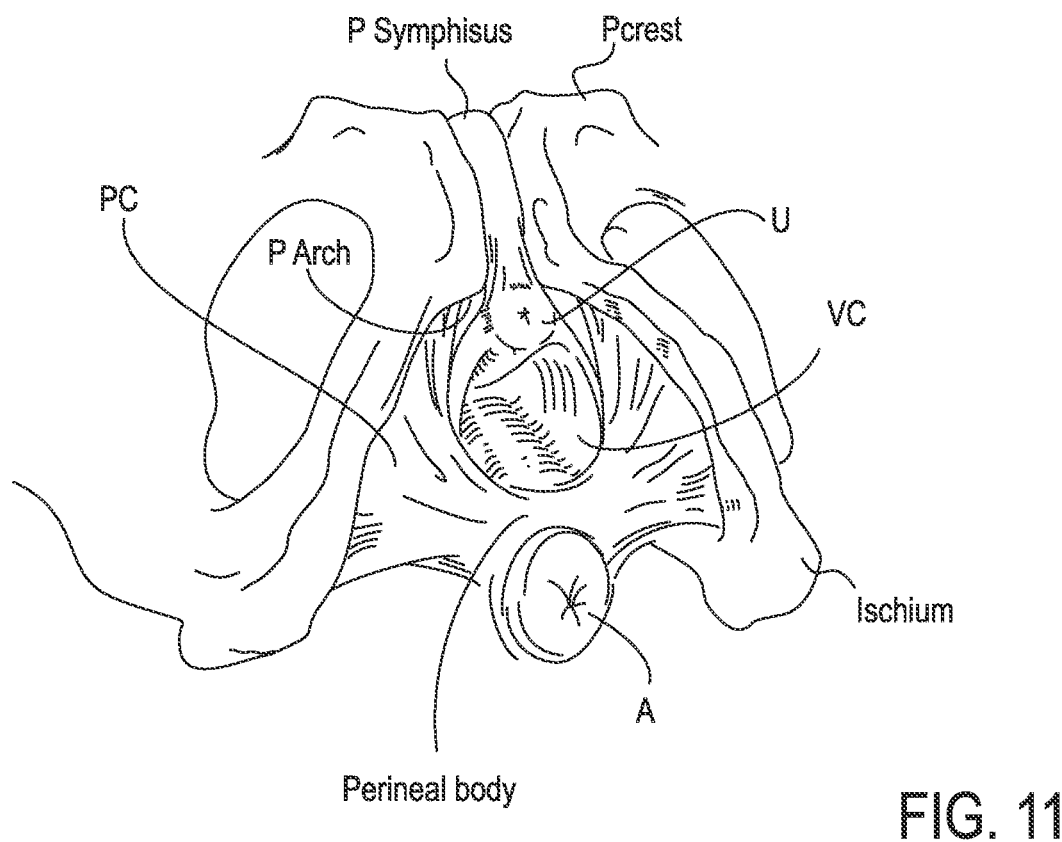
FIGS. 11-12 illustrate the female reproductive anatomy.
Figure 12:
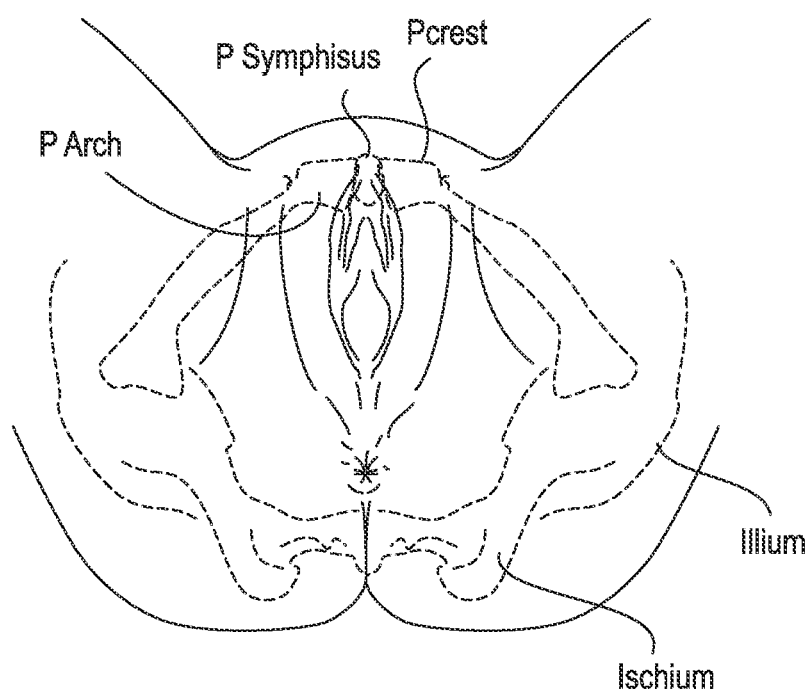

FIGS. 11-12 illustrate the bones and surround tissues of the female reproductive anatomy. The pelvic floor is defined by the pubococcygeus-puborectalis muscle complex PC, which forms a V-shaped sling running from the either pelvic sidewall anteriorly, and posteriorly around the anorectal junction. The levator hiatus is the V-shaped space between the muscular walls. Inside this V shape lies the urethra U (anteriorly), the vaginal canal VC (centrally) and the anus A (posteriorly). The area of the levator hiatus in young nulliparous (women who have never given birth) women varies from 6 to 36 cm2 on Valsalva manoeuvre. The bones surrounding the pelvic region, including the Pubic Sympisus, the Pubic Crest, and the Ischium, can also be seen in FIGS. 11-12.

The area of the average fetal head in the plane of minimal diameters measures 70-100 cm' (equating to a head circumference of 300-350 mm), requiring marked distension and deformation of the levator complex. It has been shown with the help of MRI-based computer modeling that the most inferior and medial parts of the levator complex have to increase in length by a factor of 3.26 during crowning of the fetal head. Given this degree of acute distension, it is remarkable that severe muscular trauma is not even more prevalent, as such stretch is commonly thought to be well beyond the approximately 150% elastic limits of tissue strain.

Figure 13A:
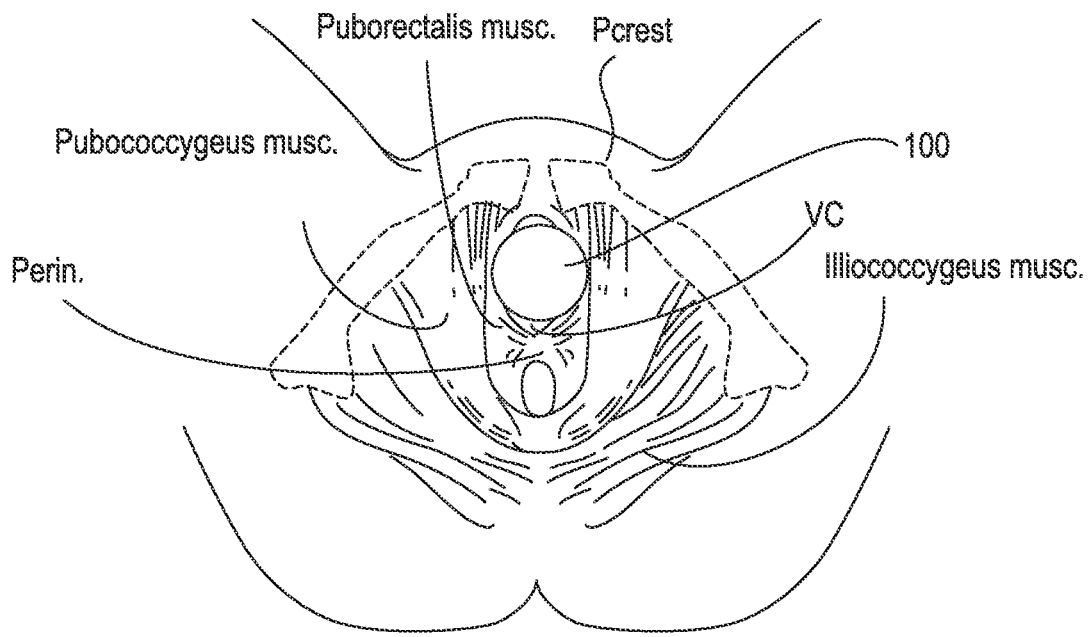
FIGS. 13A-13B illustrate a vaginal dilation device inserted into a female patient in both a closed and expanded configuration, respectively.
Figure 13B:
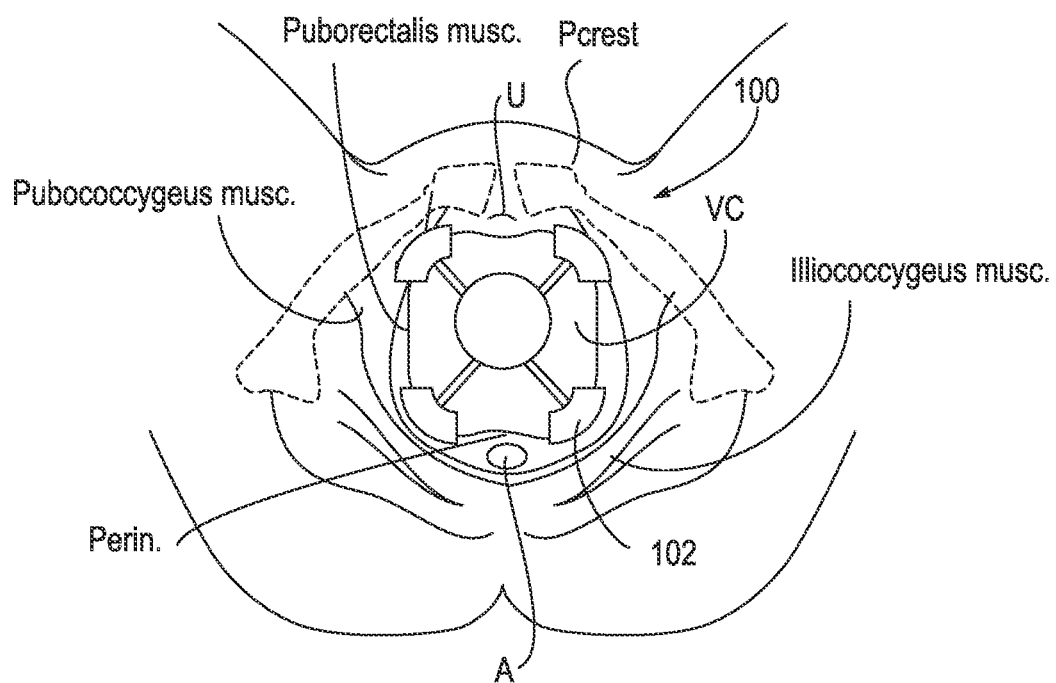

FIGS. 13A-13B illustrate a vaginal dilation device 100 inserted into a female patient in both a closed and expanded configuration, respectively. The vaginal dilation device of FIGS. 13A-13B can be any vaginal dilation device described herein. In FIG. 13A, the device 100 is shown inserted into the vagina in a closed configuration. The outer diameter of the device in the closed configuration can be less than 4 cm to increase patient comfort. FIG. 13B illustrates device 100 inserted into the vagina in an expanded configuration. The outer diameter of the device in the expanded configuration can be up to approximately 10 cm. The orientation of pads 102 with respect to the anatomy is also shown. In FIG. 13B, vaginal dilation device 100 includes four pads 102. When the pads are expanded, the pads avoid placing pressure on critical parts of the anatomy, such as the urethra U and the perineum and anus A. In other embodiments where more than four pads are incorporated in the device, the device does not include pads that expand directly upwards (to avoid putting pressure on the urethra) or directly downwards (to avoid putting pressure on the perineum and anus).

Methods of using a vaginal dilation device will now be described. FIGS. 14A-14D illustrate a vaginal dilation device inserted into a female patient during labor. The vaginal dilation device described in these methods can be any vaginal dilation device described herein, including the fully manual vaginal dilation device of FIGS. 1-2, the semi-automated vaginal dilation device of FIG. 3, or the fully semi or fully-automated vaginal dilation device of FIG. 4. In addition, the vaginal dilation device shown in FIGS. 14A-14D may include any of the additional features described herein, including force sensors, diameter gauges/sensors, working channels, protective sheaths, etc.

Figure 14A:
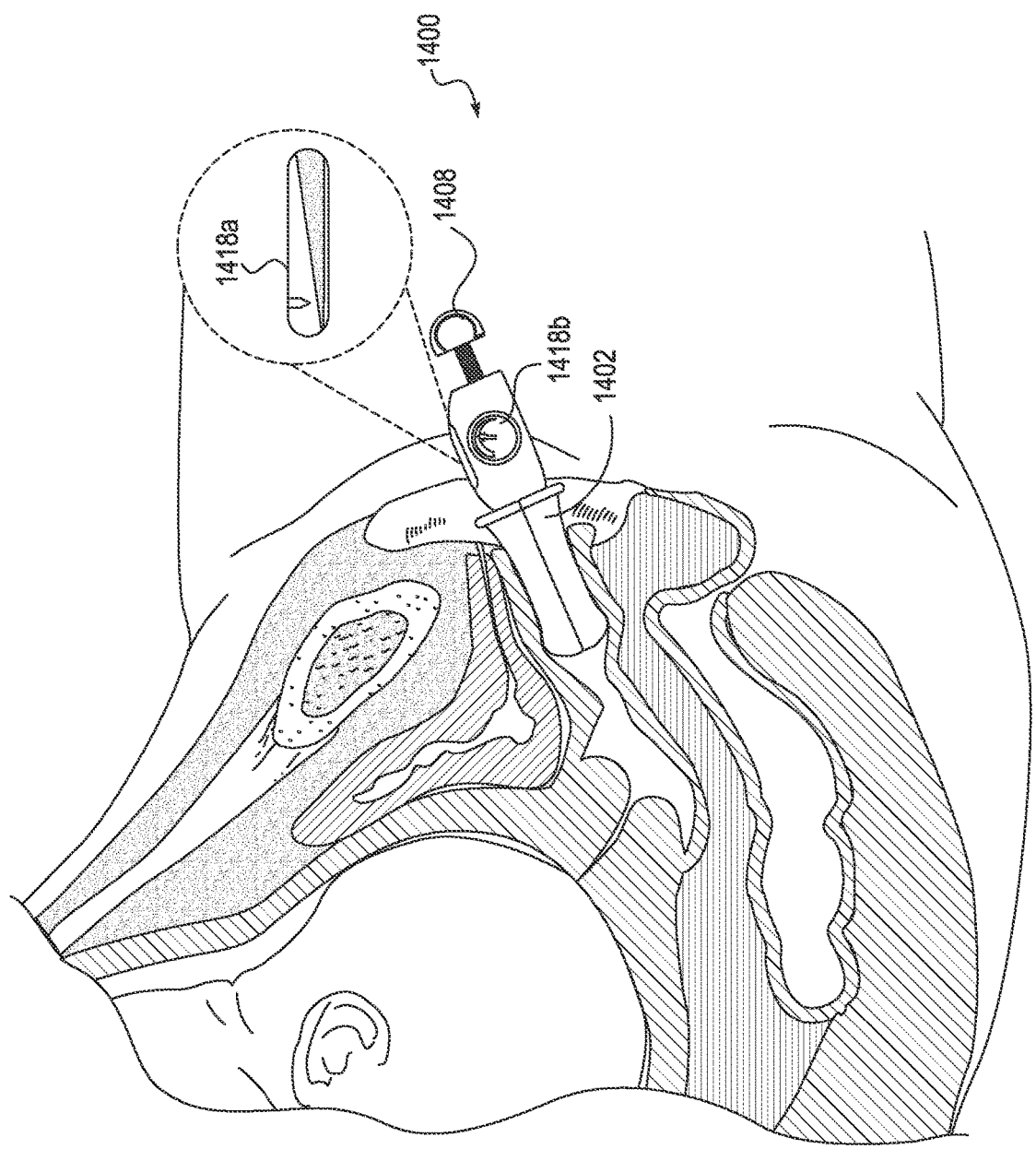
FIGS. 14A-14D illustrate a vaginal dilation device inserted into a female patient during labor.

In FIG. 14A, vaginal dilation device 1400 is shown inserted into the vagina of a patient and can include pads 1402, actuation mechanism 1408, diameter gauge 1418a, and force gauge 1418b. The device can include sensors for measuring force and/or diameter, not shown, but described above. In the embodiment of FIG. 14A, the device is shown with an actuation mechanism comprising a mechanical knob, but it should be understood that in other embodiments, the actuation mechanism can comprise a constant force device such as a spring, or a fully automated system such as a controller and a motor. The device 1400 of FIG. 14A is shown in a closed or compact configuration. The device can be inserted into the patient any time during the first phase of labor, typically when the patient arrives at the hospital prior to giving birth. On average, a woman spends 14 hours in a hospital until the second phase of labor begins. Diameter gauge 1418a can give an indication of the outer diameter of the pads of the device, to indicate how far the vaginal tissue has dilated. Force gauge 1418b can indicate the amount of force being applied by the pads to tissue, or alternatively, the amount of forced applied against the pads.

Figure 14B:
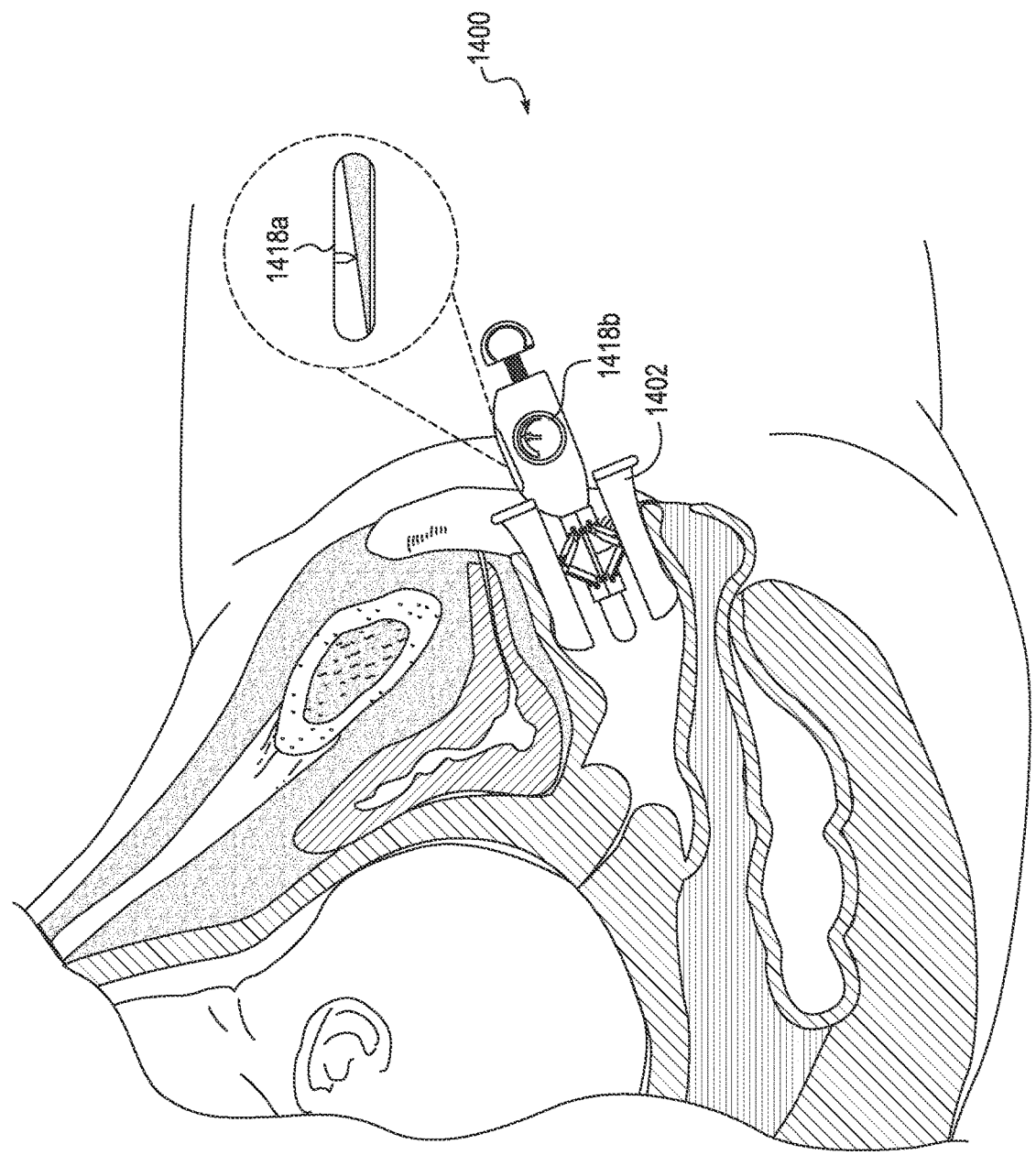
Figure 14C:
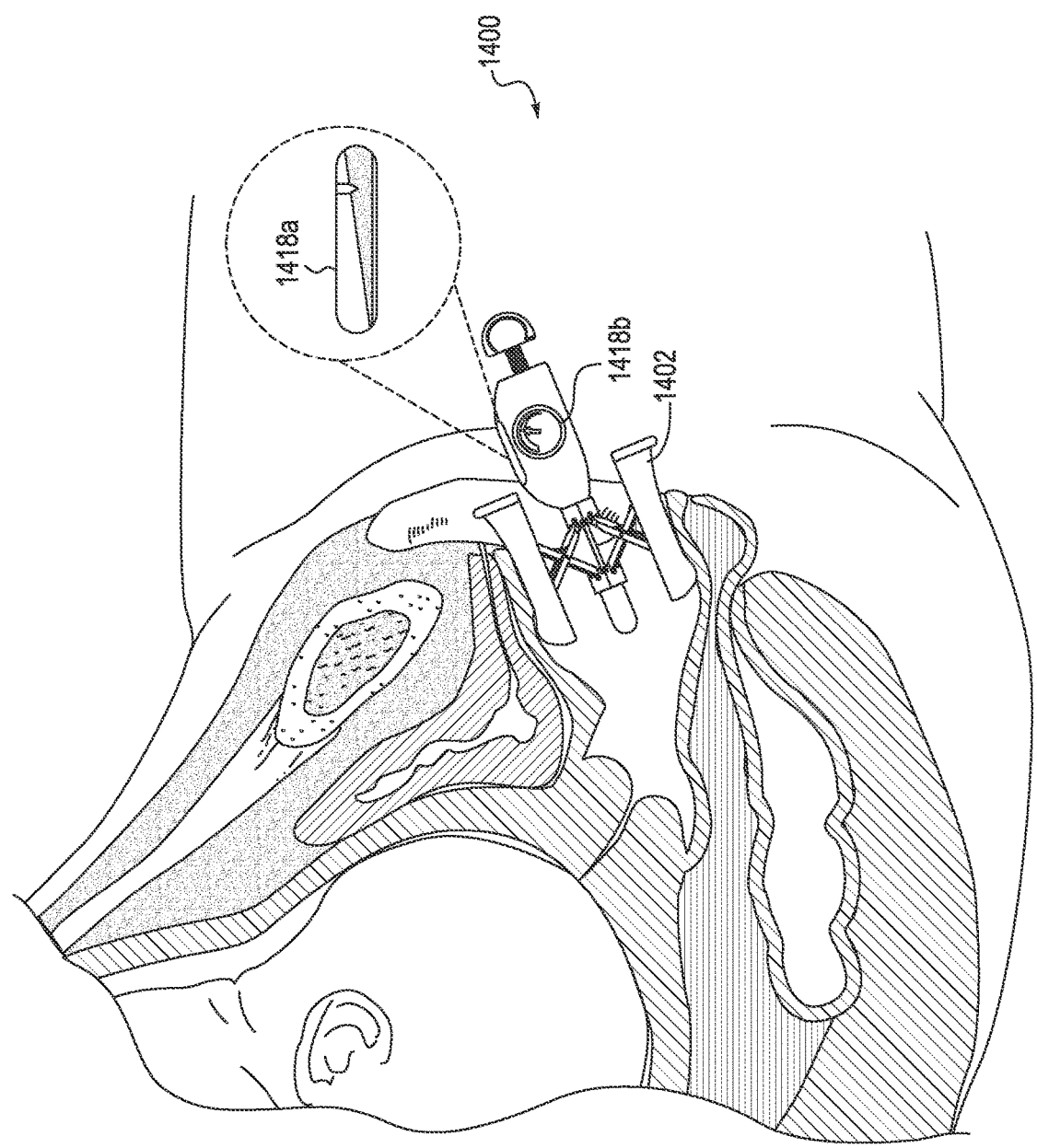
Figure 14D:
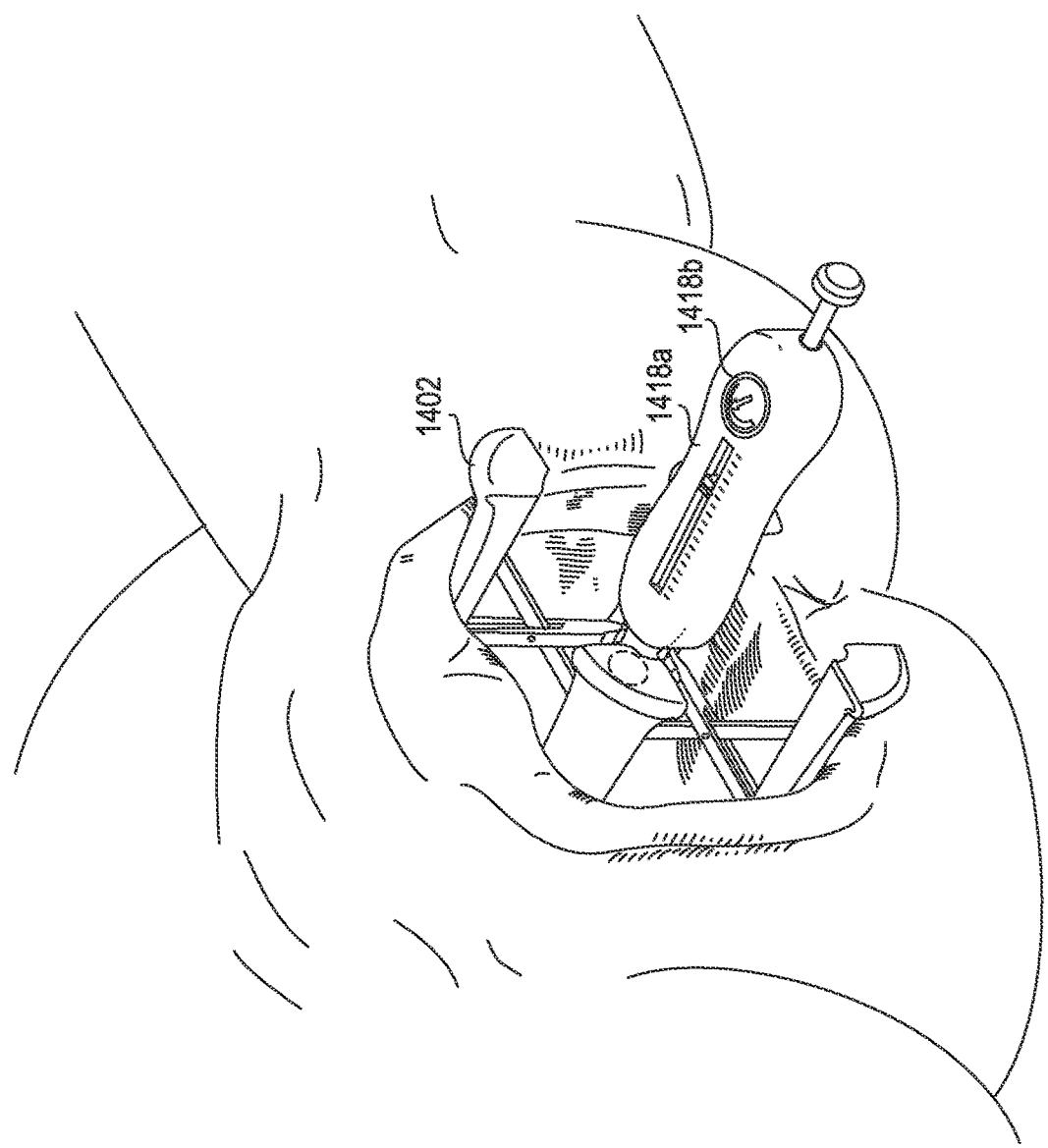

FIG. 14B illustrates the vaginal dilation device 1400 after being partially dilated. Diameter gauge 1418a indicates the expanded diameter of the device to a user. Force gauge 1418b can be monitored by the user, or alternatively, by a controller (not shown) to ensure proper, safe use of the device and to prevent trauma to the tissue. In FIG. 14C, vaginal dilation device is shown in a fully expanded configuration, effectively dilating the vaginal tissue to the desired diameter (e.g., 10 cm). Diameter gauge 1418a indicates that the diameter of the device has reached the target diameter to a user. Force gauge 1418b can be monitored by the user, or alternatively, by a controller (not shown) to ensure proper, safe use of the device and to prevent trauma to the tissue. FIG. 14D is an alternate view of a vaginal dilation device in an expanded configuration. The device shows diameter and force gauges 1418a and 1418b on the top of the device for easy readout by the user. Pads 1402 are shown applying pressure to the vaginal tissue, but avoiding putting pressure on the sensitive tissue areas of the urethra, the perineum, and anus.

Figure 15:
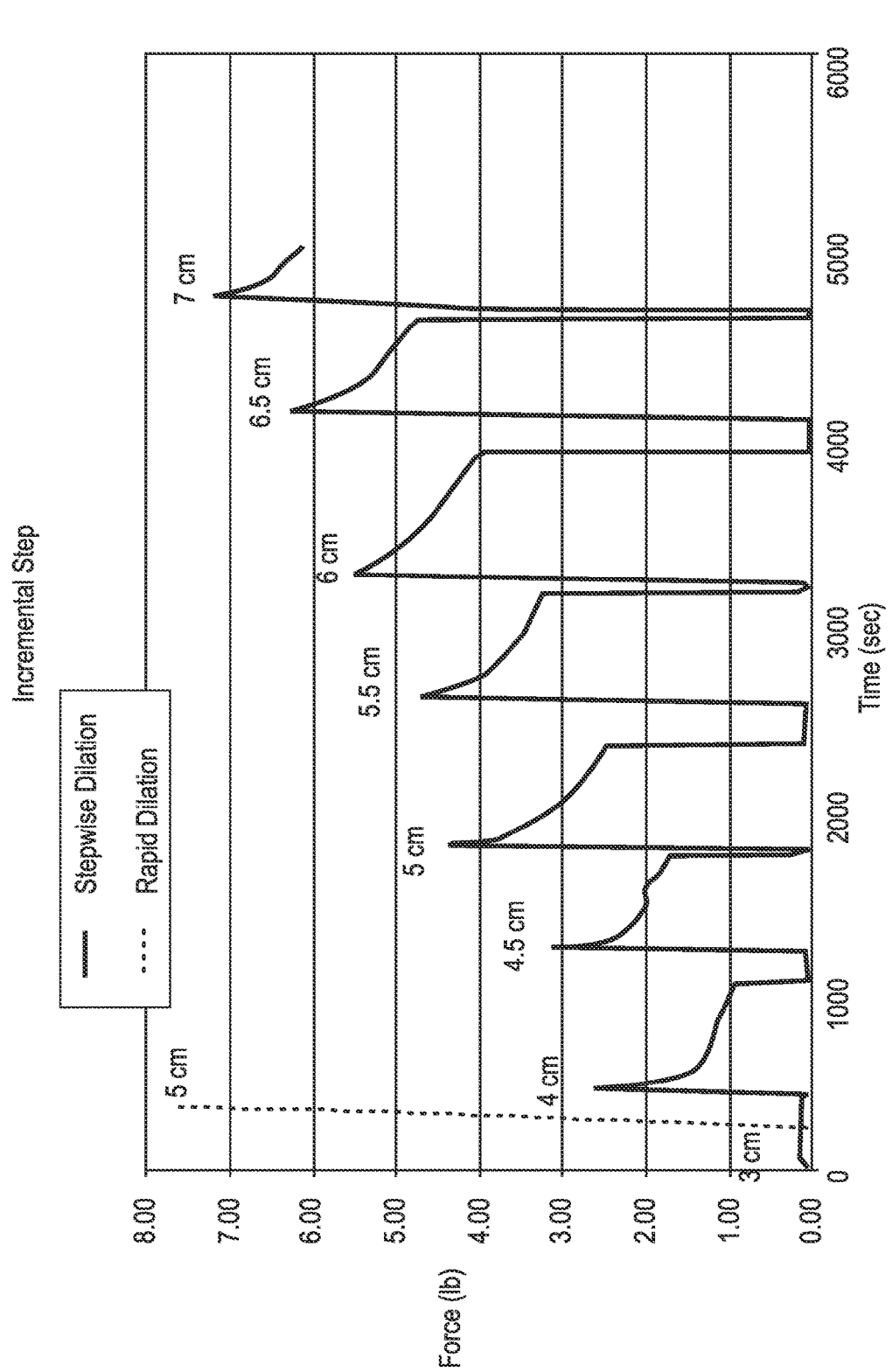
FIG. 15 is a chart illustrating one method of dilating vaginal tissue during labor.

FIG. 15 is a chart illustrating two methods of dilating vaginal tissue in a case study. Referring to the chart, the diameter of vaginal tissue was increased from 1.1 cm to 7 cm over a period of 1 hour and 15 minutes. The amount of force applied to tissue was ramped up gradually to avoid tissue damage. For example, initially, a force of approximately 2.5 lbs. was applied by the device to tissue to dilate the tissue to 4 cm after approximately 500 seconds. After the initial dilation, the tissue was allowed to relax, and it can be seen that the force applied by the device to tissue decreased to almost 1 lb. after approximately 1000 seconds. Next, a force of approximately 3 lbs. was applied by the device to tissue to dilate the tissue to 4.5 cm, followed by a time period of no additional dilation which allowed the force applied to decrease to below 2 lbs. This process was repeated by applying approximately 4.5 lbs. of force to dilate the tissue to 5 cm, applying approximately 5.5 lbs. of force to dilate the tissue to 5.5 cm, applying approximately 4 lbs. of force to dilate the tissue to 6 cm, applying approximately 6 lbs. of force to dilate the tissue to 6.5 cm, and applying approximately 7 lbs. of force to dilate the tissue to 7 cm.

It should be understood that these values are merely explanatory, as every woman's body and tissue response to treatment may be different. In general, however, a method of dilating vaginal tissue can comprise inserting a vaginal dilation device into the vagina, measuring a force applied by the vaginal dilation device to the vagina, dilating the vagina with the vaginal dilation device, and pausing or stopping dilation of the vagina with the vaginal dilation device when the force applied by the vaginal dilation device to the vagina increases to a first force threshold. In some embodiments, the method further increases measuring a diameter of the vagina with the vaginal dilation device. Next, the method can include resuming dilation of the vagina when the force applied by the vaginal dilation device to the vagina decreases to a second force threshold. For example, a user or controller may determine that the tissue has relaxed enough that it is time to begin dilating the vaginal tissue to a larger diameter. In some embodiments, dilation is resumed until the force applied by the vaginal dilation device increases to the first force threshold, or alternatively, until the force applied increases to a third force threshold larger than the first force threshold. In some embodiments, the first, second, and third force thresholds range from approximately less than 8 lbs. of force.

The embodiment of FIG. 15 can utilize the visco-elastic properties of the patient's muscle and connective tissue to achieve maximum dilation. The tissue can be stretched to some predetermined maximum stress or force with the device, then the tissue can be allowed to relax to reduce the stress, followed by again increasing the diameter of the device to the maximum stress value. This cycle of tissue stressing, tissue stress relaxation, and then diameter increases to re-stress the tissue can be performed until the full tissue preparation diameter of approximately 10 cm is achieved.

Figure 16:
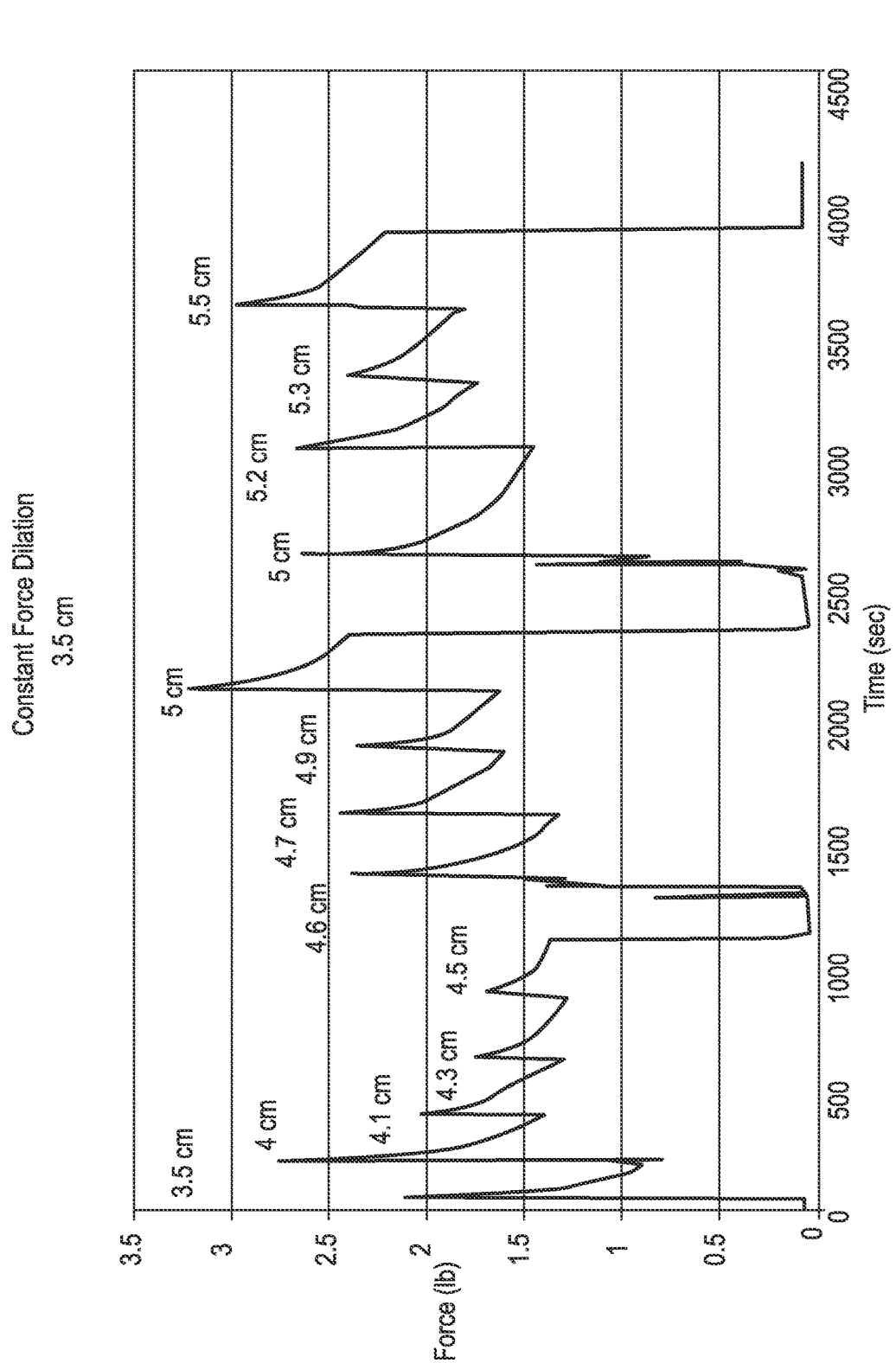
FIG. 16 is a chart illustrating another method of dilating vaginal tissue during labor.

FIG. 16 is a chart illustrating another method of dilating vaginal tissue during labor at a constant force. FIG. 16 illustrates the results of a constant force dilation from a case study. Vaginal tissue can be dilated at a constant force with any of the vaginal dilation devices described herein, but particularly with the vaginal dilation devices described in FIGS. 3 and 4. Referring to the constant force dilation chart of FIG. 16, the vaginal diameter was increased from a baseline diameter of 1.0 cm up to 5.5 cm over approximately 1 hour. The force was held to lower values by incrementally increasing the diameter in smaller steps more frequently. As in the incremental dilation test (described above in FIG. 15), there is a rapid decrease in force when first dilating to a new diameter, and by increasing the diameter more frequently, the tissue is allowed persistent stress relaxation.

Figure 17:
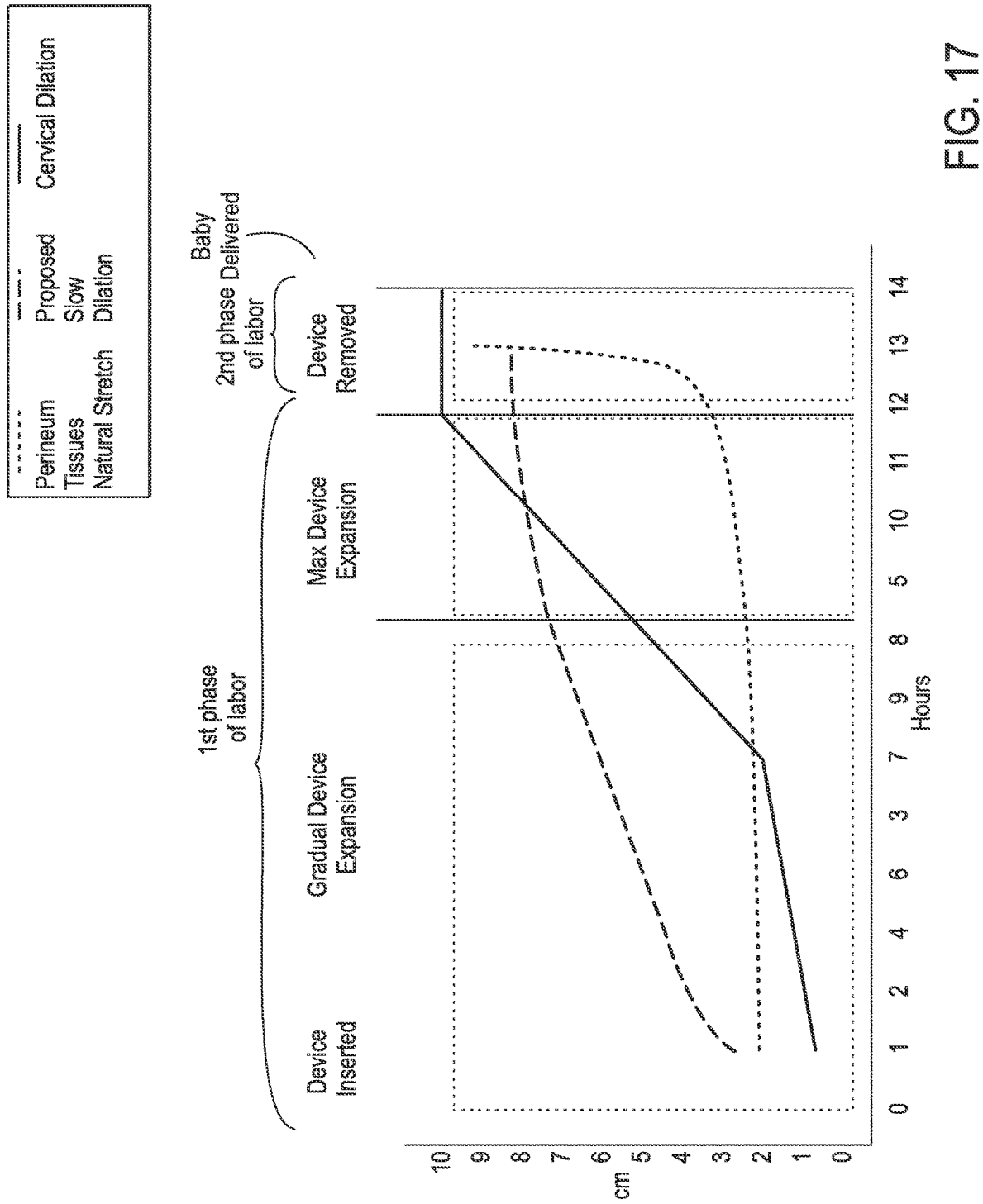
FIG. 17 is a chart illustrating another method of dilating vaginal tissue during labor.

FIG. 17 is a chart illustrating the various phases of labor and the relative dilation diameters of the patient's cervix and vagina. During the latent or first phase of labor, the cervix dilates up to approximately 3-4 cm over a span of about 8 hours. Over the final 6 hours or so of labor, the cervix dilates to approximately 10 cm. The natural stretch of perineal tissues is also shown in FIG. 17. It can be seen that the natural tissue response is for the perineal tissues to be dilated naturally at approximately 2 cm, until the final moment of labor when the perineal tissues stretch to 10 cm, leading to tearing and tissue damage. In one embodiment, the perineal tissues can be gradually dilated and expanded with a vaginal dilation device. For example, the perineal tissues can be dilated with the vaginal dilation device to approximately 7-10 cm during the first phase of labor. During the second phase of labor, the vaginal dilation device can be removed from the patient, allowing the birth to occur while the perineal tissues are stretch and relaxed.

The vaginal dilation devices described herein can be used during the first stage of labor, in the hospital, under the supervision of trained physician obstetricians and nurses. The device can be designed as a single use, disposable dilator configured to penetrate the first third of the vagina, and configured to gradually expand the vagina and the perineal tissues from a resting diameter of 2-3 cm to a fully expanded diameter in preparation of the delivering an infant, roughly 10 cm. Expansion can be controlled either manually or via an automatic actuation system, and the device can be removed quickly if needed The device could be inserted any time during the first stage of labor, and can be configured to dilate in small 5-15 minute increments. In between dilations, the patient can remove the device and ambulate if needed. The progression of the cervix could be used as a guideline of the progression of labor. In order to reduce or eliminate any discomfort, the device can be used under epidural analgesia or local anesthesia on the vagina. In some embodiments, the device can dilate the tissue for approximately 1-3 hours to successfully reduce the internal stresses in the tissue and prepare the tissue for the second phase of labor. The device can then be removed prior to the second phase of labor begins, so as to allow delivery to occur unobstructed.

Figure 18:
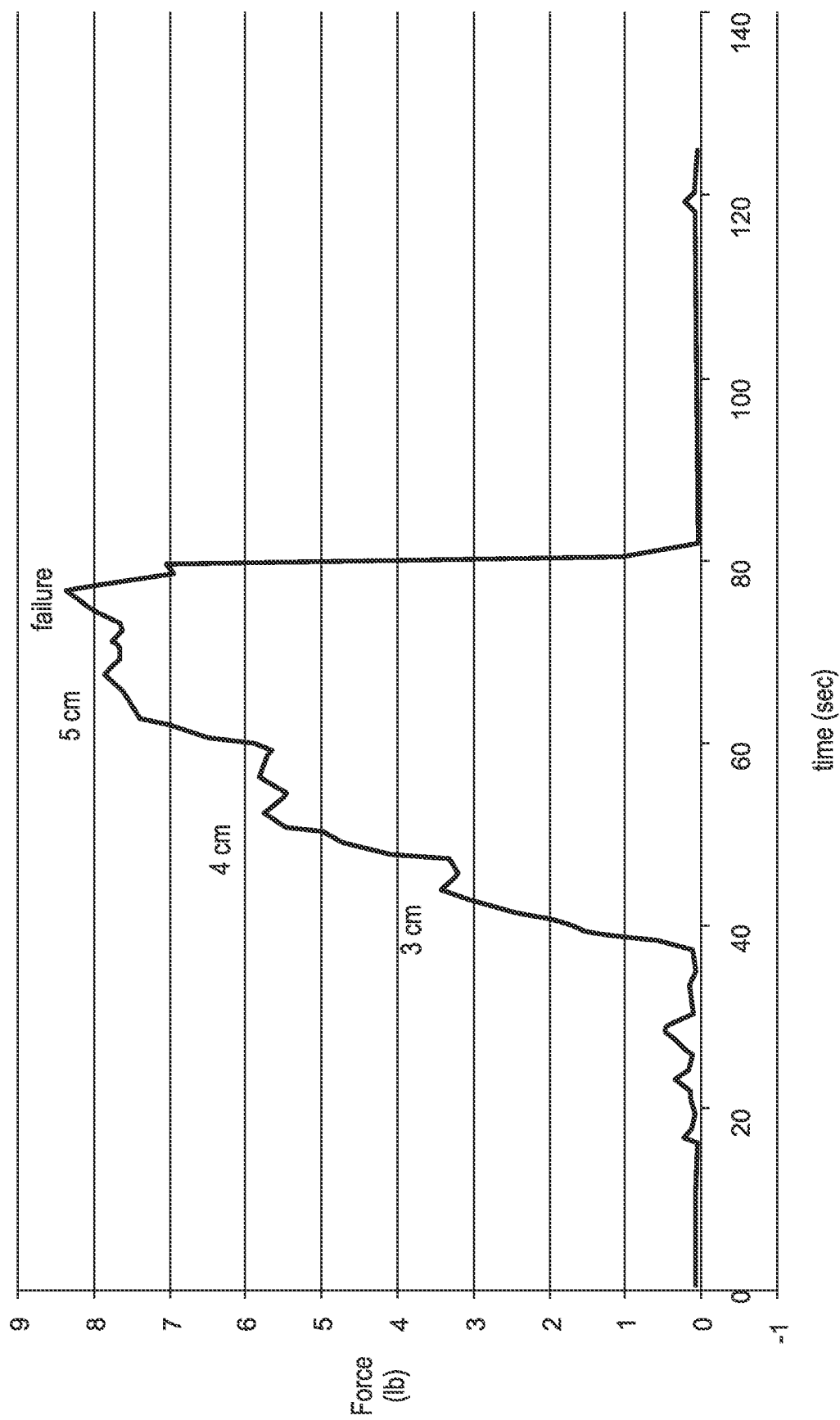
FIG. 18 is a chart illustrating an additional method of dilating vaginal tissue during labor.

FIG. 18 is a chart illustrating an additional method of dilating vaginal tissue during labor. In FIG. 18, another embodiment of dilating vaginal tissue is illustrated. In this embodiment, the vaginal dilation device is configured to dilate the tissue at a constant rate. As the device dilates the tissue, the force applied by the device to the tissue will increase. This method can be used in situations where it is necessary to dilate the tissue quickly. A typical female has a resting vaginal diameter of approximately 2-3 cm. In one embodiment, it is desired to dilate the vagina to approximately 9-10 cm over the course of two hours, or approximately 3.5 cm per hour. Thus, in this embodiment, a constant rate dilation method could include dilating the device at a constant rate to achieve approximately 3-3.5 cm of dilation per hour. This could be achieved in a number of ways, such as dilating approximately 0.5 cm every 10 minutes, 1 cm every 20 minutes, etc. Any of the devices described herein can be used to dilate at a constant rate. For example, referring to the devices of FIGS. 1-2, the expansion mechanism or knob can be rotated at set intervals or at a constant rate to achieve a constant rate of dilation. The diameter gauge can be monitored in combination with rotation of the expansion mechanism to achieve a constant dilation. Similarly, the automated system of FIG. 4 could be programmed to expand the device at any desired rate for any period of time.

Figure 19A:
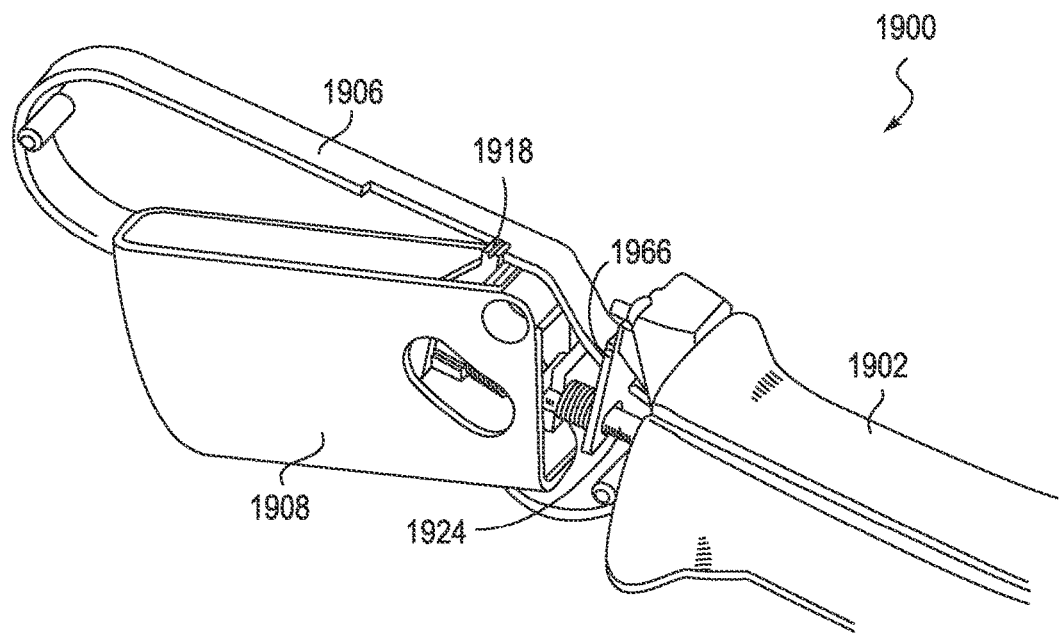
FIGS. 19A-19B illustrate yet another embodiment of a vaginal dilation device.
Figure 19B:
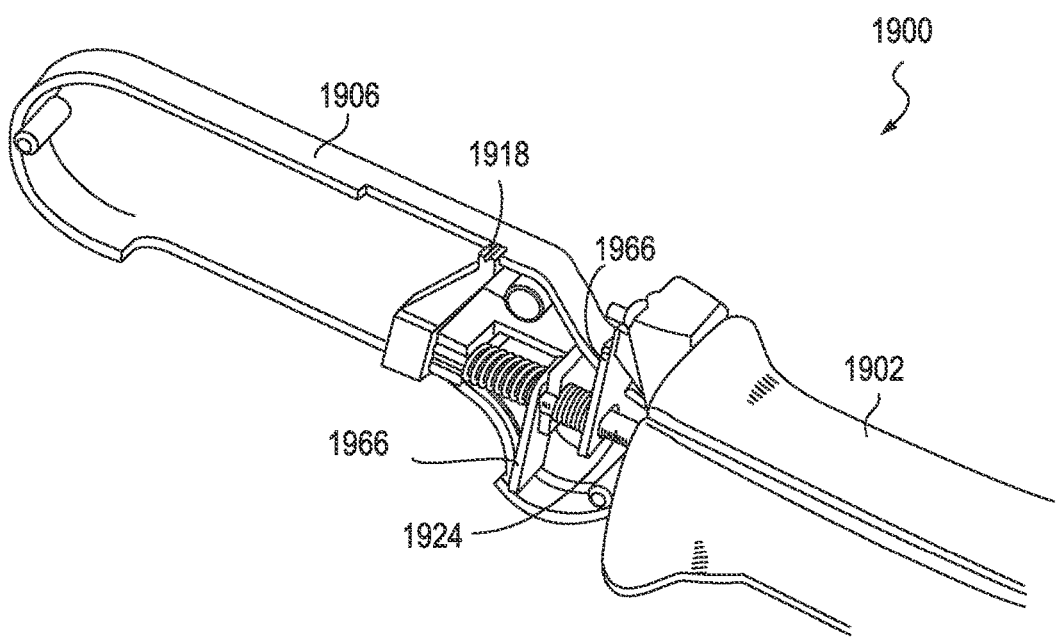

FIGS. 19A-19B illustrate another embodiment of a vaginal dilation device 1900. The device can include pads 1902, handle 1906, arms (not shown), expansion mechanism 1908 central rod 1924, diameter gauge 1918, and any of the features described above and shown in the Figures herein. In the embodiment of FIGS. 19A-19B, expansion mechanism 1908 comprises a trigger assembly configured to expand the device by a preset dilation increment.

FIG. 19B illustrates a cutaway view of device 1900. In FIG. 19B, central rod 1924 can comprise a hexagonal or non-circular shape, and plates 1966 can be configured to engage the central rod to prevent the rod from travelling axially. When the trigger assembly is actuated, it causes plates 1966 to become parallel, allowing the central rod to move axially. As the trigger assembly is actuated, the central rod moves proximally, causing arms (not shown) and pads (not shown) to expand outwardly from the device, as described above in the other embodiments of the vaginal dilation device.

In some embodiments, a single "click" or actuation of the trigger assembly can be configured to dilate the device by a preset set dilation increment. For example, the device can be configured to expand a precise amount with each actuation of the trigger assembly. This design makes device 1900 particularly suitable for use in a constant rate dilation scheme. In one embodiment, for example, the trigger assembly can be configured to expand the device by a preset dilation increment (e.g., approximately 0.5 cm) with every "click" or actuation of the trigger. The user can then actuate the trigger assembly after a pre-determined period of time (e.g., every 10 minutes) to dilate the device at a constant rate. In other embodiments, device 1900 includes force sensors, as described above, and the user can dilate the device based on the sensed force of the device. It should be understood that in other embodiments, the preset dilation increment can be any amount (e.g., 0-1 cm per actuation, 0-2 cm per actuation, 0-3 cm per actuation, 0-4 cm per actuation, etc) and the predetermined period of time can be any period of time (e.g., anywhere from 0-2 hours or even longer).

All embodiments of the vaginal dilator devices described herein can be used in other applications beyond dilating vaginal tissue for childbirth. For example, in one embodiment, the vaginal dilator devices described herein can be used for the treatment of vaginismus. In contrast to using the vaginal dilation devices described herein to prepare a woman for childbirth, in which a target tissue diameter is somewhere in the range of 8-10 cm, when using a vaginal dilator to treat vaginismus it may be desirable to only dilate the vaginal muscles from 1-4 cm. Thus, many features described herein, which enable the vaginal dilation device to expand to greater than 10 cm, are unnecessary in a vaginismus application. Instead of starting at a base diameter of 1 cm and expanding to 10 cm or more, a vaginismus dilation device according to one embodiment may expand from 1 cm to 4 cm to treat vaginismus. A method of treating vaginismus can comprise, for example, expanding a vaginal dilation device described herein into a vagina of a patient, and expanding the device to up to 4 cm. A vaginal dilation device can be expanded in a vagina at a constant rate to treat vaginismus, or alternatively, the vaginal dilation device can be expanded in the vagina with a constant force. The user of the device can monitor the force being applied by the device to the vagina, as well as the diameter of the device within the tissue. Additionally, any of the devices described herein can be used as vaginal exercise devices, or additionally, as cervical dilator devices.

Figure 33:
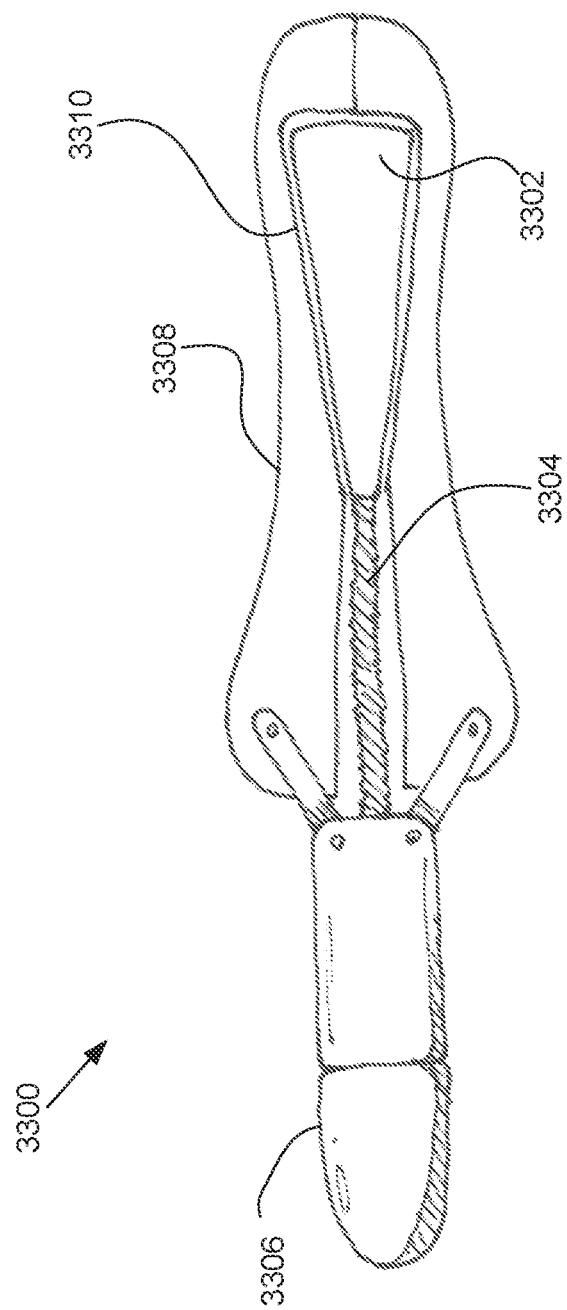
FIG. 33 illustrates another embodiment of a vaginal dilation device or a vaginal exercise device.

FIG. 33 illustrates one embodiment of a vaginal dilation device 3300 optimized to treat vaginismus. Since the device need only expand to approximately 4 cm, the scissor-like expansion mechanisms described above can be replaced with a simple cone structure 3302. The cone structure can be coupled to a central rod 3304. Manual rotation of knob 3306 can pull central rod and cone structure proximally Pads 3308 can include an internal cam surface 3310 configured to engage the cone structure. As the cone structure travels proximally, the internal cam surface 3310 of pads 3308 pushes the pads outwards, expanding tissue. It should be understood that any of the constant force (e.g., spring) or automated (e.g. motor) embodiments described above can be applied to the device of FIG. 33 in place of the manual knob.

Figure 34A:
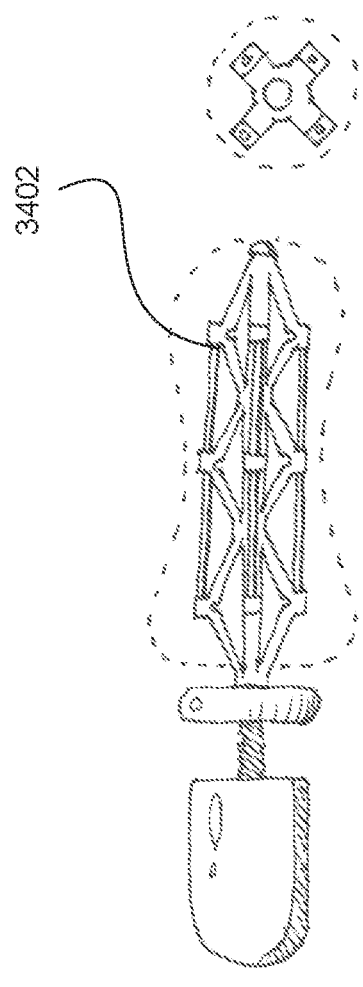
FIGS. 34A-34B illustrate another embodiment of a vaginal dilation device or a vaginal exercise device.
Figure 34B:
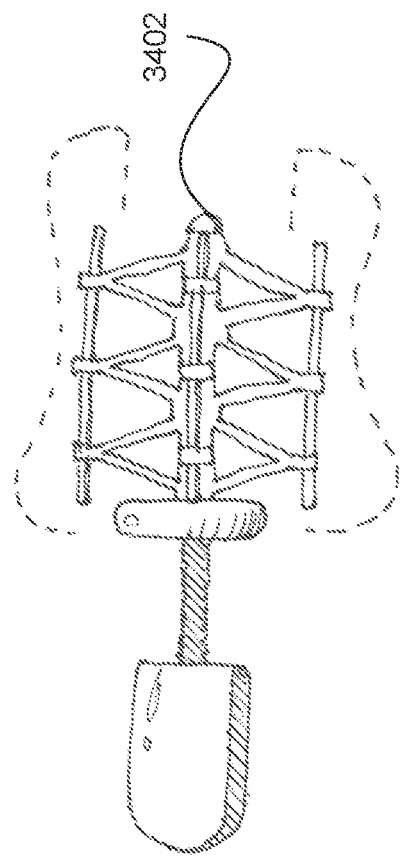

Another embodiment of an expandable vaginal dilation device is shown in FIG. 34. In this embodiment, the device utilizes a living hinge structure 3402 configured to expand in diameter when compressed axially. The axial compression of the device can be similar to any of the embodiments described above, in which a central rod is moved proximally within the device. The advantage of having small hinges as shown in FIG. 34 can be to increase the initial angle of the hinge, thus requiring less initial force to open and expand the device.

In another embodiment, instead of preparing a woman for childbirth or treating a vaginismus condition, a vaginal dilation device can instead be used as a home workout device, similar to "Kegel Exercises." In these embodiments, a user can use flex the vaginal muscles against any of the vaginal dilation devices described herein to build muscle strength to treat pelvic floor disorders. In these embodiments, vaginal dilation devices that provide an adjustable force and/or display the force applied by the device or the diameter of the device are preferred.

In FIG. 35, vaginal exercise device 3500 comprises a simple expansion mechanism comprising a pair of arms 3502 pivotable against a central rod 3504. A spring or other constant force mechanism 3506 can apply a pre-load force against the arms, thereby causing pads 3508 to expand outwards at the pre-load force. A force dial 3510 can give the user feedback as to the actual force applied by the user against the device. With this device, the user can adjust the amount of force applied by the device to the tissue with knob 3512, as well as see the amount of resistance applied by the user to the device.

Figure 36:
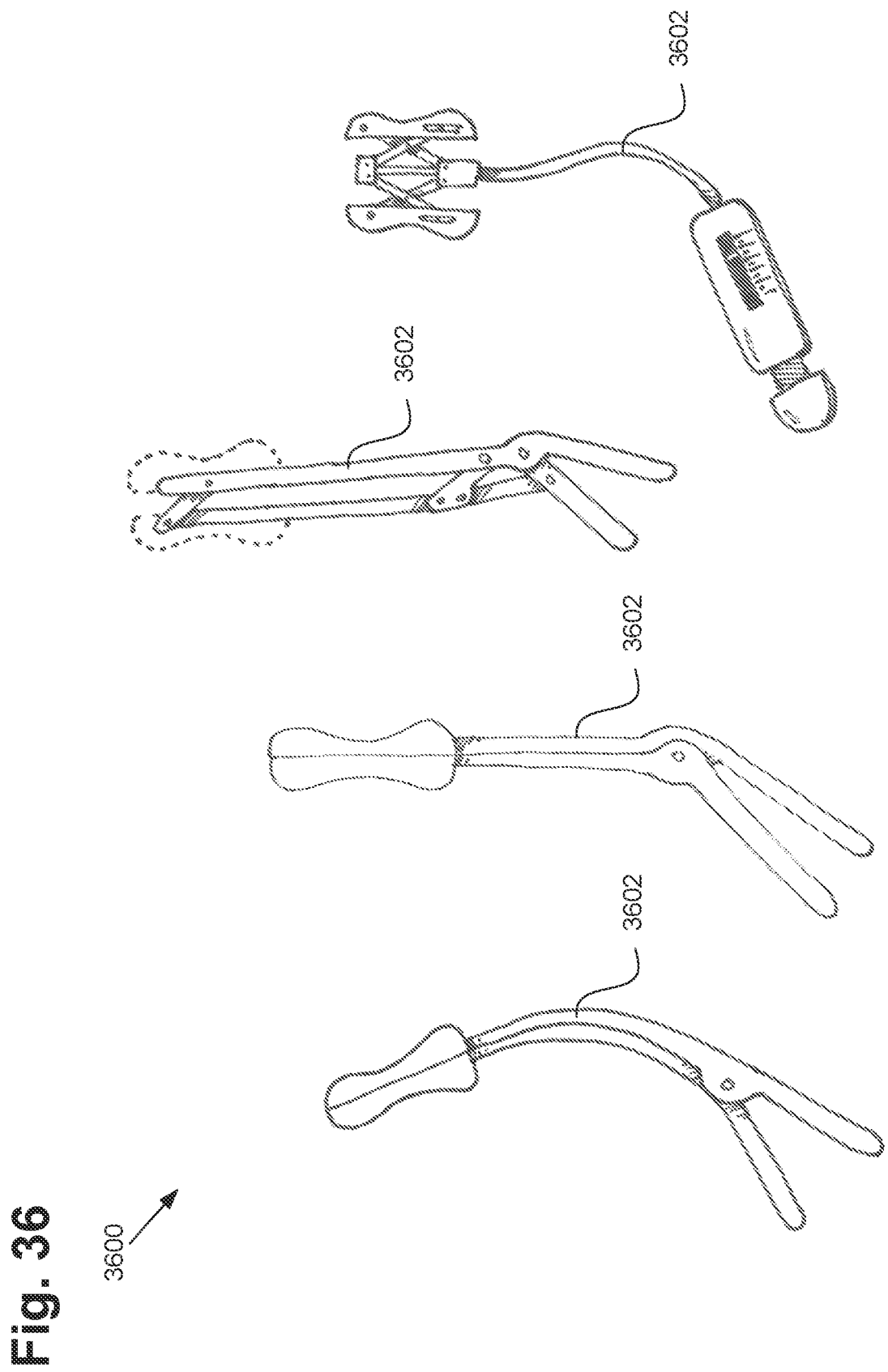
FIG. 36 illustrates one embodiment of a cervical dilation device.

FIG. 36 illustrates various embodiments of a cervical dilation device 3600. The cervical dilation device can incorporate any of the features of the vaginal dilation devices, described above. Additionally, the pads of the device as well as extension apparatus 3602 can be configured to provide access to the anatomy of the cervix. The cervical dilation device can be used during labor to accurately determine the diameter of the cervix and/or help along the cervical dilation process. Any of the methods described above, relating to vaginal dilation, can be instead used to dilate a cervix of the patient. In some embodiments, the cervical dilation device is configured to dilate the cervix from approximately 1 cm to 10 cm.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A vaginal dilation device, comprising:
   a handle disposed at a proximal portion of the device;
   a plurality of arms coupled to the handle and extending distally from the handle;
   an expansion mechanism coupled to the arms, located proximal to the handle, and configured to move the arms radially outwards at a controlled force; and
   a release disposed distal to the plurality of arms and configured to be at a location for delivery into a vaginal canal of a patient and configured to quickly reduce an outer diameter of the vaginal dilation device.

2. The vaginal dilation device of claim 1, further comprising a central rod coupled to the expansion mechanism, the handle, and the plurality of arms, wherein the vaginal dilation device is configured such that axial movement of the central rod moves the arms radially outwards from the central rod.

3. The vaginal dilation device of claim 1, wherein the arms are configured so as to be arranged in a parallel configuration when the arms move radially outwards.

4. The vaginal dilation device of claim 1, wherein each of the plurality of arms further comprises a pad disposed thereon.

5. The vaginal dilation device of claim 4, wherein the arms are configured such that a distance between opposing pads in an expanded configuration is 8-10 cm.

6. The vaginal dilation device of claim 1, further comprising a quick-release lever configured to quickly reduce the outer diameter of the vaginal dilation device.

7. The vaginal dilation device of claim 1, further comprising a force sensor configured to measure a force applied by the vaginal dilation device against the vaginal canal.

8. 1. A vaginal dilation device, comprising:
   a handle disposed at a proximal portion of the device;
   a plurality of arms coupled to the handle and extending distally from the handle;
   an expansion mechanism coupled to the arms, located proximal to the handle, and configured to move the arms radially outwards at a controlled rate; and
   a release disposed distal to the plurality of arms and configured to be at a location for delivery into a vaginal canal of a patient and configured to quickly reduce an outer diameter of the vaginal dilation device.

9. The vaginal dilation device of claim 8, further comprising a central rod coupled to the expansion mechanism, the handle, and the plurality of arms, wherein the vaginal dilation device is configured such that axial movement of the central rod moves the arms radially outwards from the central rod.

10. The vaginal dilation device of claim 8, wherein the arms are configured so as to be arranged in a parallel configuration when the arms move radially outwards.

11. The vaginal dilation device of claim 8, wherein each of the plurality of arms further comprises a pad disposed thereon.

12. The vaginal dilation device of claim 11, wherein the arms are configured such that a distance between opposing pads in an expanded configuration is 8-10 cm.

13. The vaginal dilation device of claim 8, further comprising a quick-release lever configured to quickly reduce the outer diameter of the vaginal dilation device.

14. The vaginal dilation device of claim 8, further comprising a force sensor configured to measure a force applied by the vaginal dilation device against the vaginal canal.

* * * * *